(12) United States Patent
Altieri et al.

(10) Patent No.: US 6,949,558 B2
(45) Date of Patent: Sep. 27, 2005

(54) ENHANCEMENT OF TAXANE-BASED CHEMOTHERAPY BY A CDK1 ANTAGONIST

(75) Inventors: Dario C. Altieri, Worcester, MA (US); Daniel S. O'Connor, Brooklyn Heights, NY (US)

(73) Assignee: Yale University, New Haven, CT (US)

( * ) Notice: Subject to any disclaimer, the term of this patent is extended or adjusted under 35 U.S.C. 154(b) by 10 days.

(21) Appl. No.: 10/284,490

(22) Filed: Oct. 31, 2002

(65) Prior Publication Data

US 2003/0125374 A1 Jul. 3, 2003

Related U.S. Application Data

(60) Provisional application No. 60/394,252, filed on Jul. 9, 2002, and provisional application No. 60/331,054, filed on Nov. 7, 2001.

(51) Int. Cl.$^7$ ........................ A61K 31/335; A61K 31/52
(52) U.S. Cl. ........................................ 514/261; 514/449
(58) Field of Search .................................. 514/449, 261

(56) References Cited

U.S. PATENT DOCUMENTS

| | | | |
|---|---|---|---|
| 6,235,776 B1 | 5/2001 | Pamukcu et al. | ........... 514/468 |
| 6,262,054 B1 | 7/2001 | Fennelly et al. | ........... 514/249 |

OTHER PUBLICATIONS

Altieri (2001) "The molecular basis and potential role of survivin in cancer diagnosis and therapy," *Trends Mol Med* 7:542–547.

Ambrosini et al (1997) "A novel anti–apoptosis gene, survivin, expressed in cancer and lymphoma," *Nat Med* 3: 917–921.

Chadebech et al. (2000) "Up–regulation of cdc2 protein during paclitaxel–induced apoptosis," *Int J Cancer* 87:779–786.

Grossman et al. (2000) "Inhibition of melanoma tumor growth in vivo by survivin targeting," *Proc Natl Acad Sci U S A* 98: 635–640.

Itzhaki et al. (1997) "Construction by gene targeting in human cells of a conditional CDC2 mutant that replicates its DNA," *Nat Gen* 15:258–265.

Li et al. (1999) "Pleiotropic cell–division defects and apoptosis induced by interference with survivin function," *Nat Cell Biolog* 1:461–466.

Motwani et al. (1999) "Sequential dependent enhancement of caspase activation and apoptosis by flavopiridol on paclitaxel–treated human gastric and breast cancer cells," *Clin Cancer Res* 5:1876–18783.

O'Connor et al. (2000) "Regulation of apoptosis at cell division by p34$^{cdc2}$ phosphorylation of survivin," *Proc Natl Acad Sci U S A* 97:13103–13107.

Rudner et al. (1996) "The spindle assembly checkpoint," *Curr Opin Cell Biol* 8: 773–780.

Schwarz et al. (1999) "Cell cycle targets p53, cyclins, cyclin–dependent kinases," *Clin. Cancer Res.* 5 (Suppl) A122 (Abstract).

Shimizu et al. (1995) "Unscheduled activation of cyclin B1 Cdc2 kinase in human promyelocytic leukemia cell line HL60 cells undergoing apoptosis induced by DNA damage," *Cancer Res* 55:228–231.

Sorger et al. (1997) "Coupling cell division and cell death to microtubule dynamics," *Current Opinion in Cell Biology* 9:807–814.

Vandre et al. (1989) "Anaphase onset and dephosphorylation of mitotic phosphoproteins occur concomitantly," *J Cell Sci* 94:245–258.

*Primary Examiner*—Rebecca Cook
(74) *Attorney, Agent, or Firm*—Morgan, Lewis & Bockius LLP

(57) ABSTRACT

The present invention provides a combination therapy for inhibiting the growth of tumor, for treating cancer, and for inducing cell death. The therapy comprises the sequential administration of taxane and a CDK1 antagonist. The present invention also provides pharmaceutical compositions comprising taxane and a CDK1 antagonist and kits comprising taxane and CDK1 antagonist.

33 Claims, 29 Drawing Sheets

SEQUENCE SPECIFICITY

COMPARATIVE ANALYSIS OF CDK INHIBITORY AGENTS

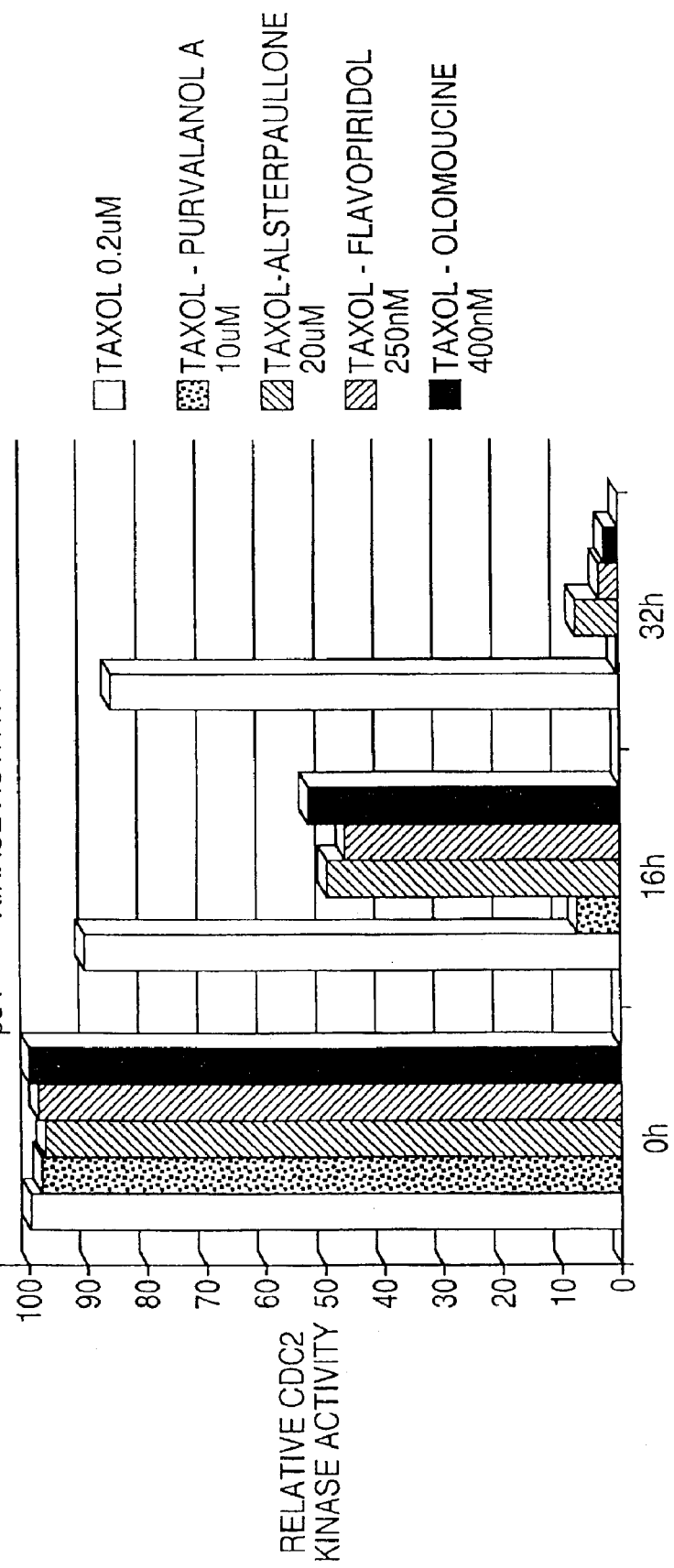

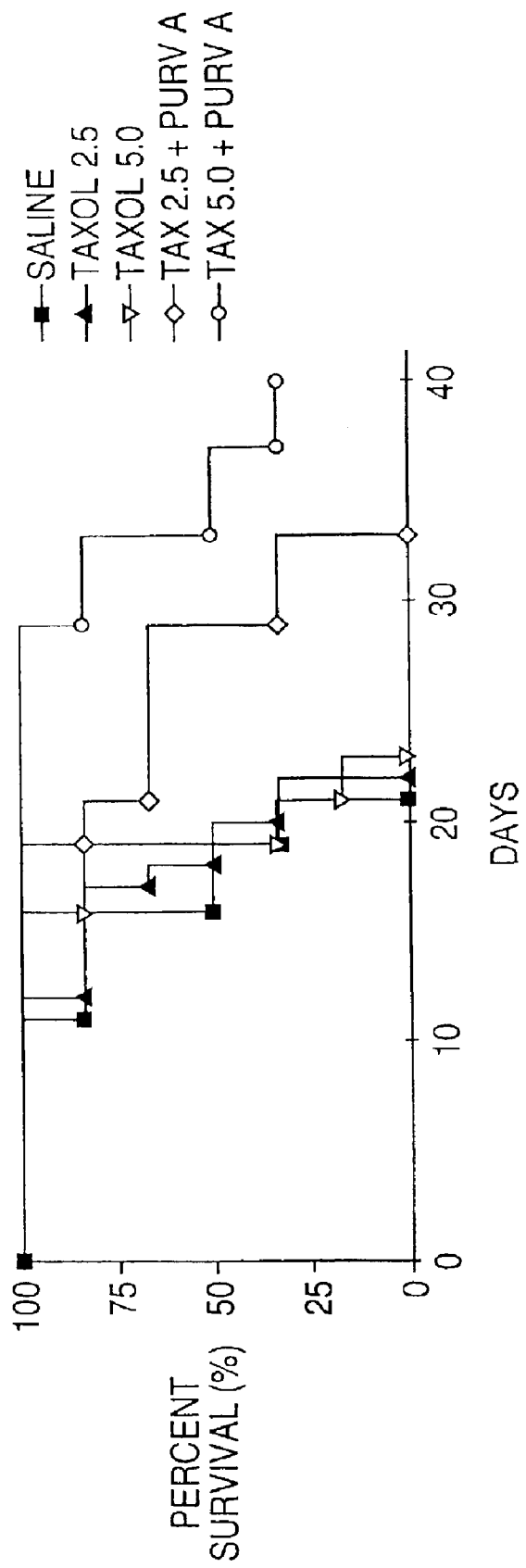

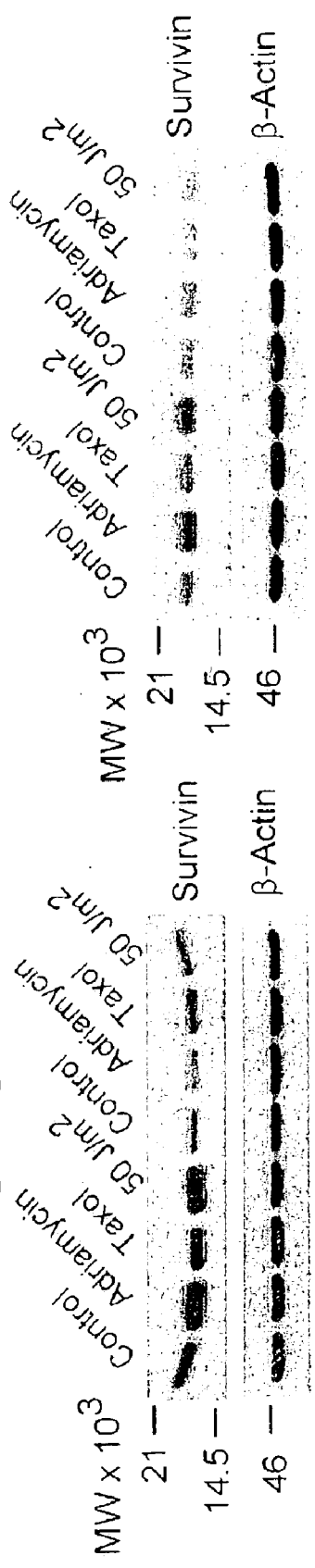
FIG. 13B
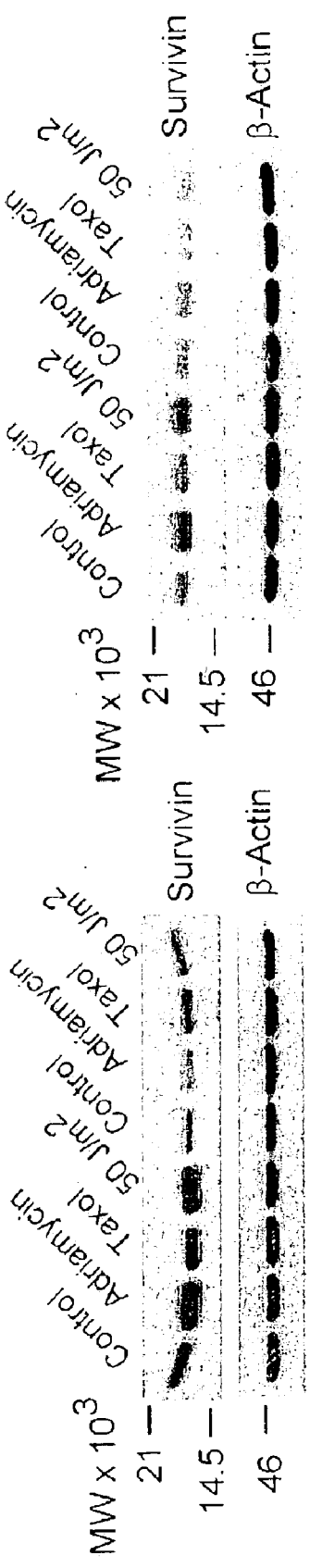
FIG. 13A
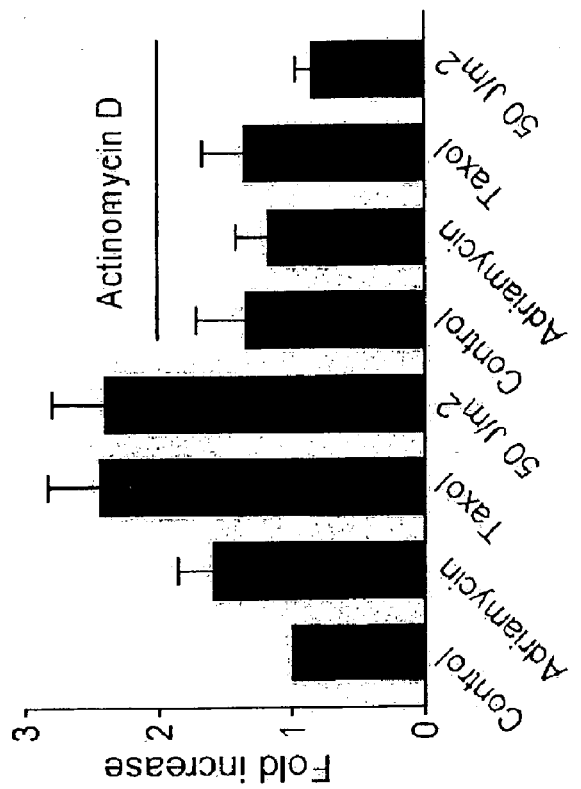
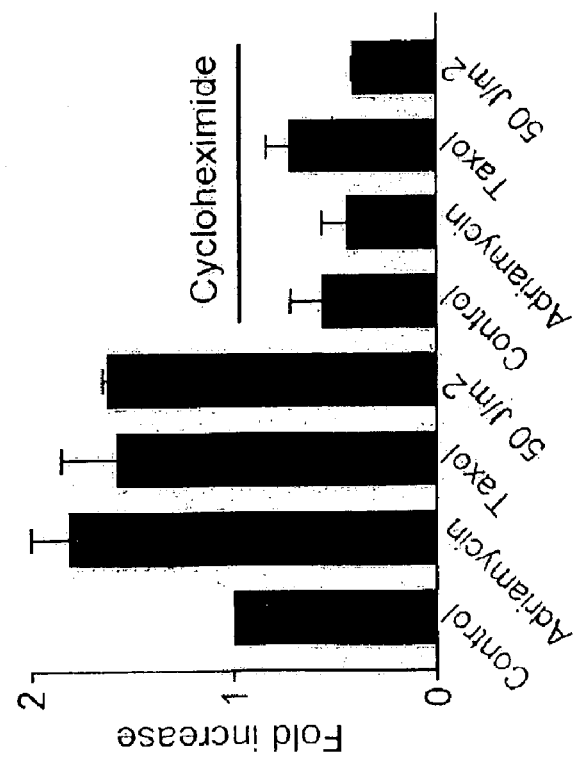

ENHANCEMENT OF TAXANE-BASED CHEMOTHERAPY BY A CDK1 ANTAGONIST

RELATED APPLICATIONS

This application claims the benefit of U.S. Provisional Application No. 60/331,054, filed Nov. 7, 2001, and U.S. Provisional Application No. 60/394,252, filed Jul. 9, 2002, which are herein incorporated by reference in their entirety.

The research carried out in the present application was supported in part by NIH Grant Nos CA78810 and CA90917. The government may have certain rights in the invention of the present application.

FIELD OF THE INVENTION

The present invention relates to combination therapy for the treatment of cancer, for inhibiting growth of tumors, and for inducing cellular apoptosis. Specifically, the therapy comprises the administration of at least one compound, for example taxane, that arrests cell mitosis and at least one compound, such as a CDK1 antagonist, that prevents the phosphorylation of survivin. The present invention also relates to sequential administration of taxane and a CDK1 antagonist. Moreover, the present invention relates to pharmaceutical compositions and to kits comprising taxane and CDK1 antagonist.

BACKGROUND OF THE INVENTION

Cell Cycle

Living organisms are composed of cells, whose growth and division require a regular sequence of events and processes that make up a cell cycle. A cell cycle comprises two periods: 1) interphase, the period of cell growth, and 2) mitosis, cell division and the separation of daughter of cells. Some cell cycle events are continuous (e.g., synthesis of RNA, proteins, and lipids), whereas others are discontinuous (e.g., DNA synthesis). Two discontinuous processes for cell survival are the replication of DNA and the segregation of chromosomes to the daughters of cell division during mitosis. If either of these steps are performed inaccurately, the daughter cells will be different from each other and will almost certainly be flawed. Chromosome replication occurs in eukaryotic cells only during interphase; and DNA replication and DNA segregation are mutually exclusive processes.

Interphase is subdivided into the S phase (synthetic phase) when DNA replication occurs, and the gaps, G1 and G2, separating the S phase from mitosis. G1 is the gap after mitosis, before DNA synthesis starts; G2 is the gap after DNA synthesis is complete, before mitosis and cell division. During G1 and G2, no net synthesis of DNA occurs. As mentioned above, during interphase, there is continued cellular growth and continued synthesis of other cellular macromolecules such as RNA, proteins, and membranes. Additionally, centrioles which are composed of microtubules duplicate during interphase.

Segregation of chromosomes as well as mitotic spindles, occurs during mitotic (M) period, normally a relatively brief period in the cell cycle, which culminates in the highly visible act of cell division (e.g., cytokinesis). The appearance of chromosomes as thin threads inside the nucleus indicates the beginning of mitosis. The mitotic period is divided into four substages which are prophase, metaphase, anaphase, and telophase.

During prophase, each chromosome is composed of two chromatids held together by their centromeres. Each of the chromatids contains one of the two daughter DNA molecules replicated during the S phase. The centrioles generate microtubules and move to opposite poles. Those microtubules that associate with fibers and proteins form spindle fibers. At the end of prophase, the centrioles are at opposite poles. Some spindle fibers extend from the centrioles at the poles to the equator of the cell, while others extend from the poles to the chromatids attached to the kinetochores near the centromeres of the chromatids.

In metaphase, the chromosomes move to the equator of the cell and align in the equatorial plane.

During anaphase, the daughter chromatids separate and move toward the pole to which it is linked by a spindle fiber. At the same time, both the cell and the spindle fibers elongate. At late anaphase, a cleavage furrow starts to form which begins the process of cytokinesis.

During telophase, new membranes form around the daughter nuclei. At the end of telophase, cytokinesis is nearly complete; the spindle fibers disappear and the microtubules and other fibers depolymerizes. At the end of the mitotic phase, identical copies of the cellular DNA are distributed to each of the daughter cells.

The Mitotic Spindle and Tubulin

Microtubule formation is important for cell mitosis, cell locomotion, and the movement of highly specialized cell structures such as cilia and flagella. The mitotic spindle is a self-organizing structure that is constructed primarily from microtubules. Among the most important spindle microtubules are those that bind to kinetochores and form the fibers along which chromosomes move. These microtubules are comprised of α-β tubulin dimers. γ-tubulin is a phylogenetically conserved component of microtubule-organizing centers that is essential for viability and microtubule function (T. Horio et al. (1994) *J. Cell Biol.* 126(6): 1465–73). It is exclusively localized at the spindle poles (also known as spindle pole bodies, SPB) in mitotic animal cells, where it is required for microtubule nucleation (M. A. Martin et al. (1997) *J. Cell Sci.* 110(5): 623–33; I. Lajoie-Mazenc et al. (1994) *J. Cell Sci.* 107(10): 2825–37). γ-tubulin is also found on osmiophilic material that lies near the inner surface of the nuclear envelope, immediately adjacent to the SPB (R. Ding et al. (1997) *Mol. Biol. Cell* 8(8): 1461–79).

One protein linked with the mitotic spindle is p53, which is a critical participant in a signal transduction pathway that mediates either a G1 arrest or apoptosis in response to DNA damage (S. E. Morgan et al. (1997) *Adv. Cancer Res.* 71: 1–25). Loss of p53, in addition to suppression of apoptosis by bcl-2-related genes, may act cooperatively to contribute to genetic instability (A. J. Minn et al. (1996) *Genes Dev.* 10(2): 2621–31). The oncoprotein, Bcl-2, also has been demonstrated to be cell cycle specific, appearing in early prophase or late G2 and persisting throughout mitosis. The pattern of bcl-2 protein localization shows a diffuse nuclear distribution before chromosome condensation, followed by a specific concentration of bcl-2 at the margins of condensed chromosomes in prophase, metaphase and anaphase (M. C. Willingham et al. (1994) *J. Histochem. Cytochem.* 42(4): 441–50).

As microtubules and microtubule-related structures are intimately involved in the mitotic process, they have provided a convenient target for putative anti-mitotic compounds. Indeed, microtubules have proven to be extremely labile structures that are sensitive to a variety of chemically unrelated anti-mitotic drugs. For example, colchicine and nocadazole are anti-mitotic drugs that bind tubulin and inhibit tubulin polymerization (Stryer (1988) Biochemistry).

When used alone or in combination with other therapeutic drugs, colchicine has been used to treat cancer (WO9303729; J03240726-A), alter neuromuscular function, change blood pressure, increase sensitivity to compounds affecting sympathetic neuron function, depress respiration, and relieve gout (Physician's Desk Reference, (1993) 47: 1487).

Taxol and the vinca alkaloids are chemotherapeutics that bind microtubles. They perturb kinetochore-microtubule attachment and disrupt chromosome segregation. This activates a check point pathway that delays cell cycle progression and induces programmed cell death (P. K. Sorger et al. (1997) Curr. Opin. Cell. Biol. 9(6): 807–14; C. M. Ireland et al. (1995) Biochem. Pharmacol. 49(10): 1491–99). Taxol has been demonstrated to induce tubulin polymerization and mitotic arrest which is followed by apoptosis. Overexpression of Bcl-x(L) in taxol induced cells has been demonstrated to interfere with the activation of a key protease involved in apoptosis (A. M. Ibrado et al. (1996) Cell Growth Differ. 7(8): 1087–94).

Cyclin, Cyclin-Dependent Kinases, and their Inhibitors

Regulation of the cell cycle by cellular constituents ensures the controlled generation of cells with specialized functions. Cyclin and cyclin-dependent kinases (CDKs) are molecules that play a key role in regulating the eukaryotic cell cycle. Cyclin/CDK complexes are formed via the association of a regulatory cyclin subunit (such as cyclin A) and a catalytic kinase subunit (such as cdc2 or CDK1). Sequential formation, activation, and subsequent inactivation of a series of cyclin/cyclin dependent kinase complexes controls the progression of eukaryotic cells through the three phases of the growth cycle (G1, S, and G2) leading to division in the mitotic phase (M). Each step in the cell cycle is regulated by a distinct and specific cyclin-dependent kinase. For example, complexes of Cdk4 and D-type cyclins govern the early G1 phase of the cell cycle, while the activity of the CDK2/cyclin E complex is rate limiting for the G1 to S-phase transition. The CDK2/cyclin A kinase is required for the progression through S-phase and the cdc2/cyclin B complex controls the entry into M-phase (Sherr (1993) Cell 73: 1059–1065).

Cdc2, the first identified CDK, was discovered as a gene essential for both G1/S and G2/M transitions in yeast (Nurse et al., (1981) Nature 292: 558–560). The cloning of the gene encoding the human homolog of Cdc2, CDK1, by complementation led to the identification of cdc2 homologs in all eukaryotes from plants and unicellular organisms to humans and to the realization that cdc2 was only the first member of a family of closely related kinases. CDKs are typical Ser/Thr kinases comprising eleven subdomains shared by all protein kinases. Examples of CDKs include, but are not limited to cdc2, CDK1, CDK2, CDK4, CDK5, CDK6, and CDK7.

Following the discovery of cyclin B in sea urchin eggs, cyclin B homologs were identified in all eukaryotes. Like cdc2, cyclin B is one member of a large family of kinase regulators. Members of the family include but are not limited to cyclin A, cyclin B1–B3, cyclin C, cyclin D1–D3, cyclin E, and cyclin H.

Examples of cyclin/CDK complexes include, but are not limited to cyclin A/cdc2 or cdk2, cyclin B1–B3/cdc2, cyclin C/cdk8, cyclin D1–D3/cdk2, cdk4, cdk5, or ckd6, cyclin E/cdk2, and cyclin H/cdk7.

Cyclin dependent kinase inhibitors (CKIs) are also essential for regulating the cell cycle. CKIs negatively regulate CDK or cyclin/CDK activity by associating with them. By binding specifically to either CDK, or the cyclin/CDK complexes, they inhibit the cyclin/CDK complexes. CKI activity and levels are cell cycle regulated allowing these proteins to function as inhibitors of their cognate cyclin/CDK complexes for very limited periods during the cell cycle. Examples of a few CKIs include purvalanol, olomoucine, roscovitine, flavopiridol, and alsterpaullone.

The discovery that human CDKs, cyclins and CKIs are mutated or abnormally expressed in a number of cancerous cells confirms that these gene products and their functions are essential for mammalian cell cycle regulation (reviewed in Hunter (1993) Cell 75: 839–841; Marx (1993) Science 262: 1644–1645; Marx (1994) Science 263: 319–321; Sherr (1996) Science 274: 1672–1677). Altered expression of cyclins, CDKs, and their modulators in malignant cells, results in deregulated CDK activity and uncontrolled growth of malignant cells.

Apoptosis and Survivin

Apoptosis or programmed cell death is a natural form of death that organisms use to dispose of cells. It occurs in response to different factors such as growth factor addition or withdrawal, antitumoral drugs, viral infections, activation tumor suppressor genes, and cytotoxic agents. These factors are also known to modify cell cycle progression. Evan (1995, Curr. Opin. Cell Biol. 7: 825–834) reports that apoptosis and cell cycle controls are closely linked.

Deregulated expression of inhibitors of apoptosis (programmed cell death) is thought to contribute to cancer by abnormally extending cell viability, favoring the accumulation of mutations, and promoting resistance to therapy (Reed (1999) J. Clin. Oncol. 17: 2941–53). A novel modulator of the cell death/viability balance in cancer was recently identified as survivin (Ambrosini et al. (1997) Nat. Med. 3: 917–21), a member of the Inhibitor of Apoptosis (IAP) gene family (Deveraux et al. (1999) Genes Dev. 13: 239–52).

Survivin is a 16.5 kDa cytoplasmic protein containing a single partially conserved BIR (baculovirus IAP repeats) domain, and a highly charged carboxyl-terminus coiled-coil region instead of a RING finger, which inhibits apoptosis induced by growth factor (IL-3) withdrawal when transferred in B cell precursors (Ambrosini et al. (1997) Nat Med 3: 917–921). Based on overall sequence conservation, the absence of a carboxyl terminus RING finger and the presence of a single, partially conserved, BIR domain, survivin is the most distantly related member of the IAP family, sharing the highest degree of similarity with NAIP (neuronal apoptosis inhibitory protein; Roy et al. (1995) Cell 80: 167–178). Additionally, unlike other IAP proteins, survivin is undetectable in normal adult tissues, but becomes the top fourth transcript expressed in common human cancers (Ambrosini et al. (1997) Nat. Med. 3: 917–21; Velculescu et al. (1999) Nat. Genet. 23: 387–88), such as lung, colon, breast, pancreas, and prostate, and in ~50% of high-grade non-Hodgkin's lymphomas, in vivo.

Survivin is expressed in the G2/M phase of the cell cycle in a cell cycle-dependent manner, and localized to mitotic spindle microtubules and intercellular actomyosin bridges, i.e. midbodies, during cell division (Li et al. (1998) Nature 396: 580–584). Interference with this topography, or blocking survivin expression, caused increased caspase-3 activity in G2/M (Li et al. (1998) Nature 396: 580–584), and a profound dysregulation of mitotic progression (Li et al. (1999) Nat. Cell Biolog. 1: 461–466), suggesting that survivin may regulate a novel apoptotic checkpoint at cell division. This pathway was dramatically exploited in cancer (Ambrosini et al. (1997) Nat. Med. 3: 917–921), where survivin was identified as one of the top four "transcriptomes" out of 3.5 millions mRNAs, uniformly expressed in cancer, but not in normal tissues (Velculescu et al. (1999) *Nat. Genet.* 23: 387–388). Additionally, it has been shown that transformed cells are exquisitely sensitive to manipulation at this mitotic checkpoint as interference with survivin expression and function using dominant-negative mutants with point mutations in the conserved baculovirus IAP repeat (BIR) domain or survivin antisense resulted in aberrant mitoses (Li et al. (1999) *Nat. Cell Biolog.* 1: 461–466) and spontaneous apoptosis (Ambrosini et al. (1998) *J Biol Chem.* 273: 11177–82; Grossman et al. (1999) *Lab Invest* 79: 1121; Grossman et al. (1999) *J. Invest. Dermatol.* 113: 1076–81). This phenotype is unique to survivin and not observed with other apoptosis inhibitors potentially contributing to neoplasia, as antisense inhibition of Bcl-2 increased sensitivity to apoptosis but did not in itself induce cell death (Jansen et al. (1998) *Nat. Med.* 4: 232).

O'Connor et al. (2000 *Proc Natl Acad Sci USA* 97: 13103–7) teach that survivin is phosphorylated on Thr$^{34}$ by the main mitotic kinase kinase complex, cyclin B1/p34$^{cdc2}$, in vitro and in vivo. Loss of phosphorylation on Thr$^{34}$ results in dissociation of a survivin-caspase-9 complex on the mitotic apparatus, and caspase-9-dependent apoptosis of cells traversing mitosis. These data suggest that survivin is a mitotic substrate of p34$^{cdc2}$-cyclin B1 and survivin phosphorylation on Thr$^{34}$ may be required to preserve cell viability at cell division.

Grossman et al. (2001 *Proc Natl Acad Sci USA* 98: 635–40) report that expression of a phosphorylation-defective survivin mutant (Thr$^{34}$→Ala) triggered apoptosis in several human melanoma cell lines and enhanced cell death induced by the chemotherapeutic drug cisplatin in vitro. Conditional expression of survivin Thr$^{34}$→Ala in YUSAC2 melanoma cells prevents tumor formation upon s.c. (subcutaneous) injection into CB.17 severe combined immunodeficient-beige mice. When induced in established melanoma tumors, survivin Thr$^{34}$→Ala inhibits tumor growth by 60–70% and cause increased apoptosis and reduced proliferation of melanoma cells in vivo.

Anti-cancer treatments exploit activation of cell cycle checkpoints to arrest cell proliferation and induce apoptosis. However, escape mechanisms engendered by tumor cells may preserve cell viability in face of checkpoint activation, favoring aberrant mitotic progression and exacerbating genomic instability. Survivin, a member of the Inhibitor of Apoptosis (IAP) gene family expressed in most human cancers, requires phosphorylation by p34$^{cdc2}$-cyclin B1 for cytoprotection.

p34$^{cdc2}$ Survival Checkpoint in Cancer

Checkpoints act as surveillance mechanisms to ensure proper timing of the cell division cycle (C. J. Sherr (1996) *Science* 274: 1672–77). At mitosis, the assembly of a bipolar spindle is vital to the preservation of genetic fidelity between daughter cells, and is monitored by a checkpoint (A. D. Rudner et al. (1996) *Curr. Op. Cell Biol.* 8: 773–80) that senses microtubule defects (S. S. L. Andersen (2000) *Trends Cell Biol.* 10: 261–67), or aberrant kinetochore attachment (R. B. Nicklas (1997) *Science* 275: 632–637). Activation of the spindle checkpoint by mitotic stresses causes a prolonged arrest of cell division that may eventually lead to apoptosis, or programmed cell death (M. O. Hengartner (2000) *Nature* 407: 770–76.). This strategy has been exploited for anti-cancer treatments, and agents that perturb microtubule dynamics or interfere with microtubule assembly (P. K. Sorger et al. (1997) *Curr. Biol.* 9: 807–14) have shown efficacy in the management of common human tumors (Rowinsky and Donehower, 1995).

Among the regulators of apoptosis that may affect the cell death/viability balance of dividing cells, interest has recently focused on the Inhibitor of Apoptosis (IAP) (Q. L. Deveraux, Q. L. et al. (1999) *Genes Dev* 13: 239–252) protein and mitotic regulator, survivin (D. C. Altieri (2001) *Trends Mol. Med.* 7: 542–47.). Expressed during cell division in a cell cycle-dependent manner and localized to various components of the mitotic apparatus, survivin has been implicated in both regulation of spindle microtubule function and preservation of cell viability (D. C. Altieri (2001) *Trends Mol. Med.* 7: 542–47; J. C. Reed, J. C. et al. (2000) *Cell* 102: 545–48). A critical requisite for survivin function was identified in the phosphorylation on Thr$^{34}$ (D. S. O'Connor et al. (2000) *Proc. Natl. Acad. Sci. USA* 97: 13103–107) by the main mitotic kinase, p34$^{cdc2}$-cyclin B1 (J. Pines (1999) Nat. Cell Biolog. 1: E73–E79). Accordingly, expression of non-phosphorylatable survivin Thr$^{34}$→Ala prevented phosphorylation of endogenous survivin and triggered apoptosis of various cancer cell types (D. Grossman et al. (2001) *Proc. Natl. Acad. Sci. USA* 98: 635–640; D. S. O'Connor et al. (2000) *Proc. Natl. Acad. Sci. USA* 97: 13103–107). When tested in mouse cancer models, expression of survivin Thr$^{34}$→Ala induced apoptosis in situ, suppressed tumor formation, and inhibited growth of established tumors (D. Grossman et al. (2001) *Proc. Natl. Acad. Sci. USA* 98: 635–640; M. Mesri et al. (2001) *J. Clin. Invest.* 108: 981–990), suggesting that this phosphorylation step may provide a suitable target for anti-cancer therapy. Although the role of p34$^{cdc2}$-cyclin B1 as a universal mitotic switch is well established (J. Pines (1999) Nat. Cell Biolog. 1: E73–E79), its potential contribution to cell death/survival during spindle checkpoint activation has remained controversial (W. Ongkeko et al. (1995) *J. Cell Scie.* 108: 2897–2904.; F. Shi et al. (1994) *Science* 263: 1143–1145).

SUMMARY OF THE INVENTION

The present invention provides a method of inducing tumor cell apoptosis, inhibiting the growth of a tumor, inducing cell death in a malignant cell population, and treating a patient with cancer comprising the use of a combination therapy. The combination therapy of the present invention comprises administering an effective dose of at least a compound that disrupts mitosis in a cell and at least one compound that modulates or prevents a survivin function, such as a survivin antagonist. In a preferred embodiment, the compound that arrests mitosis is a taxane or adriamycin and the compound that inhibits survivin function inhibits survivin phosphorylation.

Preferably, the agents are administered sequentially. More preferably, the CDK1 antagonist is administered about: 4 hours, 8 hours, 16 hours, 18 hours, 24 hours or 32 hours after the administration of taxol. Even more preferably, the CDK1 antagonist is administered between about 16 and 24 hours after administration of taxol. Most preferably, the CDK1 antagonist is administered about 18 hours after the administration of taxol.

In one embodiment of the invention, the taxane is selected from the group consisting of taxol, taxol analogs, docetaxel, and docetaxel analogs. Preferably, the taxane is a taxol.

In another embodiment of the invention, the CDK1 antagonist is a cyclin dependent kinase inhibitor (CKI). Preferably, the cyclin dependent kinase inhibitor is butyrolactone I, a paullone, or a purine analog selected from the group consisting of olomoucine, roscovitine, CVT-313 and purvalanol derivatives, for example, purvalanol A and purvalanol B. More preferably, the purine analog is purvalanol A.

The present invention contemplates the use of the combination therapy to treat cancers comprising administering taxane and a CDK1 antagonist. Preferably, the cancers are selected from the group consisting of breast cancer, ovarian cancer, lung cancer, AIDS related-Kaposi's sarcoma and nonsmall cell lung cancer. More preferably, the cancer is breast or ovarian cancer.

Moreover, the present invention provides a sequential therapy comprising taxane and CDK1 antagonist, wherein the CDK1 antagonist is administered about 16–24 hours after taxol administration. Preferably, the CDK1 antagonist is administered about 18 hours after taxane administration.

The combination therapy of the present invention enables the use of lower levels of chemotherapeutic agents such as taxane which reduces toxicity towards normal tissues. The combination therapy of the present invention is also able to induce cancer cell death with a faster and more effective kinetics than either agent used alone, i.e., there is a synergistic effect.

Further, the present invention provides compositions comprising a compound that arrests cell mitosis and a compound that inhibits a survivin function. Preferably, the compositions are formulated as pharmaceutical compositions comprising effective dosages for sequential delivery. More preferably, the compound that arrests cell mitosis is a taxane and the compound that inhibits survivin function is a CDK1 antagonist. Most preferably, the taxane is taxol and the CDK1 antagonist is a CKI, such as purvalanol A.

Alternatively, the present invention provides composition comprising adriamycin and a CDK1 antagonist. In one embodiment, the CDK1 antagonist is administered about: 18 hours, 24 hours, or 48 hours after the administration of adriamycin. Preferably, the CDK1 antagonist is flavopiridol.

The present invention also provides kits comprising a compound that arrests cell mitosis and a compound that inhibits a survivin function. Preferably, the kits comprises effective dosages of the compounds and are formulated as pharmaceutical compositions for sequential delivery.

BRIEF DESCRIPTION OF THE DRAWINGS

FIG. 10 shows the effect of taxol and various CKIs on cdc2 kinase activity.

FIGS. 11A–C show the results of the xenograph mouse model. A. Injection Protocol using the xenograph mouse model. B. Xenograph Tumor Growth. C. Survival Curve.

FIGS. 13A–D show requirements for induced survivin expression by anticancer agents. A, B. Effect of translational/transcriptional inhibitors. MCF-7 cells ($2 \times 10^5$/ml) were incubated with cycloheximide (A, 2 mg/ml), or actinomycin D (B, 1 $\mu$g/ml), treated with adriamycin (100 nM), taxol (2 $\mu$M), or UVB irradiation (50 J/m$^2$), and analyzed for expression of survivin or β-actin by Western blotting and densitometry (bottom panel) after a 48 h culture. Relative molecular weight markers in kDa are shown on the left. C. Northern hybridization. Total RNA was extracted from adriamycin-treated MCF-7 cells at the indicated time intervals and hybridized with a $^{32}$P-dCTP labeled survivin cDNA (top). Proper loading was confirmed by comparison to 28S and 16S ribosomal RNA (bottom). D. Survivin promoter activity. HeLa or MCF-7 cells were transfected with a minimal survivin promoter upstream of a luciferase reporter gene (pLuc-cyc1.2), and analyzed for luciferase activity in a luminometer at 0–24 h after treatment with the indicated anti-cancer agents. Data represent the average of two independent experiments. Luciferase activity was normalized to β-galactosidase activity used as an internal control.

FIGS. 22A–D show requirement of stabilized microtubules and p34$^{cdc2}$ activity for metaphase viability checkpoint. A. MPM-2 activity. HeLa cells were treated with the microtubule-depolymerizing agent, vincristine (100 nM, □) or vincristine followed by Purvalanol A (20 μM, ■), and analyzed for MPM-2 phosphoepitope expression at the indicated time intervals. B. Determination of apoptosis. The experimental conditions are as in A. Induction of apoptosis was monitored at the indicated time intervals by propidium iodide staining and flow cytometry. Inset. Modulation of survivin expression. HeLa cells were left untreated (None) or treated with vincristine (Vincr.) or the sequential combination of vincristine-Purvalanol A, and analyzed for expression of survivin or cyclin B1, by Western blotting. C. Genetic ablation of p34$^{cdc2}$ kinase activity. HT2–19 cells in the presence (p34$^{cdc2}$ +/−) or absence (p34$^{cdc2}$ −/−) of IPTG were simultaneously treated with vehicle or taxol (0.2 μM for 24 h) and analyzed for induction of apoptosis by propidium iodide staining and flow cytometry. The percentage of cells with hypodiploid (apoptotic), 2N, or 4N DNA content is indicated. D. Expression of survivin reverses apoptosis induced by ablation of p34$^{cdc2}$. HT2–19 cells in the absence of IPTG (p34$^{cdc2}$ −/−) were infected with pAd-GFP (■) or pAd-Survivin (□) and analyzed for induction of apoptosis at the indicated time intervals by propidium iodide staining and flow cytometry. The percentage of apoptosis in IPTG–HT2–19 cells in the absence of viral transduction was 17.4% (48 h) and 24% (72 h). For both panels, data are representative of two independent determinations.

Figure 23A:
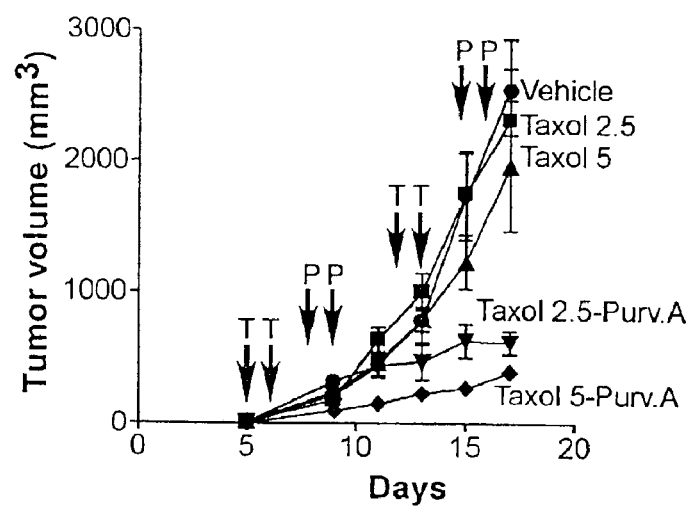
Figure 23B:
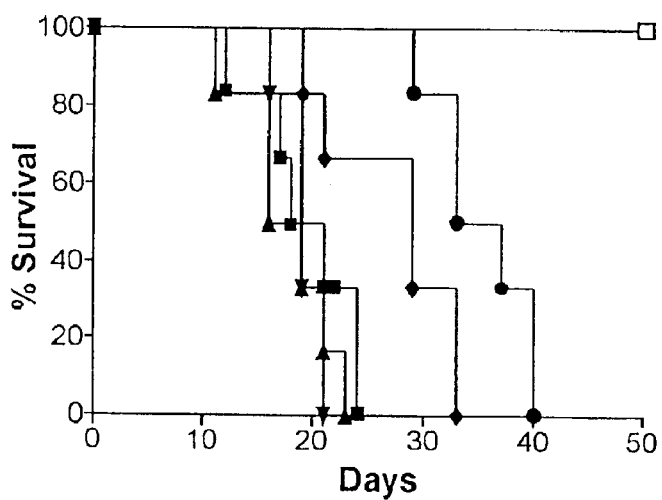
Figure 23C:
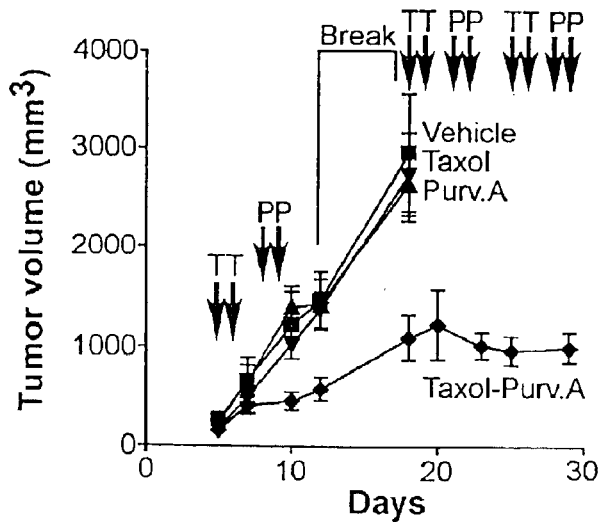

FIGS. 23A–C show sequential ablation of p34$^{cdc2}$ kinase activity after microtubule damage suppresses tumor growth, in vivo. A. MCF-7 cells (2.5×10$^6$) were injected subcutaneously in the flank of immunocompromised CB17 SCID mice, and grown as superficial tumors for 5 d (~50–75 mm$^3$) before initiation of treatment. Animals (6/group) were injected i.p. with vehicle, taxol alone (T, 2.5 or 5 mg/kg), or the sequential combination of taxol-Purvalanol A at the indicated intervals (arrows) followed by a day with no treatment. For single agent treatment, vehicle was given in place of taxol or Purvalanol A with the same schedule. Each cycle was separated by 2 d without treatment. Tumor volume was measured in the three dimensions with a caliper. B. The experimental conditions are as in A. Treatment was terminated on d. 16 for all groups except for group □, where sequential administration of taxol-Purvalanol A was continued as in A. For all groups, tumor size was monitored at the indicated time intervals, and animals with tumor burden >3000 mm$^3$ were sacrificed (Survival). ■, vehicle; ▲, taxol alone (2.5 mg/kg); ▼, taxol alone (5 mg/kg); ♦, taxol (2.5 mg/kg)-Purvalanol A; ●, taxol (5 mg/kg)-Purvalanol A; □, taxol (2.5 mg/kg)-Purvalanol A continuous treatment. C. The experimental conditions are as in A. In the Purvalanol A alone group, animals were injected i.p. with 20 mg/kg Purvalanol A with the indicated schedule. Sequential treatment with taxol (5 mg/kg) followed by Purvalanol A (20 mg/kg) was suspended for the indicated time interval (Break) and re-administered on d.18 with the same schedule as in A. All animals treated with vehicle, taxol alone (5 mg/kg) or Purvalanol A alone (20 mg/kg) reached tumor burdens >3000 mm$^3$ on d. 20 and were sacrificed.

DETAILED DESCRIPTION

1. General Description

The present invention is based in part on the surprising finding that at least one inhibitor of mitosis when combined with an inhibitor of survivin function, such as an inhibitor of survivin phosphorylation, induces apoptosis in cancer cells.

As used herein, the term "survivin function" refers to an activity mediated by or involves survivin. Examples of survivin function include but are not limited to inhibition of apoptosis and phosphorylation.

The inventors tested whether hyperphosphorylation of survivin by increased cdc2 kinase activity affects the efficacy of taxol treatment. Taxol treatment is known to result in cell cycle arrest at mitosis with high cdc2 kinase activity. Surprisingly, the inventors discovered that treatment of human cancer cell lines HeLa and MCF-7 cells with taxol followed 18 hours later with purvalanol A, a highly specific cdc2 kinase inhibitor, resulted in a dramatic enhancement of taxol induced cancer cell death. Reversal of the order of drug administration, purvalanol A first followed by taxol treatment after 18 hour, was without effect. Additionally, substitution of purvalanol A with adriamycin also did not result in enhancement, and cancer cell treatment with purvalanol A alone did not result in cell death. The sequential combination of taxol treatment followed by purvalanol A also resulted in inhibition of cdc2 kinase activity as determined by progressive loss of the mitotic MPM-2 epitope. MPM-2 is a monoclonal antibody that recognizes a large number of mitotic phosphoproteins.

The present invention provides a combination therapy comprising at least one compound that arrests cell mitosis and a survivin antagonist, preferably an antagonist that inhibits survivin phosphorylation. Preferably, the compound that arrests cell mitosis is a taxane, and the antagonist is a CDK1 antagonist. More preferably, the taxane is taxol, and the CDK1 antagonist is purvalanol A. The present invention contemplates a method for the treatment of cancer, inhibiting the growth of tumors, and inducing apoptosis of tumors, preferably malignant cells. More preferably, the treatment comprises a sequential therapy, wherein purvalanol A is administered about 16–24 hours after taxol administration. Most preferably, purvalanol A is administered about 18 hours after taxol treatment.

The present invention is also based in part on the finding that sequential addition of flavopiridol to G2/M-arrested cells suppressed survivin phosphorylation on Thr$^{34}$, and resulted in time- and concentration-dependent loss of survivin expression. This was associated with p53-independent sensitization of tumor cells to adriamycin-induced apoptosis. In a SCID-xenograft model, the sequential combination of adriamycin and flavopiridol suppressed tumor growth and increased overall survival without toxicity, as compared with each treatment alone.

Moreover, the present invention is based in part on the finding that elevated p34$^{cdc2}$ kinase activity during spindle checkpoint activation results in increased survivin expression and cancer cell viability. Removal of this survival mechanism by timed ablation of p34$^{cdc2}$ kinase activity in mitotically-arrested cells caused massive apoptosis, and dramatically enhanced the anti-cancer activity of common microtubule poisons, i.e. taxol, in vivo.

The present invention provides an approach to lowering the therapeutic concentrations of taxane-based chemotherapy (E. K. Rowinsky et al. (1995) *N. Engl. J. Med.* 332: 1004–1014), and improve the treatment of common human cancers.

2. Specific Embodiments

Taxanes

Taxanes are diterpene compounds containing a taxane skeleton. Paclitaxel (taxol) is the first identified compound with a taxane ring. It is isolated from the bark of the pacific yew, Taxus brevifolia. Docetaxel (Taxotere) isolated from the needles of the English yew is also a taxane. Both compounds are effective for the treatment of cancer.

Paclitaxel has been approved by the FDA for the treatment of advanced ovarian cancer and breast cancer after showing outstanding efficacies in the chemotherapy of malignancies particularly in refractory ovarian and breast cancers. Paclitaxel also has been approved by the FDA for treating ovarian, and lung cancers, as well as AIDS-related Kaposi's sarcoma. In recent years, there has been widespread interest in compounds with paclitaxel-like activity such as but not limited to paclitaxel and paclitaxel derivatives and analogs (see, for example, U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506). It has been reported that paclitaxel and its derivatives work against cancer by binding to microtubules in metaphase which stabilizes and prevents the microtubules from depolymerizing. Thus, paclitaxel and its derivatives inhibit mitosis by blocking the cell's ability to break down the mitotic spindle and reorganize into the proper structure for mitosis.

Like paclitaxel, docetaxel prevents the mitotic spindle from being broken down by stabilizing the microtubule bundles. Docetaxel has also shown exceptional clinical results and has been approved for the treatment of breast cancer and nonsmall cell lung cancers that have not responded to other anticancer drugs.

U.S. Pat. No. 6,262,107 discloses water soluble compositions of paclitaxel and docetaxel that may be used for the treatment and diagnosis of tumors. The paclitaxel and docetaxel compounds are formed by conjugating the paclitaxel or docetaxel to a water soluble chelator, polyethylene glycol or polymer such as poly (1-glutamic acid) or poly (1-aspartic acid).

It has been shown that paclitaxel induces prolonged mitotic arrest and elevated levels of mitotic kinase activity, hyperphosphorylation of Bcl-2, an anti-apoptotic protein, and subsequent cell death (Scatena et al. (1998) *J Biol Chem.* 273: 30777–84). This suggests a link between mitotic kinase activation and apotosis.

As discussed in Chadebech et al. (2000 *Int. J. Cancer* 87: 779–786), microtubule damages induced by paclitaxel inhibit proteasome-dependent degradation of cyclin B, resulting in a sustained activation of cyclin B/cdc2 kinase and a cell cycle arrest in mitosis. Chadebech et al. report that paclitaxel up-regulates cdc2 protein level by stimulating cdc2 protein synthesis which is a consequence of paclitaxel induced mitotic arrest. Chadebech et al. show that purvalanol A, a CKI, when added to paclitaxel inhibited the paclitaxel-induced accumulation of cells in mitosis, as well as the activation of cdc2 kinase and up-regulation of cdc2 protein. However, Chadebech et al. do not teach a sequential therapy comprising administering paclitaxel followed by purvalanol A for treating cancer patients.

Taxol therapy is typically used after first-line failure because taxol is toxic and because its side effects and risks of therapy outweigh the benefits until other chemotherapeutic options commonly have been exhausted. The side effects of taxol include anaphylaxis and severe hypersensitivity reactions characterized by dyspnea and hypotension, angiodemia, and generalized urticaria. Side effects also include nausea and vomiting. However, the dose-limiting side effect of taxol is bone marrow suppression. Bone marrow produces blood cells. Taxol can lower the number of white blood cells that guard against infections, and lower the number of platelets that prevent bleeding. Still other side effects include neuropathy, joint and muscle pain or weakness, alopecia (or complete hair loss, which almost always occurs with taxol).

Efforts have been made to reduce the side effects of taxanes. However, few, if any, investigators have reported reduced side effect of taxanes while maintaining its therapeutic effect, or increased therapeutic effect of taxanes while not increasing the side effects.

The present invention uses taxane as a compound that arrests cells in mitosis. As used herein, a compound that "arrests cells in mitosis" refers to a compound that induces cell cycle arrest in mitosis, i.e., the cells do not exit mitosis. Eventually, the cells will escape the block, if the compound is maintained at sufficiently high concentrations. After the cells escape the block, the cells die by apoptosis. The present invention contemplates a method of reducing the dosage of taxane administered to patients with cancer and a method of inducing cancer cell death with a faster and more effective kinetics. The present invention provides a method of treatment comprising administering taxane in combination with a cyclin dependent kinase antagonist to a patient. Surprisingly, the inventors discovered that administration of taxol followed by a cyclin dependent kinase inhibitor (CKI), purvalanol A, enhanced taxol induced cancer cell death. Taxanes that are contemplated by the present invention include, but are not limited to paclitaxel (taxol), docetaxel, and paclitaxel derivatives and analogs. Preferably, the taxane is paclitaxel.

Adriamycin

Adriamycin, also known as doxorubicin, is a cytotoxic anthracycline antibiotic isolated from cultures of *Streptomyces peucetius* var. *caesius*. It consists of a naphthacene-quinone nucleus linked through a glycosidic bond at ring atom 7 to an amino sugar, daunosamine.

Adriamycin is one of the older chemotherapy drugs that have been in use for decades. It is administered intravenously to treat the following cancers: breast, stomach, lymphomas, multiple myeloma, sarcomas, and bone tumors. The cytotoxic effect of adriamycin on malignant cells and its toxic effects on various organs are thought to be related to nucleotide base intercalation and cell membrane lipid binding activities of adriamycin. Adriamycin arrests mitosis by specific intercalation of its planar anthracycline nucleus with the DNA double helix, thereby blocking DNA synthesis. It binds to cell membranes as well as plasma proteins, affecting various cellular functions.

The degree and severity of side effects depend on the amount and schedule of the administration of adriamycin. Some of the significant side effects include soreness of the mouth, diarrhea, low white blood cell count, low platelet count, anemia, heart problems, damage to veins, severe damage to tissues if leaked from the injection site, and red urine due to excretion by the kidneys.

Cyclin Dependent Kinase (CDK) Antagonists

As used herein, the term "cyclin dependent kinase antagonists" encompass any agent that acts as an antagonist of cyclin dependent kinase. Examples of such agents include but are not limited to cyclin dependent kinase inhibitors (CKI), antibodies of CDK, and antisense molecules or CDKs.

Cyclin Dependent Kinase Inhibitors (CKIs)

As described above, CKIs are capable of regulating the cell cycle by inhibiting cyclin dependent kinases. Most CKIs have been shown to inhibit tumor growth in preclinical models by inducing cell cycle arrest or apoptosis, while some have been shown to affect cellular transcription or to cause differentiation.

Cyclin dependent kinase inhibitors can be separated into the following families: purine derivatives, flavopiridols, staurosporines, polysulfates, paullones, and indirubins. The CKI family of purine derivatives include dimethylaminopurine, isopentyladenine, olomoucine, roscovitine, CVT-313, and purvalanol derivatives. The flavopiridol family include flavopiridol and deschloroflavopiridol. Examples of staurosporines include staurosporine, UCN-01, butyrolactone I, 9-hydroellipticine. The CKI polysulfates include suramin and toyocamycin. The CKI paullones include kenpaullone and 10-bromopaullone. Indirubins are active constituent of a Chinese herbal medicine. Examples of indirubins include indirubin and indirubin-3'-monoxime.

However, not all of the inhibitors are specific cyclin dependent kinases. For example, staurosporine, UCN-01, suramin, 6-methylaminopurine, and isopentenyladenine are relatively non-specific protein kinase inhibitors. In contrast, olomoucine, roscovitine, CVT-313, purvalanol derivatives, flavopiridol, butyrolactone I, paullones, and indirubins are more selective for cyclin dependent kinases. Specifically, butyrolactone I, olomoucine, roscovitine, CVT-313, purvalanols, and the paullones are selective for CDK1 (cdc2), CDK2, and CDK5, but are inactive against CDK4 and CDK6. Purvalanol A is fairly selective for CDK1. Flavopiridol, staurosporine, UCN-01 and the indirubins can inhibit CDK4, and flavopiridol has been shown to inhibit CDK6, CDK7, and P-TEFb (containing CDK9). (See http://www.eurekah.com).

The present invention contemplates the use of CKIs in combination with taxane. Preferably, the CKIs are selective for CDK1. More preferably, the present invention uses CKIs such as but not limited to butyrolactone I, olomoucine, roscovitine, CVT-313, purvalanols, and the paullones. Purvalanols of the present invention include but are not limited to purvalanol A and B. The most preferable CKI of the present invention is purvalanol A. The present invention also contemplates the use of nonspecific CKIs in combination with taxane. Preferably the non-specific CKIs include but are not limited to flavopiridol.

Combination Therapy Using Taxanes

The present invention is based in part on the treatment of cancer patients using a combination therapy comprising taxane and an cyclin dependent kinase inhibitor. The use of taxanes in combination with other drugs is routinely practiced by the skilled artisan and such protocols may be modified to practice the claimed invention.

For example, U.S. Pat. No. 6,262,054 discloses a method of inducing tumor cell regression in cancer patients, particularly metastatic breast cancer patients comprising administering edatrexate and a taxane simultaneously or sequentially. The disclosed combination therapy permits the administration of unusually high doses of edatrexate.

U.S. Pat. No. 6,235,776 relates to an improved method of cancer therapy that involves treating a patient with both a paclitaxel derivative (e.g., taxol) and a cyclic GMP-specific phosphodiesterase (PDE) inhibitor. Paclitaxel is administered simultaneously or in succession with a cGMP-specific phosphodiesterase inhibitor, preferably an inhibitor of cGMP-specific phosphodiesterases ("PDE") found in neoplastic cells, of which there are several.

Vermorken (2001 *Int. Bynecol. Cancer* 11: 21–30) describes the integration of paclitaxel and new platinum compounds in the treatment of advanced ovarian cancer. Cisplatin, carboplatin, and nedaplatin have been approved for treatment of patients with ovarian cancer. Vermorken reports that paclitaxel-carboplatin is the preferred regimen in terms of less toxicity and quality of life.

Tominaga et al. (2001 *Gan To Kagaku Ryoho* 28: 965–72) disclose the results of phase I study of docetaxel (TXT) and doxifluridine (5'-DFUR) combination therapy in patients with advanced and recurrent breast cancer. Based on the safety and efficacy of the combined therapy, Tominaga et al. report that the recommended dosage of this regimen is 800 mg/day of 5'-DFUR combined with 60 mg/m$^2$ of TXT.

Bando et al. (2001 *Gan To Kagaku Ryoho* 28: 947–52) disclose the results of combination chemotherapy of carboplatin and docetaxel for advanced non-small cell lung cancer (NSCLC). Bando et al. report that treatment with carboplatin in combination with docetaxel is safe and effective in patients with NSCLC.

Motwani et al. (1999 *Clin Cancer Res* 5: 1876–83) report that flavopiridol enhances paclitaxel-induced apoptosis in human gastric and breast cancer cell lines MKN-74 and MCF-7 only when administered after paclitaxel treatment. Bible et al. (1997 *Cancer Res.* 57: 3375–80) report that that cytotoxic synergy was more pronounced when paclitaxel, cytarabine, topotecan, doxorubicin, or etoposide was administered before flavopiridol rather concomitant with or following flavopiridol administration. Although these references describe combination therapy using paclitaxel and a cyclin dependent kinase inhibitor for in vitro cells, these references do not teach combination therapy for in vivo treatment of patients. More importantly, flavopiridol is not a CKI selective for CDK1.

Schwartz et al. (1999 *Clin Cancer Res* 5(suppl): A122 (abstract)) report that the phase I trial of sequential taxol and flavopiridol therapy is promising and that the recommended phase II dose is 175 mg/m$^2$ taxol, administered over 3 hours on day 1 followed by a 24 hour infusion of 80 mg/m$^2$ flavopiridol, beginning on day 2. Even though Schwartz et al. teach sequential therapy using taxol and flavopiridol, flavopiridol is not a CDK1 selective inhibitor.

Although the prior art discloses combination therapies comprising administering paclitaxel and a second agent simultaneously or sequentially, the prior art does not disclose combination therapies comprising administering taxane followed by a cyclin dependent kinase inhibitor selective for CDK1 (cdc2) in particular, in the time frames, administration protocols, and dosing schedules herein described.

The present invention contemplates a combination therapy comprising administering taxane and a CDK antagonist. In one embodiment, the CDK antagonist is administered about 16–24 hours after taxane administration. Preferably, the taxane is selected from the group consisting of paclitaxel, paclitaxel analogs, docetaxel, and docetaxel analogs, and the CDK antagonist is a CKI selective for CDK1. More preferably, the CKI is selected from the group consisting of butyrolactone I, olomoucine, roscovitine, CVT-313, purvalanols, and the paullones. Most preferably, the taxane is taxol and the CKI is purvalanol A.

Methods of Using Combination Therapy

The present invention is based in part on the finding that treatment of human cancer cell lines with taxol followed about 16–24 hours later with purvalanol A resulted in a dramatic enhancement of taxol induced cancer cell death. The present invention is also based on the finding that treatment of the cells with purvalanol A followed by taxol was without effect. Additionally, the present invention is based on the finding that sequential combination of taxol treatment followed by purvalanol A resulted in inhibition of cdc2 kinase activity. Cdc2 activity mediates survivin phosphorylation. Lack of survivin phosphorylation at $Thr^{34}$ induces cell death at mitosis (O'Connor et al. (2000) *Proc Natl Acad Sci USA* 97(24): 13103–7); and, expression of phosphorylation-defective survivin mutant ($Thr^{34} \rightarrow A$) prevents tumor formation in nude mice (Grossman et al. (2001) *Proc Natl Acad Sci USA* 98: 635–40). Further, the induction of phosphorylation-defective survivin mutant in established melanoma tumors inhibits tumor growth, and increased cell death in vivo (Grossman et al. (2001) *Proc Natl Acad Sci USA* 98: 635–40).

Methods of the invention comprise the administration of the compound that arrests cell mitosis before the administration of the compound that inhibits survivin function. The compound that inhibits survivin function may be administered after the substantial arrest of mitosis or substantial inhibition of cell mitosis. This may comprise a time period of about 12 to about 36 hours or about 16 to about 18 hours.

Accordingly, the present invention provides a method of inhibiting the growth of tumors or neoplasms, inducing tumor regression, and inducing cell death or apoptosis of malignant cells using taxane and a CDK1 antagonist. The present invention contemplates a method of treating cancer and other diseases associated with CDK1 kinase activity, comprising inhibiting CDK1 kinase activity. The present invention provides a combination therapy comprising taxol and a cyclin dependent kinase inhibitor for the treatment of diseases, preferably cancer.

The present invention provides a combination therapy for treating various forms of cancer. As used herein, the term "cancer" includes various types of malignant neoplasms such as carcinomas and sarcomas. Most of these neoplasms invade surrounding tissues, may metastasize to several sites, and are likely to recur after attempted removal and to cause death of the patient unless adequately treated (Stedmans, Stedman's Medical Dictionary, 27$^{th}$ Edition, 1999, Lippincott Williams & Wilkins, Baltimore, Md.). Neoplasm is an abnormal tissue that grows by cellular proliferation more rapidly than normal and continues to grow after the stimuli that initiated the new growth cease (Stedmans, Stedman's Medical Dictionary, 27$^{th}$ Edition, 1999, Lippincott Williams & Wilkins, Baltimore, Md.). Examples of cancer include cancer of the brain, breast, cervix, colon, head & neck, kidney, lung, non-small cell lung, melanoma, mesothelioma, ovary, sarcoma, stomach, and uterus. The term cancer also includes benign tumors.

The present invention contemplates the use of the disclosed combination therapy for the treatment of various cancers that are associated with an increase in survivin expression. Examples of such cancer include but are not limited to lung, colon, breast, pancreas, and prostate. Preferably, the present invention contemplates the use of the combination therapy for the treatment of breast cancer, ovarian cancer, lung cancer, AIDS related-Kaposi's sarcoma, nonsmall cell lung cancer, pancreatic cancer, and other cancers for which taxane is viewed as first and second line of treatment. The present invention also contemplates the use of the combination therapy for tumors with high survivin content.

The combination therapy of the present invention enables the use of reduced dosages of taxane to alleviate side effects in patients with cancer. Moreover, the combination therapy of the present invention induces cancer cell death with a faster and more effective kinetics than either treatment alone, e.g., a synergistic effect is demonstrated.

The combination therapy comprises administering taxane and a CDK1 antagonist. Preferably, the taxane is taxol and the CDK1 antagonist is a CKI. More preferably, the CKI is purvalanol A.

Pharmaceutical Compositions and Methods of Delivery

The present invention provides compositions of taxane and of CKI selective for CDK1 for therapeutic administration. In one embodiment, the composition is administered in the form of a pharmaceutical composition to a patient, subject, or individual in need thereof. In another embodiment, the composition is administered in a safe and effective amount to the subject.

As used herein, a "patient, subject, or individual in need thereof," is a vertebrate having cancer or other diseases. Preferably, the subject is a mammal which includes both human and non-human mammals. Examples of non-human mammals include but are not limited to farm animals, sport animals, and pets. More preferably, the subject is a human.

As used herein, the term "pharmaceutical composition" refers to a composition comprising one or more agents and a pharmaceutically acceptable carrier or component.

As used herein, a "pharmaceutically acceptable" component or carrier is one that is suitable for use with humans and/or animals without undue adverse side effects, such as toxicity, irritation, and allergic response. The carrier or component must be "acceptable" in the sense of being compatible with the active ingredient or agent of the formulation and not deleterious to the subject being treated. A carrier may be a diluent, adjuvant, excipient, or vehicle delivering the one or more agents in the composition. For example, the carrier may be a pharmaceutically acceptable solvent or suspending agent. The carrier may be liquid or solid. Preferably, the carrier is also capable of stabilizing the composition.

Examples of pharmaceutically acceptable carrier include but are not limited to distilled water, physiological saline, Ringer's solution, dextrose solution, and Hank's solution. Pharmaceutical compositions may also include stabilizers, anti-oxidants, colorants, and diluents. In addition, the pharmaceutical composition or formulation may also include other carriers, adjuvants, or nontoxic, nontherapeutic, non-immunogenic stabilizers and the like. Pharmaceutically acceptable carriers are selected such that side effects from the carriers are minimal and that the performance of the active agent is not canceled or inhibited to such an extent that treatment is ineffective. Effective amounts of carrier will be those amounts which are effective to obtain a pharmaceutically acceptable formulation in terms of solubility of components, or biological activity, and the like.

As used herein, a "therapeutically effective amount" is a concentration, quantity, or level of composition that can attain a particular medical end, such as control or destruction of cancer cells or induce apoptosis in tumorigenic cells. It is an amount sufficient to effect a beneficial or desired clinical result, particularly the generation of a noticeable improvement in clinical condition. In terms of clinical response for subjects bearing a neoplastic disease, a therapeutically effective amount is an amount sufficient to palliate, ameliorate, stabilize, reverse or slow progression of the disease, or otherwise reduce pathological consequences of the disease. For example, an amount effective to delay the growth of or to cause a cancer, either a sarcoma to shrink. An effective amount may be given in single, divided, or sequential doses. Preferred quantities and cell ratios for use in an effective amount are given elsewhere in this disclosure.

As used herein, the term "safe and effective amount" refers to the quantity of a induce apoptosis of tumorigenic cells, without undue adverse side effects (such as toxicity, irritation, or allergic response) commensurate with a reasonable benefit/risk ratio when used in the manner of this invention. The specific safe and effective amount or therapeutically effective amount will, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "tumor growth inhibiting amount" of the composition is that amount which is effective to inhibit or slow the growth of a tumor.

As used herein, an amount or a dosage "effective to induce apoptosis" is the amount, dose, or quantity of a composition which is effective to induce cell death.

The amount of taxane, CKI, and carrier to be administered will vary widely depending on the species of the mammal, body weight, and tumor being treated. The dosage administered will vary depending upon known factors, such as the pharmacodynamic characteristics of taxanes and its mode and route of administration, the age, sex, health, metabolic rate, absorptive efficiency, and weight of the subject; the nature and extent of the symptoms; the kind of concurrent treatment; the frequency of treatment; and the effect desired. Generally, the dose should be sufficient to result in slowing, and preferably regressing, the growth of the tumors and also preferably causing complete regression of the cancer. An effective amount of a pharmaceutical agent is that which provides an objectively identifiable improvement as noted by the clinician or other qualified observer. Regression of a tumor in a patient is typically measured with reference to the diameter of a tumor. Decrease in the diameter of a tumor indicates regression. Regression is also indicated by failure of tumors to reoccur.

The compositions comprising taxanes may be administered parenterally, or orally or intraperitoneally in the case of localized regional therapies. The taxane compositions may be administered by intravenous, subcutaneous, intramuscular, or intermedullary injection.

The compositions for parental administration are generally pharmaceutically acceptable, sterile solutions or suspensions which may optionally be prepared as required at the time of use. For the preparation of non-aqueous solutions or suspensions, natural vegetable oils such as olive oil, sesame oil or liquid petroleum or injectible organic esters such as ethyl oleate may be used. The sterile aqueous solutions can consist of a solution of the product in water. The aqueous solutions are suitable for intravenous administration provided the pH is appropriately adjusted and the solution is made isotonic, for example with a sufficient amount of sodium chloride or glucose. Other formulations of taxanes includes liposomal compositions. U.S. Pat. No. 5,424,073, which is herein incorporated by reference, discloses liposome formulations comprising taxanes.

The taxane compositions may be administered in a manner found appropriate by a clinician in generally accepted efficacious dose ranges such as those described in the Physician Desk Reference, 48th Ed. (1994), Publisher Edward R. Barnhart, N.J. ("PDR") for paclitaxel. In general, the taxane is administered intravenously at dosages from about 135 to about 300 mg/m$^2$. In the low dose regime, taxol is administered at doses less than 135 mg/m$^2$ over a period of less than six hours. In the high dose regime, taxol is administered at doses between about 135 and 175 mg/m$^2$ over a period of less than six hours.

For example, the common dose of taxol used to treat patients with ovarian cancer is 135 mg/m$^2$ or 175 mg/m$^2$ administered intravenously over 3 hours every 3 weeks. For patients with breast cancer, the recommended dose of taxol is 175 mg/m$^2$ administered intravenously over 3 hours every 3 weeks. The recommended dose of docetaxel for the treatment of advanced breast cancer is 60 to 100 mg/m$^2$ administered intravenously over 1 hour every 3 weeks.

As with the use of chemotherapeutic drugs, the individual patient will be monitored in a manner deemed appropriate by the treating physician. Typically, no additional drug treatments will occur until, for example, the patient's neutrophil count is at least 1500 cells/mm$^3$. Dosages can also be reduced if severe neutropenia or severe peripheral neuropathy occurs, or if a grade 2 or higher level of mucositis is observed, using the Common Toxicity Criteria of the National Cancer Institute.

The compositions comprising cyclin dependent kinase inhibitor of the present invention may be adapted for oral, rectal, vaginal, parenteral, intra-muscular, intra-peritoneal, sub-cutaneous intravenous, nasal or buccal routes of administration. For oral administration, particular use is made of compressed tablets, pills, tablets, gellules, drops and capsules. These compositions advantageously contain from 1 to 100 mg, and preferably from 10 to 40 mg, of active ingredient per dose. Other forms of administration comprise solutions which can be injected intravenously, subcutaneously, intramedullarly or intramuscularly, and which are prepared from sterile or sterilisable solutions. They can also be in the form of suppositories, pessaries, suspensions, emulsions, lotions, ointments, creams, gels and sprays.

The purpose of combination therapy is to increase the therapeutic effects of taxol without increasing its side effects. Accordingly, when paclitaxel is administered with a second agent, the traditionally recommended dose range of paclitaxel may be decreased while its therapeutic effects are maintained and its side effects are attenuated in the presence of the second agent. Alternatively, the traditionally recommended dose range for paclitaxel is used with the second agent which improves paclitaxel's activity without increasing its side effects. Typically, in a low dose regime, paclitaxel is administered at doses less than 135 mg/m$^2$ over a period of less than six hours. In a high dose regime, paclitaxel is administered at doses between about 135 and 175 mg/m$^2$ over a period of less than six hours. Preferably, the taxane is administered at a low dose and a CDK1 antagonist is administered subsequently.

The combination therapy described here may be administered with taxane by itself or in combination with other therapeutic agents, including but not limited to, immunosuppressive agents, potentiators and side-effect relieving agents. Likewise, the CDK1 antagonist may be administered by itself or in combination with other therapeutic agents.

Kits

The present invention also includes kits useful for the treatment of cancer. The kits of the present invention comprise one or more containers containing compositions comprising a therapeutically effective amount of a taxane and a CDK1 antagonist. Such kits can further include, if desired, one or more of various conventional pharmaceutical kit components, such as, for example, containers with one or more pharmaceutically acceptable carriers, additional containers such as vials and tubes, etc., as will be readily apparent to those skilled in the art. Printed instructions, either as inserts or as labels, indicating quantities of the components to be administered, guidelines for administration, and/or guidelines for mixing the components, can also be included in the kit.

In light of the foregoing general discussion, the specific examples presented below are illustrative only and are not intended to limit the scope of the invention. Other generic and specific configurations will be apparent to those persons skilled in the art.

EXAMPLES

Example 1

Sequential Therapy: Taxol Followed by Purvalanol A

Cervical carcinoma HeLa (functionally inactivated p53) cells or breast carcinoma MCF-7 (wild type p53) cells were plated at 50–60% confluency in C-6 wells. Cells were treated with taxol at 0.2 $\mu$M for 0 to 32 hours in complete media. By DNA content analysis and flow cytometry this results in uniform M arrest of both cell types and virtually no apoptosis by looking at the hypodiploid cell fraction.

Figure 1:
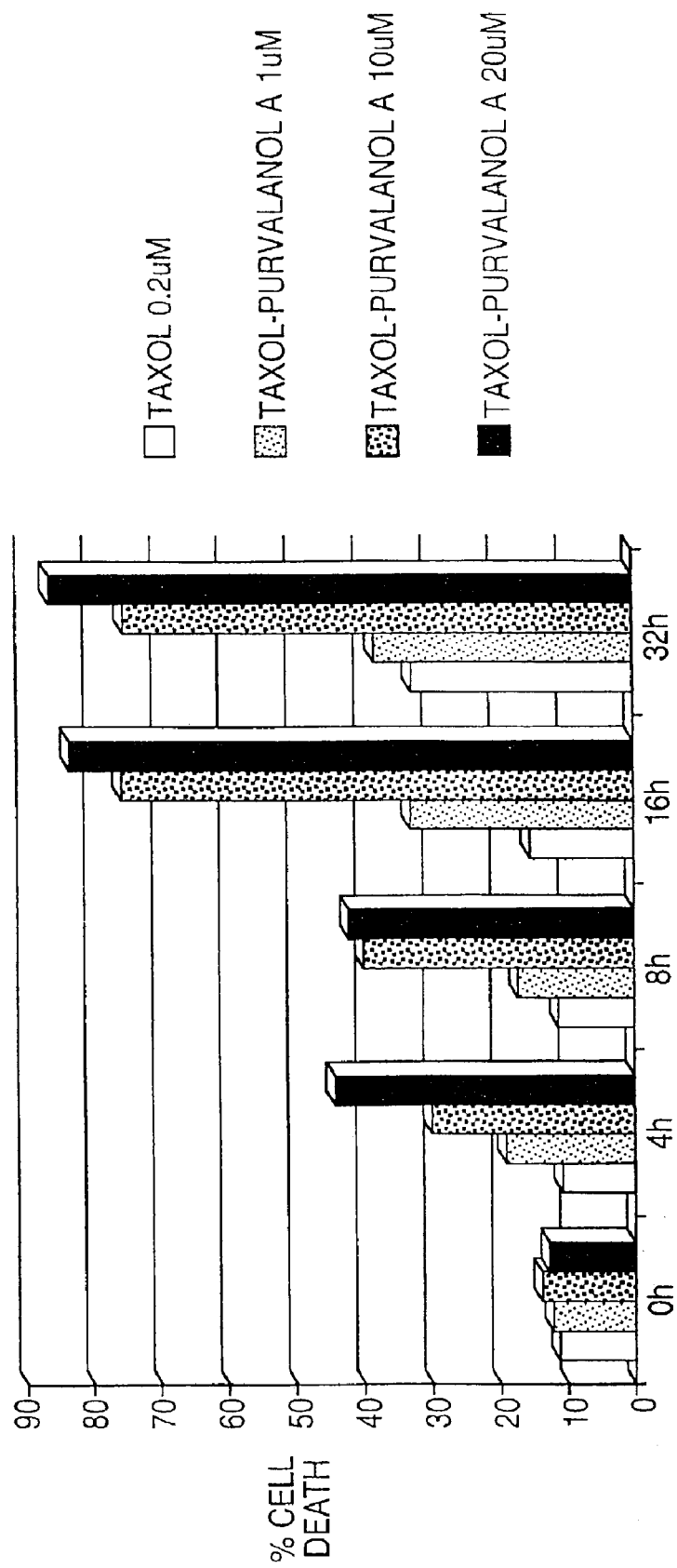
FIG. 1 shows the effect of the taxol-purvalanol A sequential therapy in HeLa cells. The sequential therapy increases cell death.

After 4, 8, 16, and 32 hours of incubation, without removing taxol from the wells, purvalanol A was added at three increasing concentrations, 1, 10 and 20 uM (FIG. 1). A control was performed with addition of purvalanol A at the 0-h time point.

Figure 2:
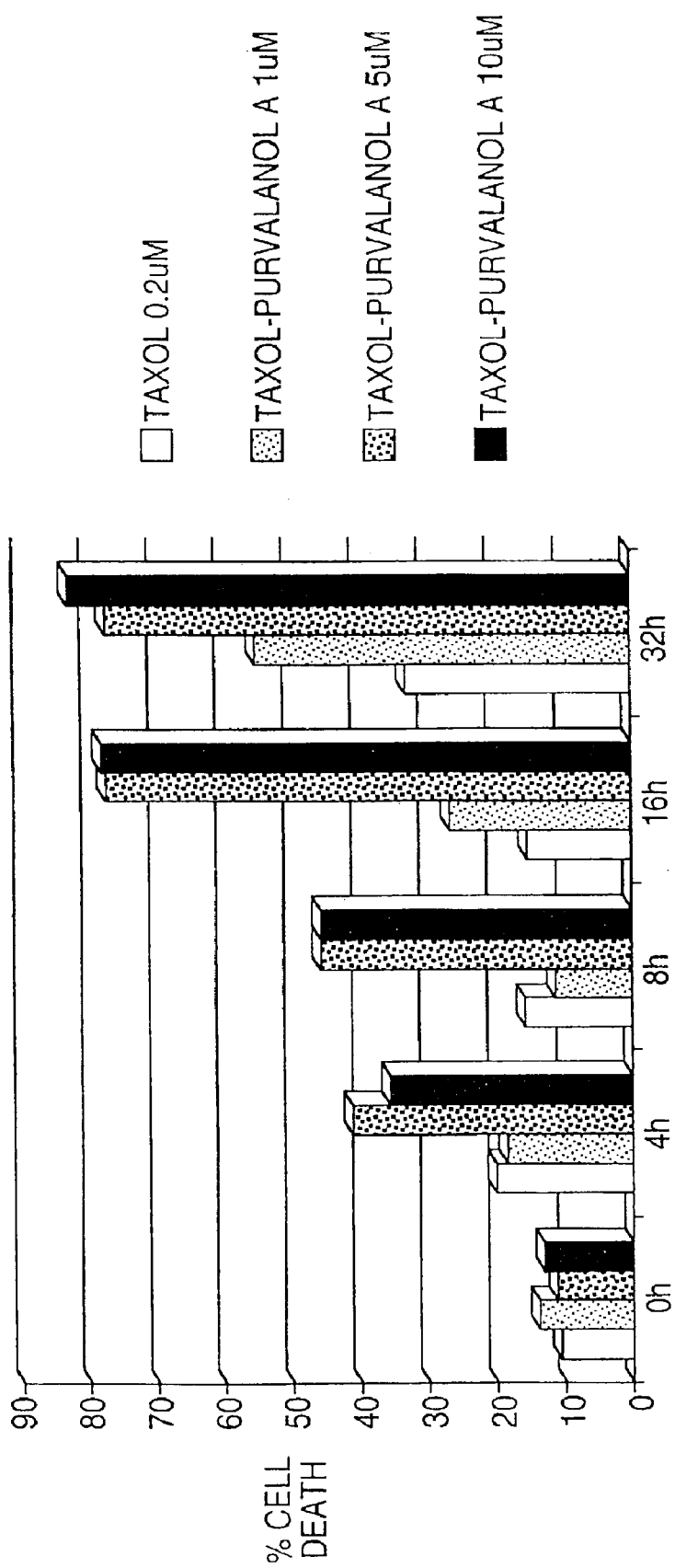
FIG. 2 shows the effect of the taxol-purvalanol A sequential therapy in MCF-7 cells. The sequential therapy increases cell death.

The cell populations were harvested at increasing time intervals from the 0-h time point or corresponding to the addition of purvalanol A. Apoptosis was analyzed by DNA content analysis and flow cytometry (DAPI staining). A difference in the cultures was evident microscopically: the combination treatment revealed cells that were still large and rounded as after taxol treatment, but the morphology was different and the cells began to shrink and exhibited fragmented nuclei after addition of purvalanol A. In HeLa cells, there were ~10% hypodiploid cells after taxol treatment alone. In combination with 20 uM purvalanol A, there was 40% apoptosis at 8 h and ~90% apoptosis 16 h after purvalanol A addition (FIG. 1). With MCF-7 cells, the efficacy was nearly identical (FIG. 2). The effect of purvalanol A was dose dependent with increasing concentrations.

Figure 3:
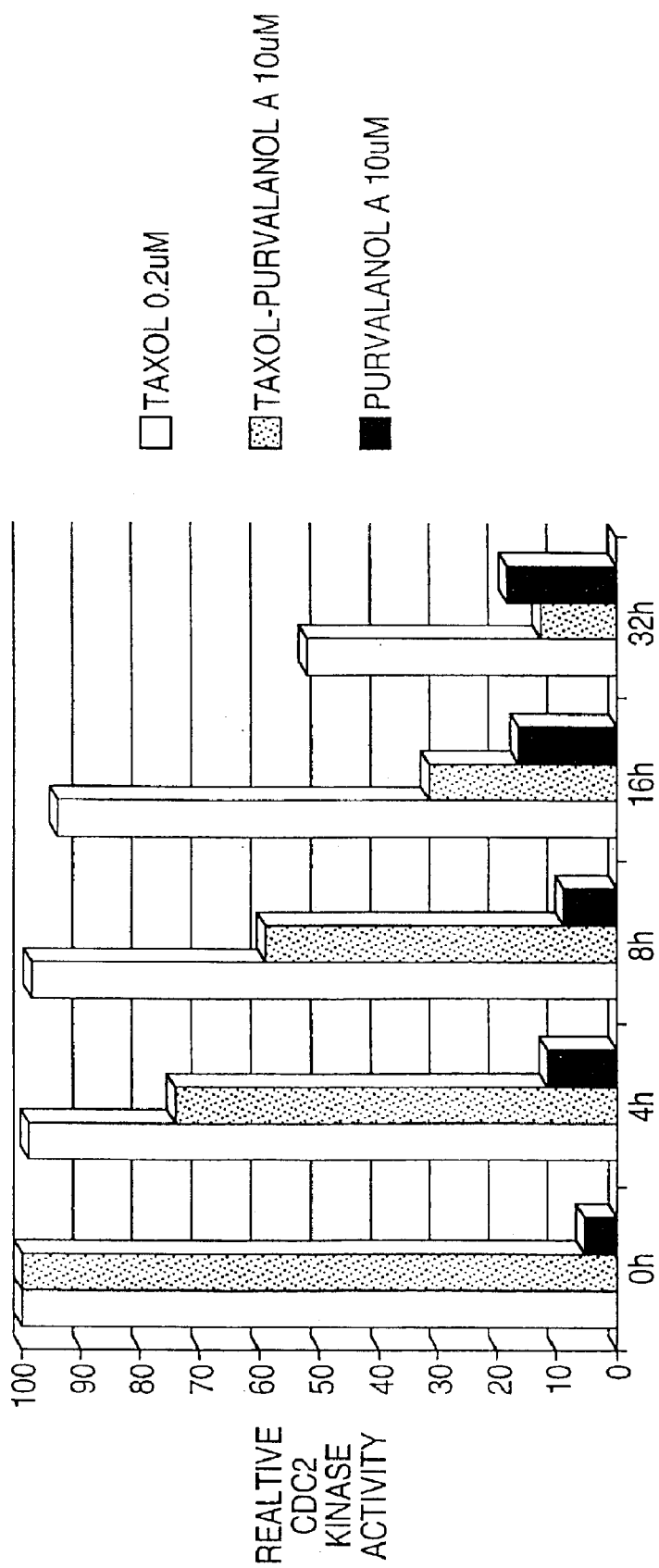
FIG. 3 shows the effect of the taxol-purvalanol A sequential therapy on cdc2 kinase activity.

Kinase activity was monitored by looking at expression of the MPM-2 epitope. MPM-2 is a monoclonal antibody that recognizes a large number of mitotic phosphoproteins. It was found that 70–80% inhibition of kinase activity correlated with induction of massive apoptosis 16 h after addition of purvalanol A in taxol-treated cells (FIG. 3).

Both HeLa and MCF-7 express normal levels of survivin.

Example 2

Sequential Therapy: Purvalanol A Followed by Taxol

Cervical carcinoma HeLa (functionally inactivated p53) cells or breast carcinoma MCF-7 (wild type p53) cells were plated at 50–60% confluency in C-6 wells. Cells were treated with purvalanol A at 1, 10, 20 uM followed by 0.2 uM taxol at 0, 4, 8, 16, and 32 hours later.

Figure 4:
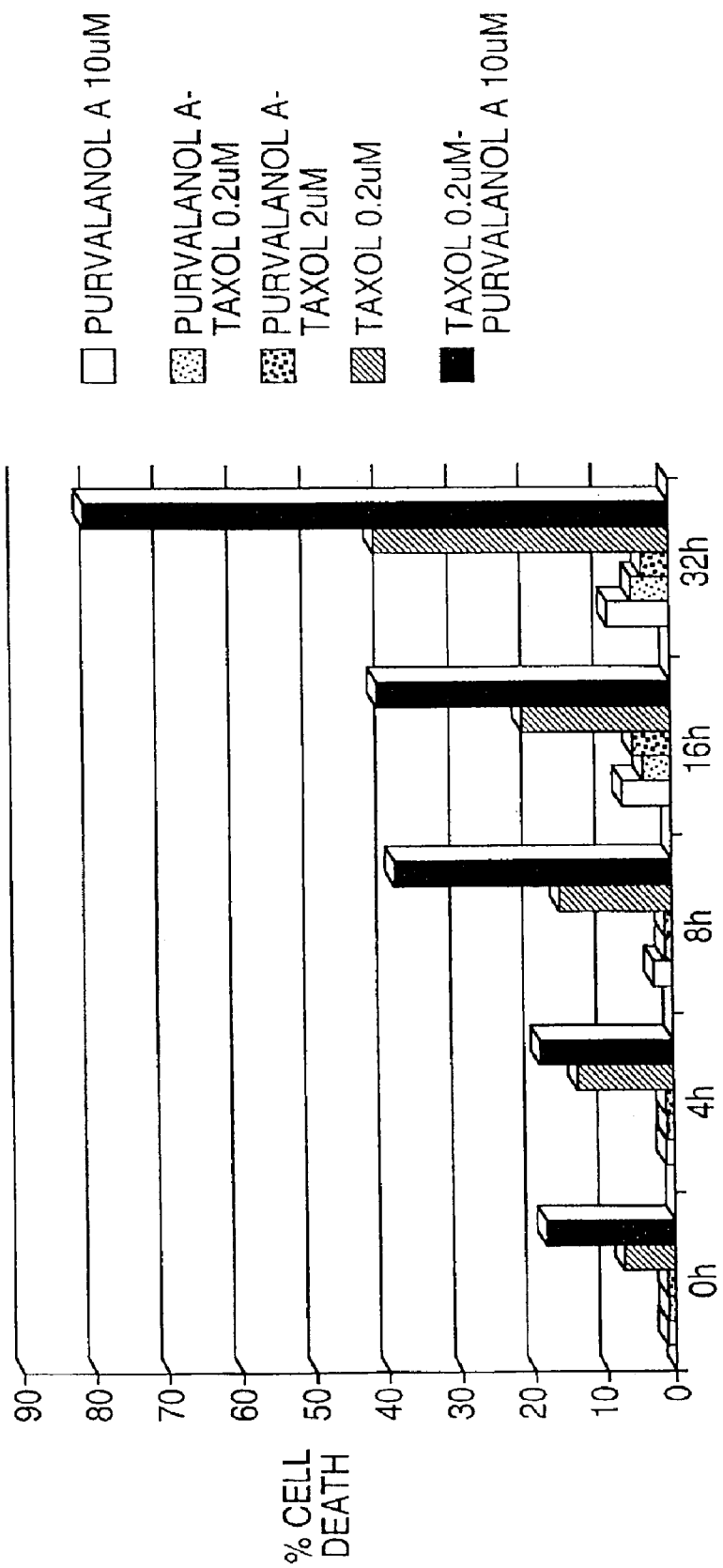
FIG. 4 shows the effect of the reversed sequential therapy in HeLa cells. Purvalanol A treatment followed by taxol has little effect on the cells.

FIG. 4 shows the results of reversed drug therapy with HeLa Cells. When the treatment schedule was reversed, purvalanol A first followed by taxol, no effect was observed, other than that seen with taxol alone. Purvalanol A alone at the same concentrations induced strong M arrest but, no apoptosis at all.

Example 3

Sequential Therapy: Taxol Followed by Adriamycin

The same experiment as in Example 1 was performed; however purvalanol A was substituted with adriamycin at 100 nM and 200 nM. Controls were performed with taxol alone and taxol and purvalanol A at 10 uM.

Figure 5:
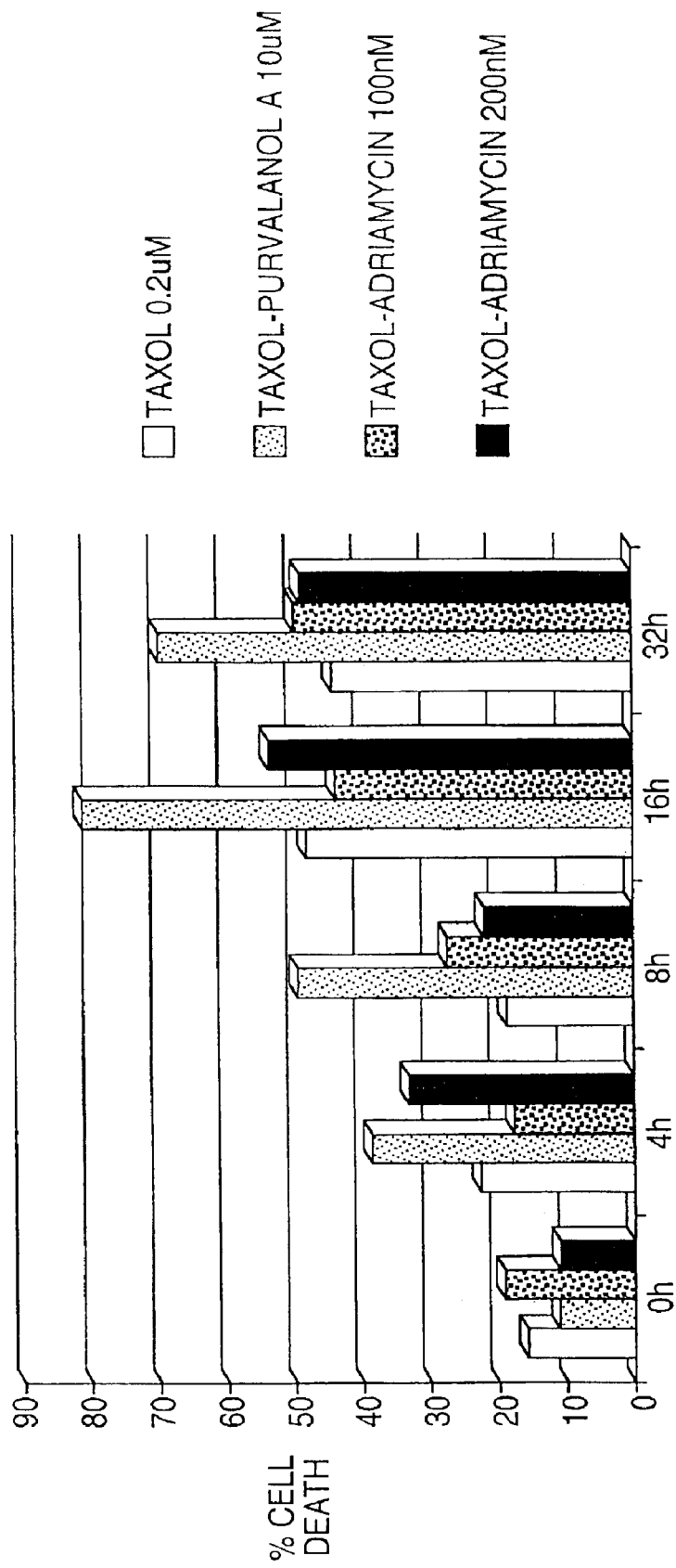
FIG. 5 shows the effect of taxol-adriamycin sequential therapy in MCF-7 cells. Substituting adriamycin for purvalanol A does not enhance taxol-induced cell death.

FIG. 5 shows the results of substituting adriamycin for purvalanol A with MCF-7 cells. The substitution did not enhance taxol-induced cell death as compared with each treatment alone.

Example 4

Sequential Therapy: Vincristine Followed by Purvalanol A

The same experiment as in Example 1 was performed; however vincristine at 10 nM and 100 nM was substituted for taxol, and purvalanol A was administered at 10 uM. Controls were performed with vincristine alone at 100 nM.

Figure 6:
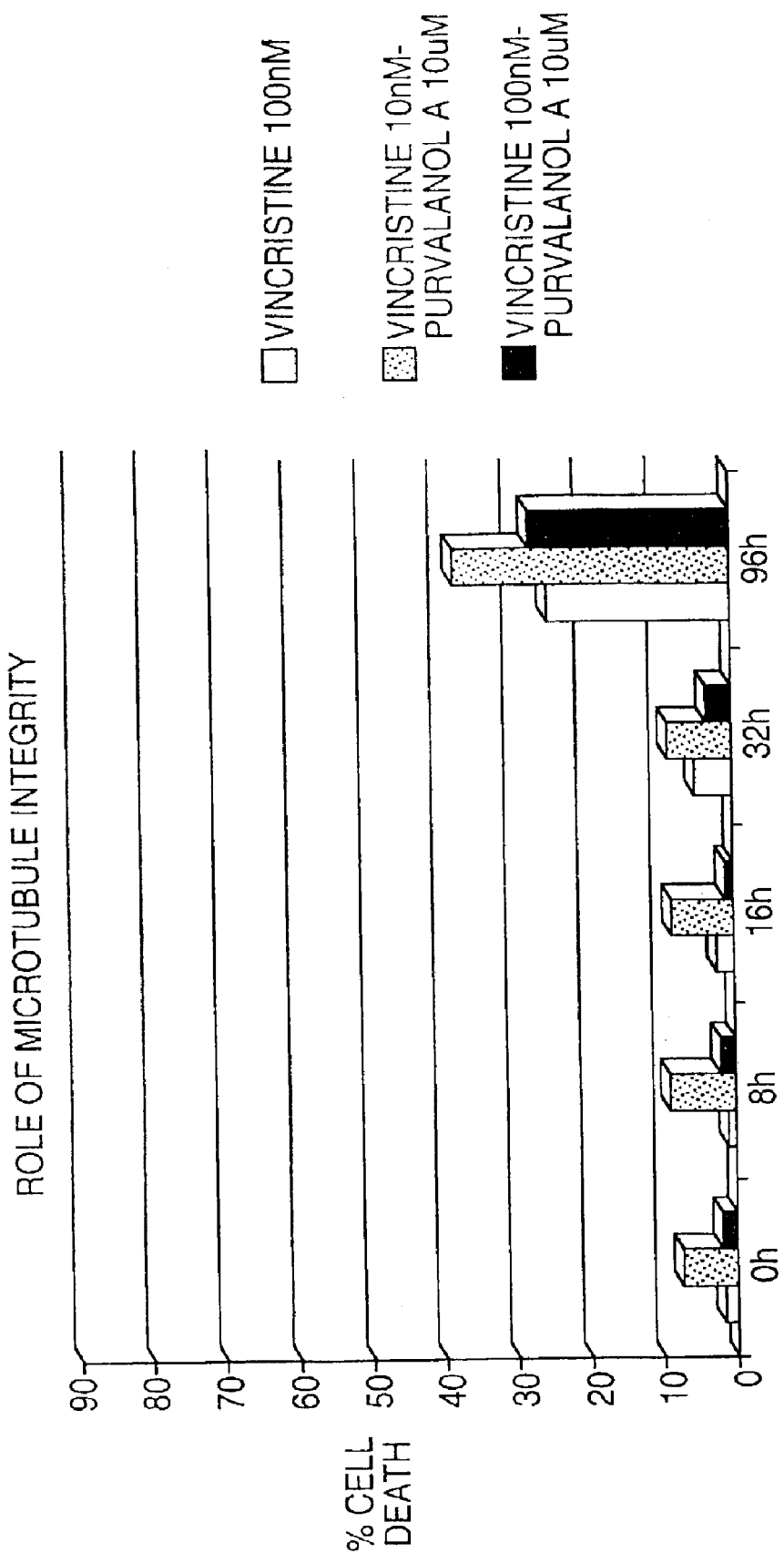
FIG. 6 shows the effect of vincristine-purvalanol A sequential therapy in MCF-7 cells. Purvalanol A does not synergize with vincristine treatment.

FIG. 6 shows the results of using vincristine with purvalanol A. As shown, purvalanol A did not synergize with vincristine treatment. Unlike taxol, vincristine depolymerizes microtubules. Accordingly, microtubule integrity may be essential for the method of treatment of the present invention.

Figure 7:
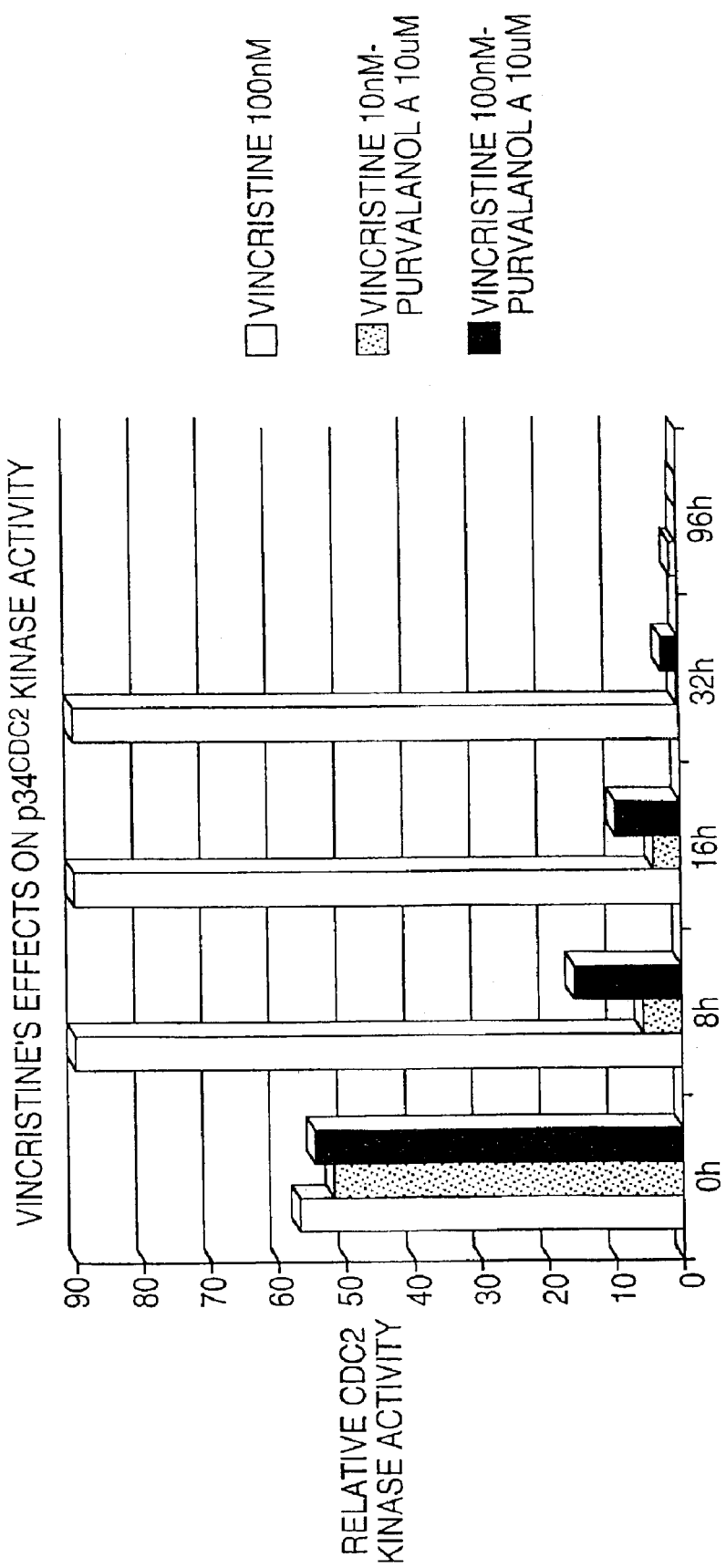
FIG. 7 shows the effect of vincristine-purvalanol A sequential therapy on cdc2 kinase activity in MCF-7 cells. Vincristine, like taxol, induces cdc2 kinase activity in MCF-7 cells.
Figure 8:
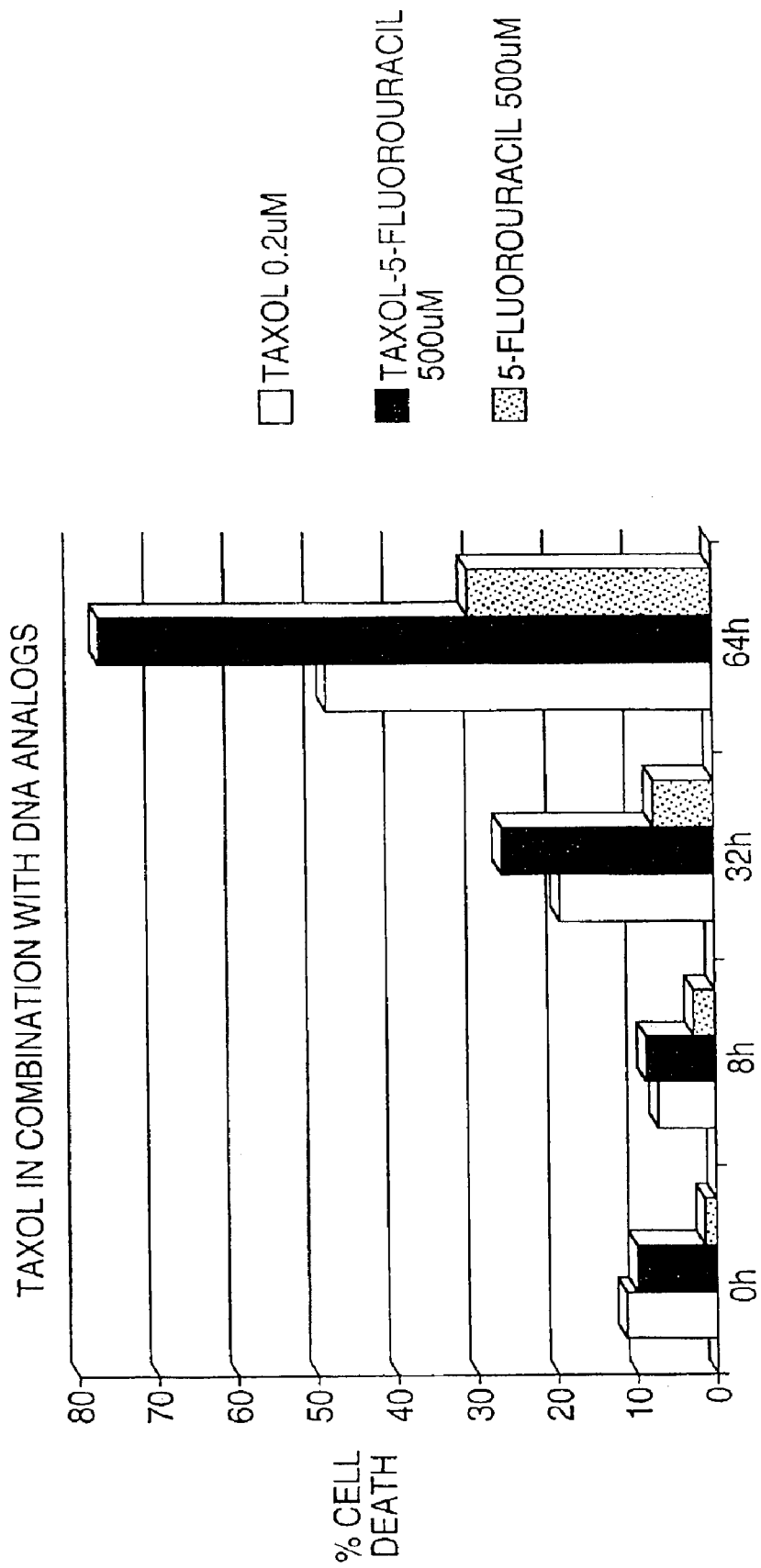
FIG. 8 shows the effect of taxol-5-fluorouracil sequential therapy on MCF-7 cells. The sequential therapy increases cell death.

FIG. 7 shows that vincristine, like taxol, induces cdc2 kinase activity in MCF-7 cells.

Example 5

Sequential Therapy: Comparing Various CKIs

The same experiment as in Example 1 was performed; however, alsterpaullone at 20 uM, flavopiridol at 250 nM, and olomoucine at 400 nM were substituted for purvalanol A.

Figure 9:
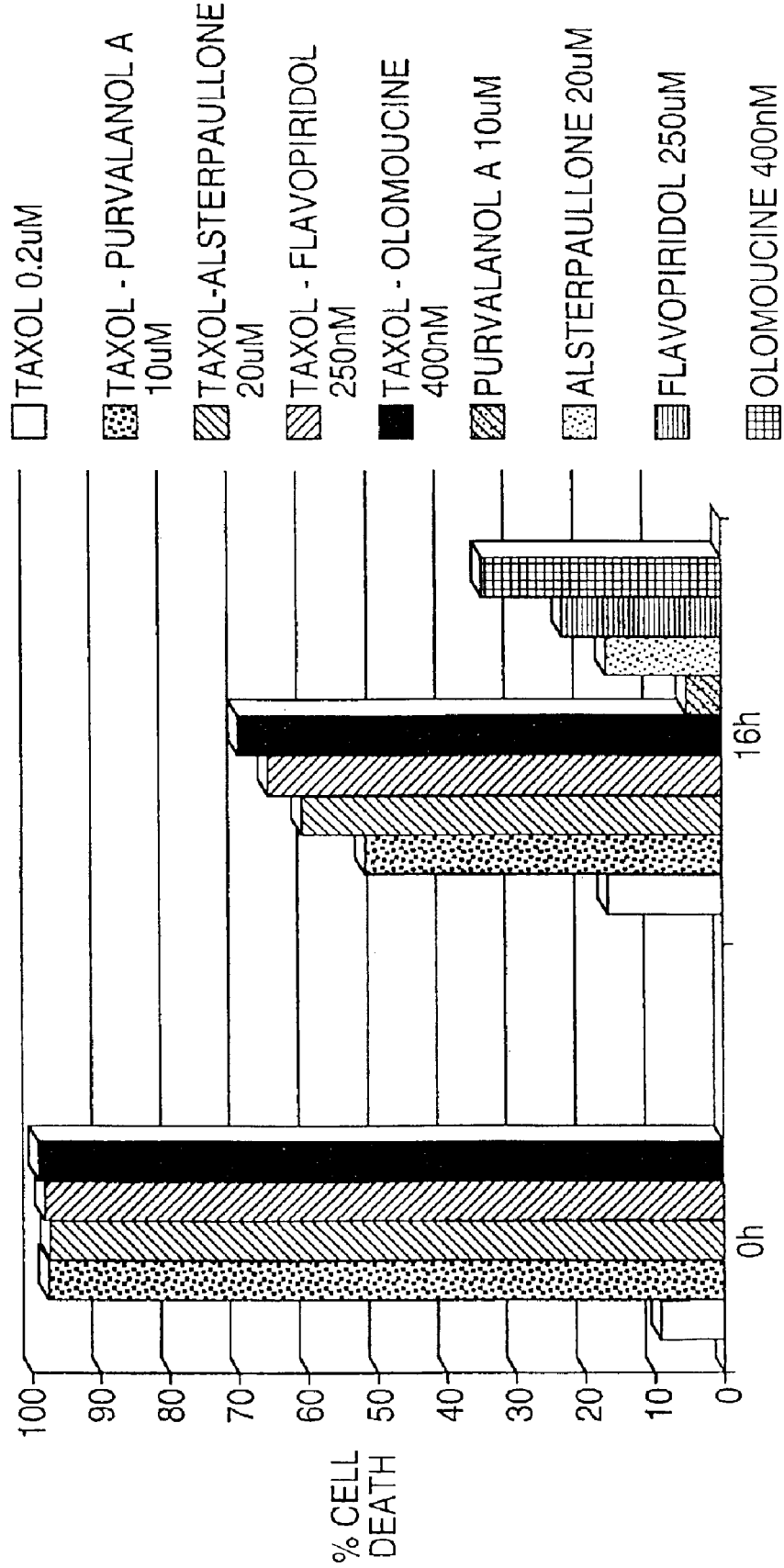
FIG. 9 shows the effect of taxol and various CKIs in HeLa cells. These agents also synergize with taxol.

FIG. 9 shows the results using the different CKIs. These agents also synergize with taxol. However, since they are less specific for inhibition of p34$^{cdc2}$ kinase activity than purvalanol A, they induce a higher background of apoptosis by themselves (FIG. 9), i.e., they inhibit additional kinases.

FIG. 10 shows the effect of these CKIs on p34$^{cdc2}$ kinase activity.

Example 6

In Vivo Xenograft Mouse Model

Figure 11A:
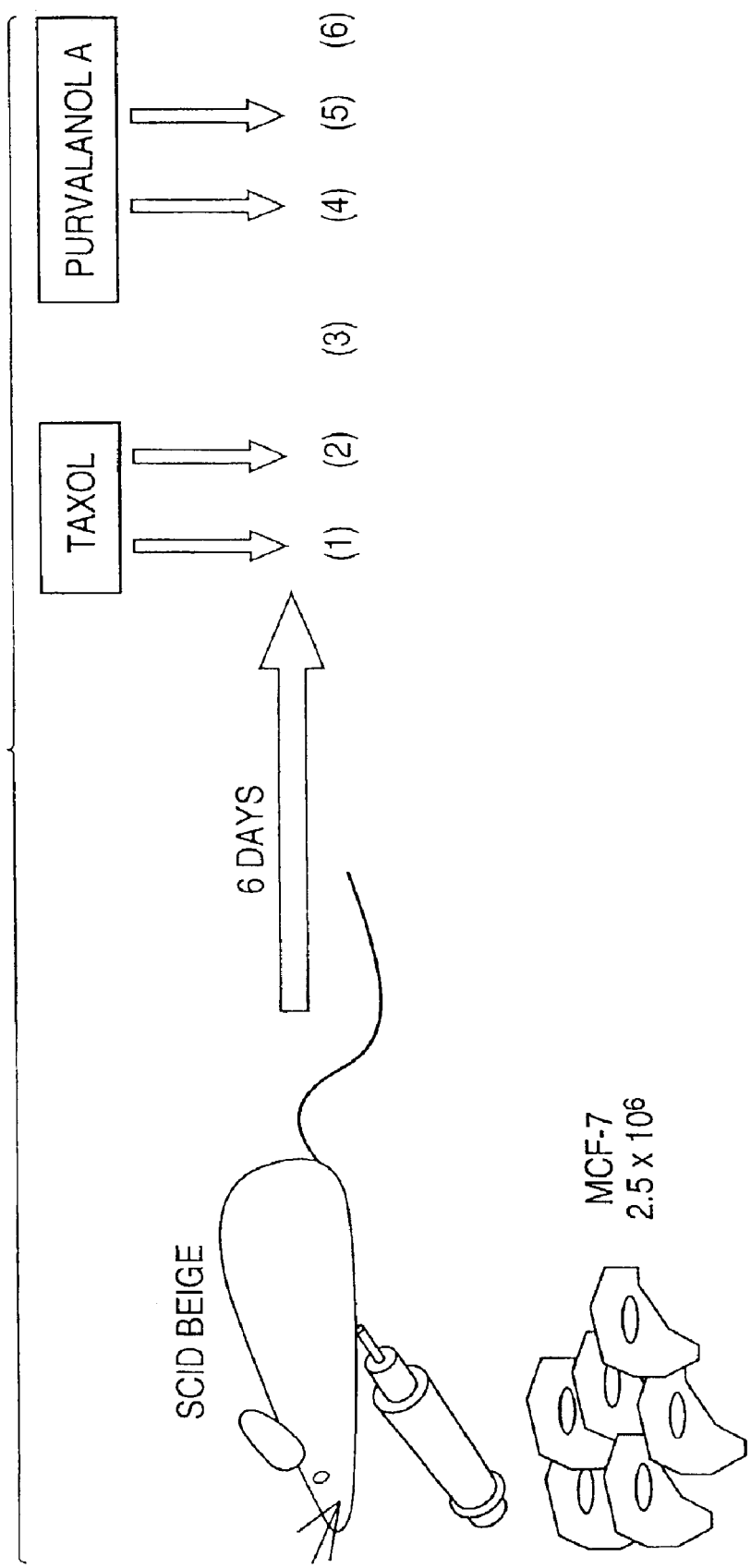

Forty 4–6 week old SCID Beige Mice (Taconic Laboratories) were allocated into five experimental groups of eight. All mice were then subjected to a subcutaneous injection of 2.5×10$^6$ MCF-7 (human breast cancer) cells. Five days after tumor cell injection, primary tumors were measured in three dimensions with a digital caliper (VWR Scientific). Day 1 symbolized the first day of therapeutic injections applied intra-peritoneally (IP). The injection protocol (FIG. 11A) was as follows: Day 1(inject), Day 2 (inject), Day 3 (oft), Day 4(inject), and Day 5(inject). For control mice, all injections solely comprised of ~200 $\mu$l solubilizing solution: 0.5% DMSO and 15% Cremophore EL/EtOH in PBS. For taxol treated mice (2.5 mg/kg and 5.0 mg/kg), IP injections of drug occurred on all treatment days (Days 1, 2, 4 and 5).

Figure 11B:
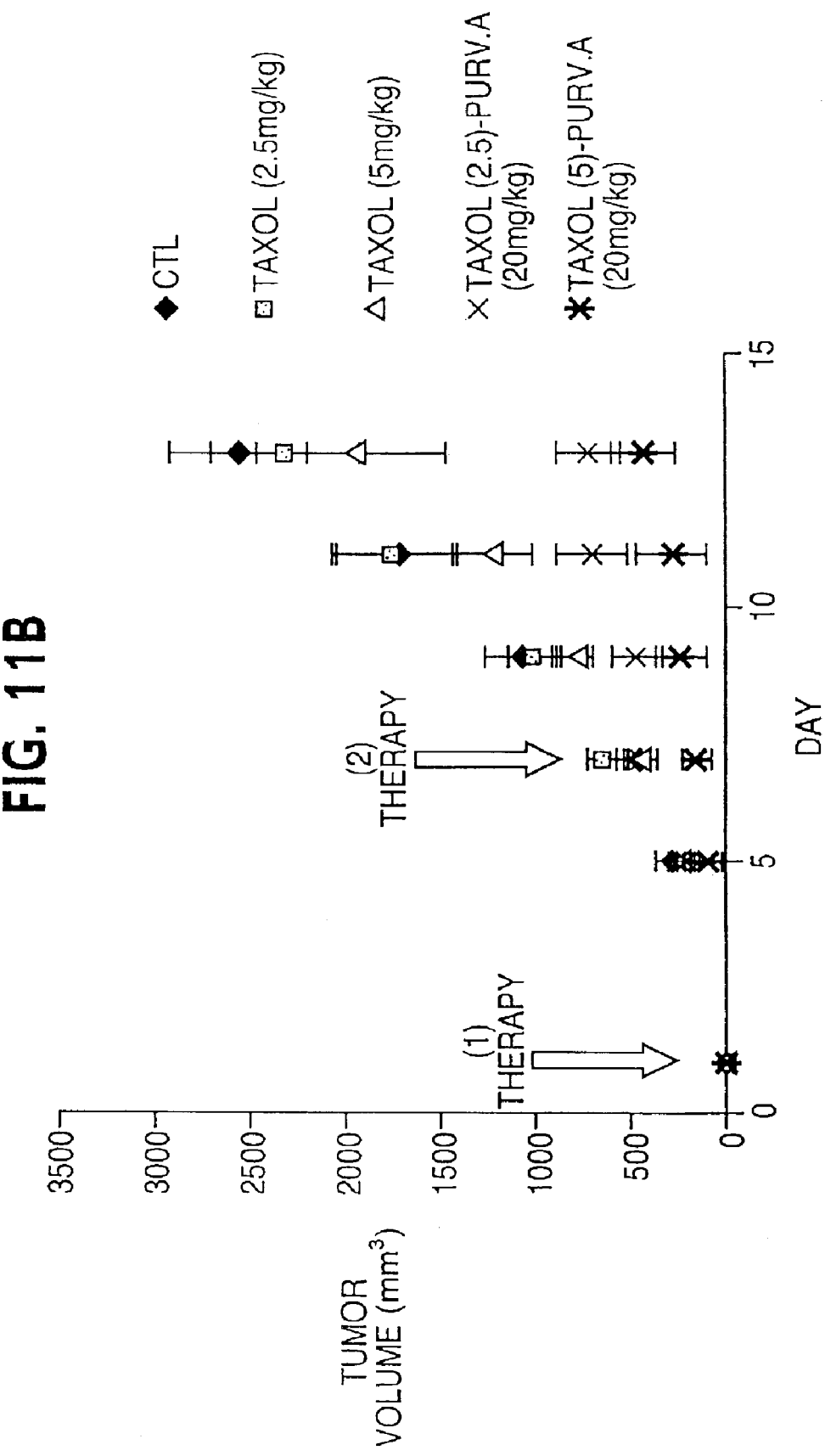

For sequential taxol-purvalanol A therapy, taxol was injected IP on Days 1 and 2 followed by purvalanol A injections on Day 4 and 5 (FIG. 11B). Following the first round of therapy, one day was given off, and the regimen was reinitiated on Day 7 and terminated on Day 13. Measurements were taken at indicated time intervals and graphed accordingly. For survival curve data (FIG. 11C), mice tumors were measured every other day after completion of both therapeutic regimens. Once tumor exceeded a critical volume of 3000 mm$^3$, the mouse was terminated and denoted as death in the survival curve.

FIG. 11B shows that sequential taxol-purvalanol A therapy inhibited the growth of the tumor in SCID mice injected with cancer cells as compared to control mice (CTL). On Day 13, the tumor volume was below 1000 mm$^3$.

FIG. 11C shows that sequential taxol-purvalanol A therapy increased survival rate of SCID mice injected with cancer cells.

Example 7

Timed (G2/M) Ablation of Survivin Phosphorylation by Flavopiridol Enhances Anti-Cancer Therapy In this study, the cyclin-dependent kinase inhibitor, flavopiridol, was used to interfere with p34$^{cdc2}$ phosphorylation of survivin during checkpoint activation induced by anti-cancer treatments, in vitro and in a xenograft breast cancer model, in vivo.

Exposure of breast carcinoma MCF-7 or cervical carcinoma HeLa cells to adriamycin, cis-platin or ultraviolet B (UVB) resulted in G2/M cell cycle arrest and a 4 to-5-fold increased survivin expression, which was independent of de novo gene transcription. Residual p34$^{cdc2}$ kinase activity in adriamycin-, but not UVB-treated cells was sufficient to phosphorylate survivin on Thr$^{34}$. Sequential addition of flavopiridol to G2/M-arrested cells suppressed survivin phosphorylation on Thr$^{34}$, and resulted in time- and concentration-dependent loss of survivin expression. This was associated with p53-independent sensitization of tumor cells to adriamycin-induced apoptosis. In a SCID-xenograft model, the sequential combination of adriamycin and flavopiridol suppressed tumor growth and increased overall survival without toxicity, as compared with each treatment alone.

Targeted suppression of p34$^{cdc2}$ kinase during G2/M arrest results in loss of survivin expression and sensitization of tumor cells to chemotherapy-induced apoptosis. Timed administration of p34$^{cdc2}$ kinase inhibitors may ablate the survivin viability checkpoint and improve the efficacy of common anti-cancer regimens.

Methods

Cell Cultures, Proteins and Antibodies: Breast carcinoma MCF-7 and cervical carcinoma HeLa cells (American Type Culture Collection, Manassas, Va.) were maintained in culture according to the manufacturer's specifications. For treatment with genotoxic agents, HeLa or MCF-7 cells were incubated with vehicle (DMSO) or taxol (2 μM, Sigma Chemical Co., St. Louis, Mo.), adriamycin (100 nM, Sigma), cis-platin (3 μM, Sigma) or subjected to ultraviolet B (UVB) irradiation at 50 or 300 J/m$^2$. In some experiments, HeLa or MCF-7 treated with taxol, adriamycin or UVB as described above were incubated with inhibitors of transcription (actinomycin D, 1 μg/ml) or translation (cycloheximide, 2 mg/ml) before determination of protein expression by Western blotting. To target survivin phosphorylation by p34$^{cdc2}$ (D. S. O'Connor et al. (2000) Proc. Natl. Acad. Sci. USA 97: 13103–7), HeLa or MCF-7 cells were incubated with increasing concentrations of vehicle or the cyclin dependent kinase inhibitor, flavopiridol (1–1000 nM) for 12–96 h at 37° C., before analysis of protein expression by Western blotting or apoptosis (see below). Wild type survivin or a phosphorylation-defective survivin(T34A) mutant were expressed in E. coli as glutathione-S transferase (GST) fusion proteins, as described (D. S. O'Connor et al. (2000) Proc. Natl. Acad. Sci. USA 97: 13103–7). A replication-deficient adenovirus encoding wild type survivin (pAd-Survivin) or control encoding Green Fluorescence Protein (pAd-GFP) was generated using the pAd-Easy system as described previously (M. Mesri et al. (2001) J. Clin. Invest. 108: 981–90), and propagated in HEK293 cells with purification by CsCl banding. With this protocol, no replication-competent adenovirus particles were generated (M. Mesri et al. (2001) J. Clin. Invest. 108: 981–90). Antibodies to p34$^{cdc2}$ or bcl-2 were obtained from Pharmingen (San Diego, Calif.) and R&D, respectively. An antibody to β-actin was from Sigma and antibodies to MPM-2 mitotic phosphoproteins was from Upstate Biotechnology (Lake Placid, N.Y.). Affinity purified antibodies to wild type survivin or Thr$^{34}$ phosphorylated survivin (α-survivin T34*) were described previously (D. S. O'Connor et al. (2000) Proc. Natl. Acad. Sci. USA 97: 13103–7).

Western Blotting, Northern Hybridization, Immunoprecipitation and Kinase Assay: Analysis of protein expression by Western blotting and enhanced chemiluminscence was carried out as described (D. S. O'Connor et al. (2000) Proc. Natl. Acad. Sci. USA 97: 13103–7). In some experiments, total RNA was extracted from MCF-7 cells at various time intervals after adriamycin treatment, and hybridized with 32 P-labeled survivin cDNA as described previously. Radioactive bands were detected by autoradiography. Immunoprecipitation of survivin or p34$^{cdc2}$ from HeLa or MCF-7 detergent-solubilized cell extracts was carried out as described (D. S. O'Connor et al. (2000) Proc. Natl. Acad. Sci. USA 97: 13103–7). In some experiments, p34$^{cdc2}$ immunoprecipitated from vehicle or flavopiridol-treated cells was incubated with histone H1 (1 μg), wild type survivin or survivin (T34A) (6 μg) in kinase buffer containing 10 μCi of γ-$^{32}$P-ATP (Amersham) and processed in a kinase assay, as described (D. S. O'Connor et al. (2000) Proc. Natl. Acad. Sci. USA 97: 13103–7). In other experiments, samples were transferred to nylon membranes and analyzed by Western blotting with antibodies to p34$^{cdc2}$ (1 μg/ml), survivin (2 μg/ml), or survivinT34* (5 μg/ml).

Survivin Promoter-Luciferase Reporter Expression: Survivin promoter activity in MCF-7 cells (1–2×10$^5$/well) treated with taxol, adriamycin or UVB irradiation (50–300 J/m$^2$) was carried out using a minimal survivin promoter upstream of a luciferase reporter gene (pLuc-cyc1.2), as described (F. Li et al. (1998) J. Cell Sci. 396: 580–4). Luciferase activity was determined after 0–24 h incubation at 37° C. on a Lumat luminometer (LB9510), and normalized to β-galactosidase activity used as an internal control.

MPM-2 Mitotic Phosphoepitope Expression: For detection of mitotic phosphoproteins (D. D. Vandre et al. (1989) J. Cell Sci. 94: 245–58), MCF-7 cells (1–2×10$^5$ cells/60 mm dish) were treated with taxol (2 μM), adriamycin (100 nM), 50 or 300 J/m$^2$ UVB irradiation and cultured for 0, 8, 16, 24 or 36 h at 37° C. Cells were fixed in 70% ethanol, labeled with MPM-2 antibody (6 μg/ml) followed by addition of goat anti-mouse FITC (Boehringer Mannheim) for 1 h at 22°

C. in the presence of 5 μg/ml propidium iodide (PI) containing 50 μg/ml RNase A. Samples were analyzed on a FACScan (Becton Dickinson, Mountain View, Calif.), using CellQuest software.

Determination of Apoptosis: HeLa or MCF-7 cells treated with vehicle, flavopiridol or the various combinations of genotoxic stresses described above were harvested at various time intervals at 37° C., and analyzed for DNA content by P.I. content and flow cytometry, as described (F. Li et al. (1999) *Nat. Cell Biol.* 1: 461–6).

Xenograft Breast Cancer Model: All experiments involving animals were approved by the Institutional Animal Care and Use Committee. Five-week old female CB.17 SCID/beige mice (Taconic Farms, Germantown, N.Y.) were adapted, and MCF-7 xenografts were developed as described previously (M. Mesri et al. (2001) *J. Clin. Invest.* 108: 981–90). Each mouse received $2.5 \times 10^6$ exponentially growing MCF-7 cells (in 100 μl sterile 1×PBS) s.c. in the right flank area. Tumors became palpable (25–75 mm$^3$) within 5 days of tumor cell injection, after which groups of five animals were randomized and assigned to different treatment groups. Tumor size was determined by the product of two perpendicular diameters and the height above the skin surface every other day and expressed as tumor volume in cubic millimeters. Animals were sacrificed once their tumor burden reached 3000 mm$^3$. Animals were injected i.p. with adriamycin alone (1.0, 2.0, 4.0 mg/kg), flavopiridol alone (15 mg/kg) or the sequential combination of adriamycin/flavopiridol for two consecutive days each divided by a day with no treatment. For single agent treatment, vehicle was given in place of adriamycin or flavopiridol with the same schedule. Each complete cycle was separated by 2 d without treatment.

Statistical Analysis: All in vitro experiments were repeated at least three times unless otherwise indicated. For in vivo studies, each X value (time) shows the fraction still alive. Survival fractions using the product limit or Kaplan-Meier method were calculated. The survival curves were compared using the logrank test. This test generates a P value testing the null hypothesis that the survival curves are identical in the overall populations.

Results

Figure 12A:
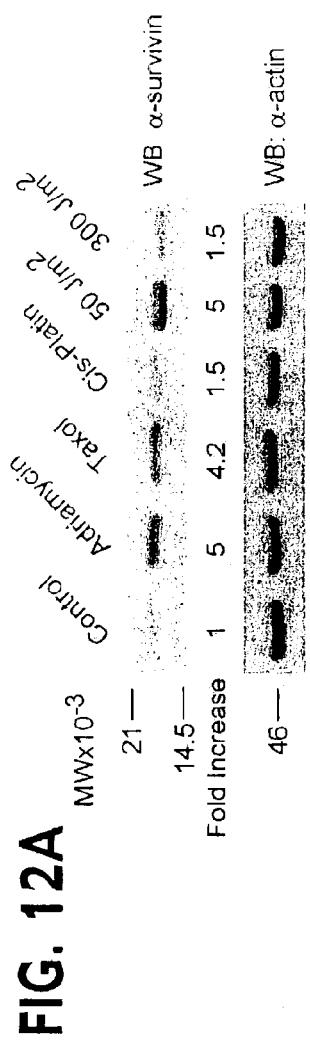
FIGS. 12A and B show Modulation of survivin expression by anti-cancer agents. A. Western blot. MCF-7 cells were treated with adriamycin (100 nM), taxol (2 $\mu$M), cis-platin (3 $\mu$M) or UVB irradiation (50 or 300 J/m2) and analyzed for expression of survivin (top panel) or β-actin (bottom panel), by Western blotting (WB). B. Survivin cytoprotection. MCF-7 cells were infected with pAd-GFP or pAd-survivin and exposed to the indicated UVB doses before determination of DNA content by P.I. staining and flow cytometry. The percentage of cells with apoptotic (sub-G1) DNA content is indicated.
Figure 12B:
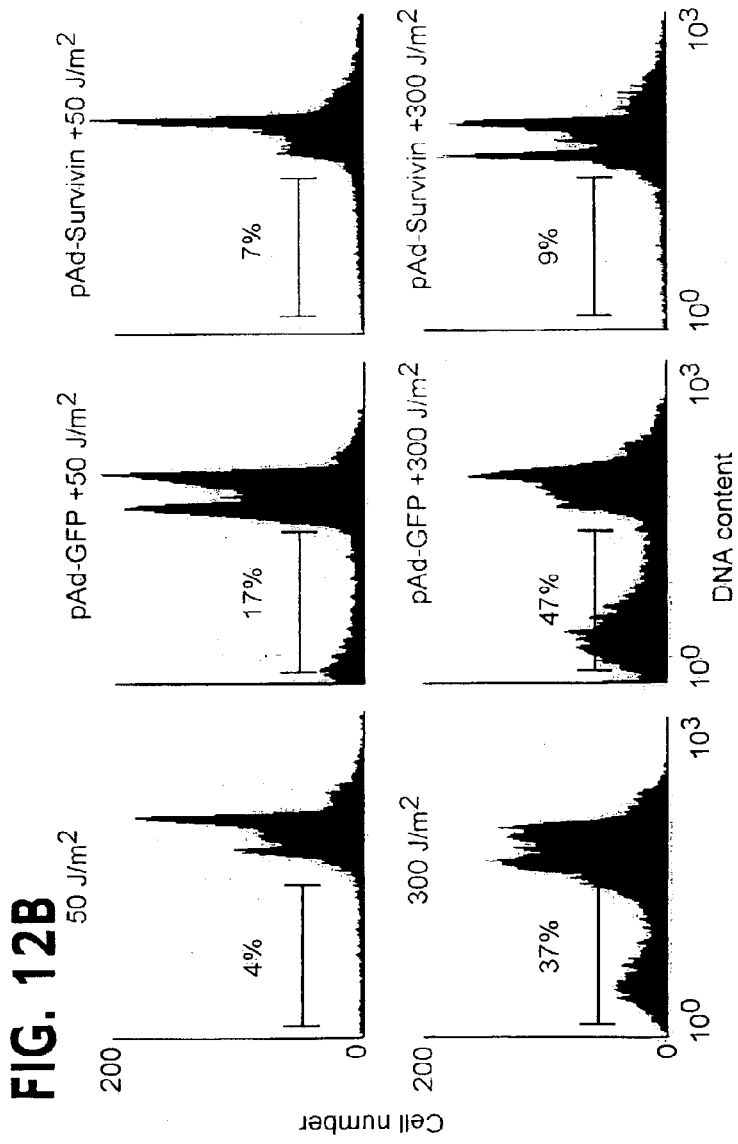
Figure 13C:
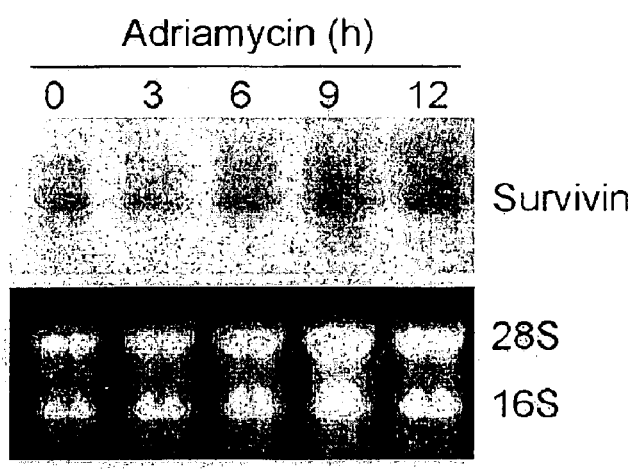
Figure 13D:
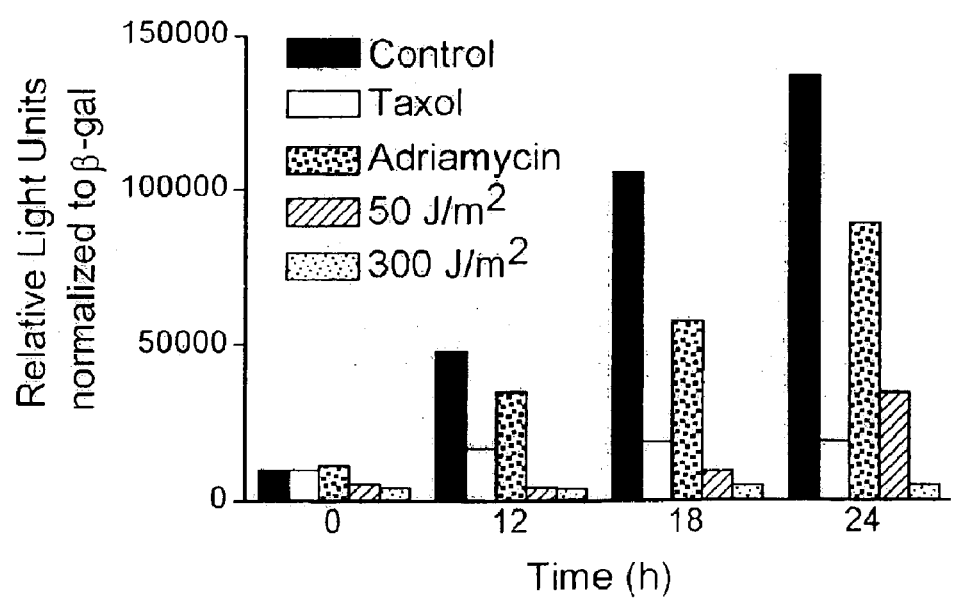

Modulation of Survivin Expression by Anti-Cancer Agents: Exposure of MCF-7 breast carcinoma cells to adriamycin (100 μM), taxol (2 μM) or low-dose UVB irradiation (50 J/m$^2$) induced a 4 to 5-fold increased survivin expression, by Western blotting (FIG. 12A). In contrast, cis-platin (3 μM) or high-dose UVB irradiation (300 J/m$^2$) did not affect survivin levels in MCF-7 cells (FIG. 12A). MCF-7 cell treatment with taxol, adriamycin, cis-platin or low dose UVB irradiation (50 J/m$^2$) induced G2/M arrest and negligible apoptosis, by DNA content analysis and flow cytometry (FIG. 12B, and not shown). In addition, adenoviral expression of survivin effectively counteracted apoptosis induced by high-dose UVB irradiation (300 J/m$^2$), whereas pAd-GFP was ineffective (FIG. 12B). The mechanism(s) of survivin up regulation in the presence of anti-cancer regimens was next investigated. Preincubation of MCF-7 cells with inhibitors of translation (cycloheximide) (FIG. 13A), or transcription (actinomycin D) (FIG. 13B) significantly inhibited the increase in survivin expression mediated by adriamycin, taxol or 50 J/m$^2$ UVB, by Western blotting (FIG. 13A, B). However, no detectable increase in survivin mRNA was observed in adriamycin-treated MCF-7 cells by Northern hybridization (FIG. 13C). In addition, no survivin promoter activity was observed in MCF-7 cells transfected with a survivin-luciferase construct in the presence of the various anti-cancer treatments (FIG. 13D).

Figure 14A:
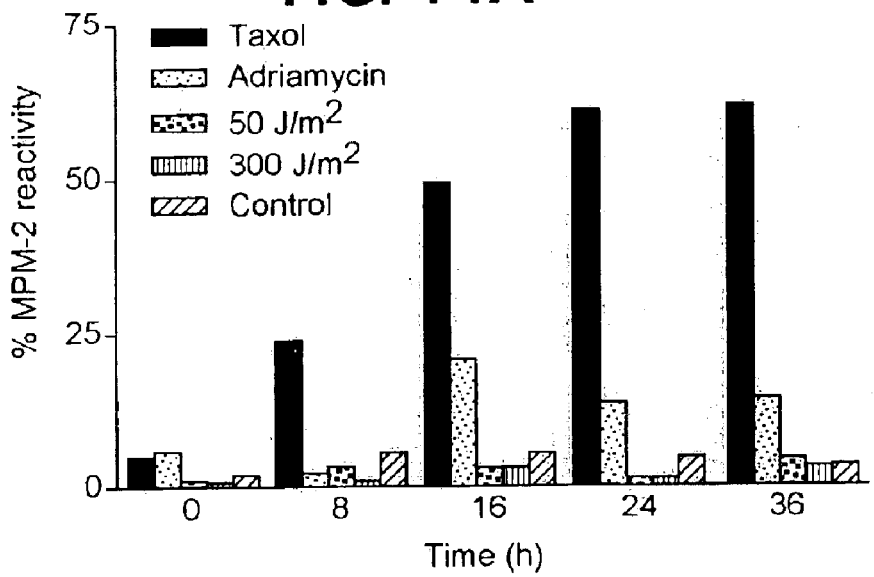
FIGS. 14A–C show differential modulation of p34$^{cdc2}$-cyclin B kinase activity by adriamycin or UVB irradiation. A. MPM-2 expression. MCF-7 cells treated with the indicated anti-cancer agents were harvested after 0–36 h culture, stained with an MPM-2 antibody and analyzed by flow cytometry. B, C. Kinase assay. MCF-7 cells were treated with adriamycin (B, 100 nM) or UVB (C, 50 J/m$^2$) for 0–48 h at 37° C., followed by immunoprecipitation of p34$^{cdc2}$ and kinase assay in the presence of histone H1. p34$^{cdc2}$ immunoprecipitates were immunoblotted with an antibody to survivin followed by chemiluminescence. Control, phosphorylation of H1 by baculovirus-expressed p34$^{cdc2}$-cyclin B1.
Figure 14B:
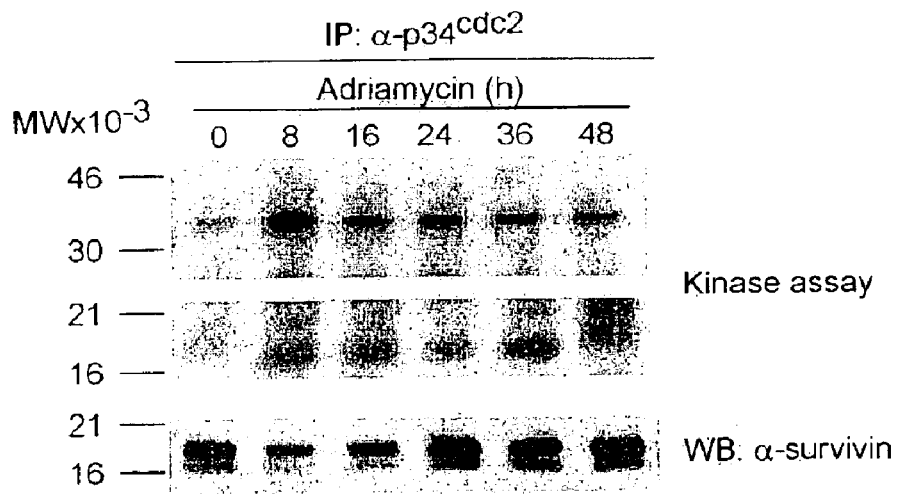
Figure 14C:
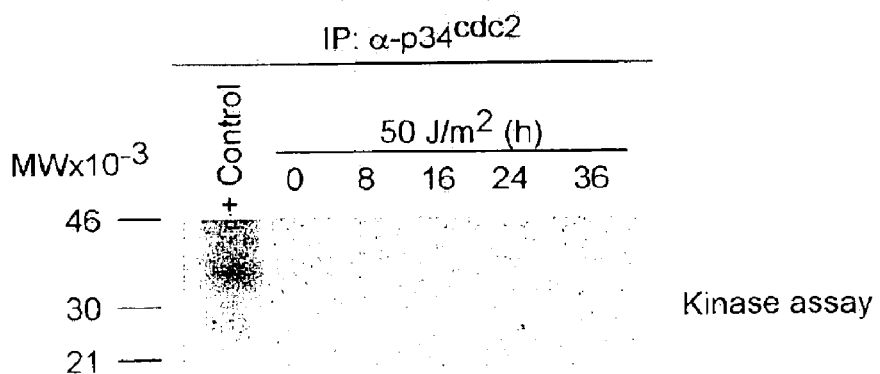

Differential Regulation of P34$^{cdc2}$ Kinase Activity and Survivin Phosphorylation by Anti-Cancer Agents: Previous studies demonstrated that survivin-dependent cytoprotection requires phosphorylation on Thr$^{34}$ by the main mitotic kinase p34$^{cdc2}$-cyclin B1 (D. S. O'Connor et al. (2000) *Proc. Natl. Acad. Sci. USA* 97: 13103–7), and expression of a phosphorylation-defective survivin Thr$^{34}$→Ala mutant caused spontaneous apoptosis, in vitro and in vivo (D. Grossman et al. (2001) *Proc. Natl. Acad. Sci. USA* 98: 635–40; M. Mesri et al. (2001) *J. Clin. Invest.* 108: 981–90). Two-dimensional flow cytofluorometric analysis revealed that DNA damage-induced G2/M arrest by UVB irradiation (50–300 J/m$^2$) resulted in no detectable expression of MPM-2 mitotic phosphoepitope (FIG. 14A). A residual cell population exhibiting MPM-2 expression (20–25%) was observed during adriamycin-induced G2/M arrest, whereas treatment with the microtubule-stabilizing agent, taxol, induced a mitotic arrest with elevated MPM-2 expression (FIG. 14A), in agreement with previous observations (Rudner A. D. et al. (1996) *Curr. Op. Cell. Biol.* 8: 773–80). Also in agreement with previous observations (T. Shimizu et al. (1995) *Cancer Res* 55: 228–31), p34$^{cdc2}$ immunoprecipitated from adriamycin-treated cells phosphorylated ~32 kDa histone H1 in a kinase assay, consistent with MPM-2 phosphoepitope expression under these conditions (FIG. 14B). In addition, p34$^{cdc2}$ immunoprecipitates from adriamycin-treated cells contained a phosphorylated ~16.5 kDa band, which was identified as survivin by sequential Western blotting with an antibody to survivin (FIG. 14B). In contrast, p34$^{cdc2}$ immunoprecipitates from UVB irradiated MCF-7 cells (50 J/m$^2$) did not phosphorylate histone H1, and did not contain co-precipitated survivin, by immunoblotting (FIG. 14C).

Figure 15A:
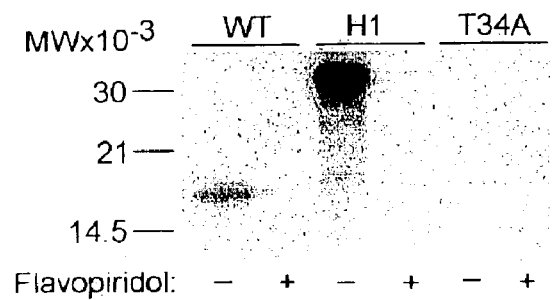
FIGS. 15A–C show modulation of survivin phosphorylation on Thr$^{34}$ and protein expression by flavopiridol. A. In vitro kinase assay. Wild type survivin (WT), histone H1 (H1) or phosphorylation-defective survivin (T34A) (T34A) were incubated with baculovirus-expressed p34$^{cdc2}$-cyclin B1 and $^{32}$P γ-ATP in a kinase assay in the presence or the absence of flavopiridol. Radioactive bands were detected by autoradiography. B. Inhibition of p34$^{cdc2}$-cyclin B1 kinase activity by flavopiridol, in vivo. p34$^{cdc2}$ was immunoprecipitated from HeLa cells after a 24 h treatment with the indicated concentrations of flavopiridol and analyzed for H1 phosphorylation in a kinase assay as described in A. C. Inhibition of survivin phosphorylation on Thr$^{34}$ by flavopiridol, in vivo. HeLa cells were treated with the indicated concentrations of flavopiridol for 24 h and immunoprecipitated (IP) with an antibody to survivin. The immune complexesb were analyzed by Western blotting (WB) with an antibody to Thr$^{34}$-phosphorylated survivin (a-survivinT34*, top panel) or with an antibody to survivin (a-survivin, lower panel) followed by chemiluminescence. For all panels, relative molecular weight markers in kDa are shown on the left.
Figure 15B:
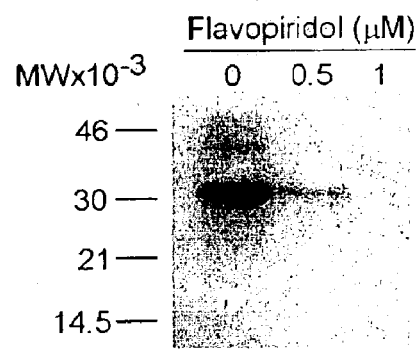
Figure 15C:
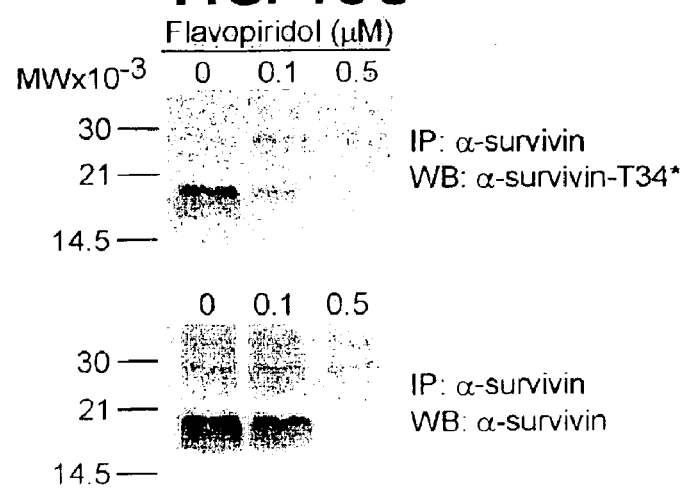

Inhibition of p34$^{cdc2}$ Kinase Activity and Survivin Phosphorylation on Thr$^{34}$ by Flavopiridol: To determine if p34 cdc2 phosphorylation contributed to increased survivin expression during G2/M arrest, we used the cyclin-dependent kinase inhibitor, flavopiridol (V. Patel et al. (1998) *J. Clin. Invest.* 102: 1674–81). Incubation of baculovirus-expressed p34$^{cdc2}$-cyclin B1 with 100 nM flavopiridol suppressed phosphorylation of H1 and wild type survivin in a kinase assay, in vitro (FIG. 15A). In contrast, no phosphorylation of survivin (T34A) by p34$^{cdc2}$-cyclin B1 was observed in the presence or absence of flavopiridol (FIG. 15A). Treatment of HeLa cells with increasing concentrations of flavopiridol resulted in dose-dependent inhibition of H1 phosphorylation by immunoprecipitated p34$^{cdc2}$ (FIG. 15B). In addition, analysis of survivin immunoprecipitated from flavopiridol-treated cells revealed concentration-dependent inhibition of phosphorylation on Thr$^{34}$, by Western blotting with a phospho-Thr$^{34}$-specific antibody (a-survivinT34*) (FIG. 15C). At higher flavopiridol concentrations, inhibition of survivin phosphorylation on Thr$^{34}$ was also associated with complete loss of survivin expression, by Western blotting (FIG. 15C).

Figure 16A:
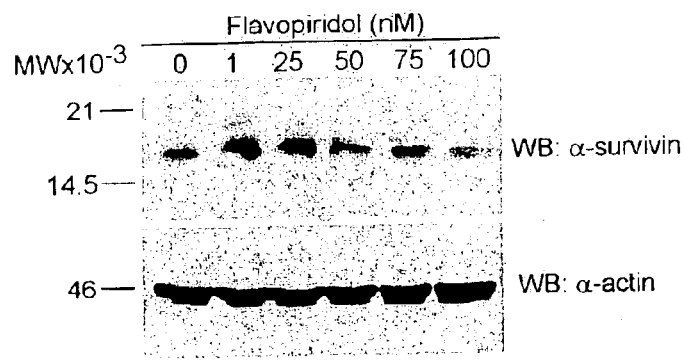
FIGS. 16A–E show regulation of survivin expression by flavopiridol. A. Concentration-dependence. HeLa cells were treated with the indicated increasing concentrations of flavopiridol for 48 h and analyzed for expression of survivin (top panel) or β-actin (bottom panel) by Western blotting. B. Time-course. Hela cells were treated with 100 nM flavopiridol for the indicated time intervals and analyzed for expression of survivin (top panel) or β-actin (bottom panel) by Western blotting. C. Effect of flavopiridol on bcl-2 expression. The experimental conditions are the same as in A, except that flavopiridol-treated HeLa cells were analyzed by Western blotting with an antibody to Bcl-2. D. Effect of genistein or TNF a on survivin expression. HeLa cells were treated with the tyrosine kinase inhibitor genistein (25 µM) or TNF a (5 ng/ml) for 48 h, harvested and analyzed for survivin expression by Western blotting. For all panels, relative molecular weight markers in kDa are shown on the left. E. Flavopiridol-induced apoptosis. HeLa cells were treated with the indicated increasing concentrations of flavopiridol for 48 h and analyzed for DNA content by propidium iodide staining and flow cytometry. The percentage of apoptotic cells with sub-G1 DNA content is indicated. Insert, nuclear morphology of apoptosis (DNA fragmentation, chromatin condensation) in untreated or flavopiridol-treated HeLa cells, by DAPI staining.
Figure 16B:
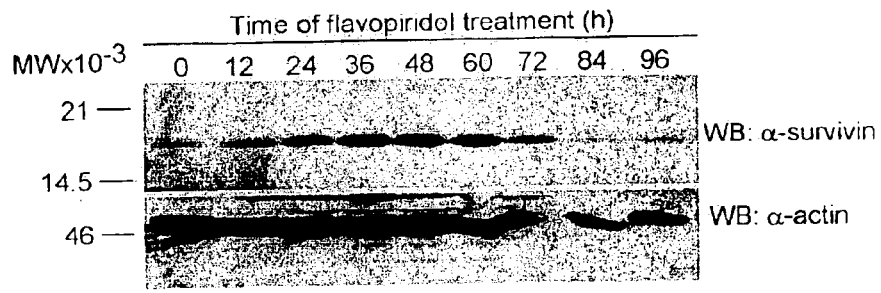
Figure 16C:
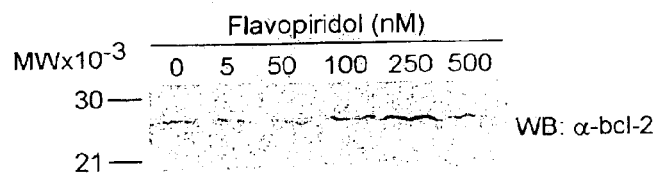
Figure 16D:
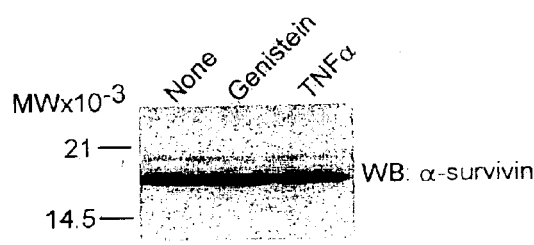
Figure 16E:
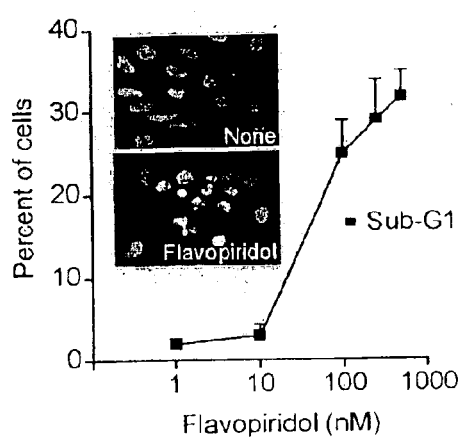

Regulation of Survivin Expression and Apoptosis by Flavopiridol: Treatment of HeLa cells with flavopiridol resulted in a concentration-dependent decrease in survivin expression, by Western blotting (FIG. 16A). Nearly complete loss of survivin expression in HeLa cells was achieved at concentrations of flavopiridol of 100 nM (FIG. 5A), after an 84–96 h treatment (FIG. 16B). However, a modest increase in survivin expression is recorded with 1 and 25 nM flavopiridol and between 12 and 72 hours. This increase may reflect a transient enrichment in G2/M-arrested cells induced by drug treatment. In contrast, flavopiridol did not affect expression of antiapoptotic Bcl-2 (FIG. 16C), and treatment of HeLa cells with the flavone genistein that does not inhibit Cdk activity (H. Nakagawa et al. (2000) *J. Cancer Res. Clin. Oncol.* 126: 448–54), or TNF a, did not affect survivin expression by Western blotting (FIG. 16D). Loss of survivin expression in flavopiridol-treated HeLa cells was associated with a concentration-dependent increase in the population with hypodiploid (apoptotic) DNA content (FIG. 16E), and apoptotic nuclear morphology of chromatin condensation and DNA fragmentation, by DAPI staining (FIG. 16E, inset). Preincubation of HeLa cells with the broad-spectrum caspase inhibitor Z-VAD-fmk suppressed flavopiridol-induced apoptosis (not shown).

Figure 17A:
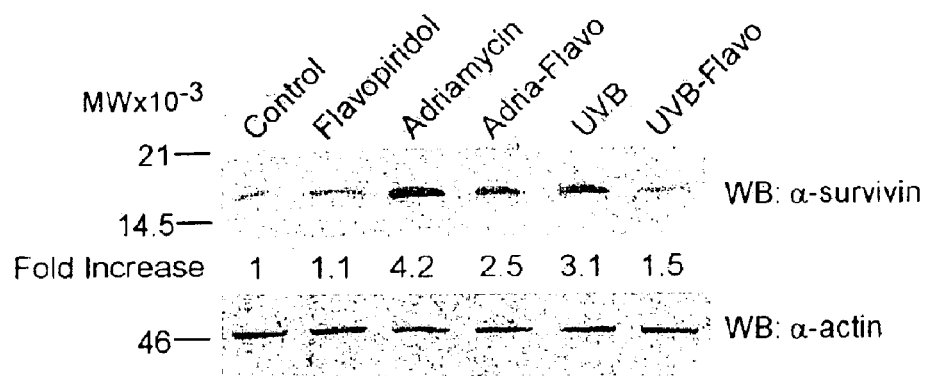
FIGS. 17A–C show flavopiridol eliminates increased survivin expression and enhances genotoxic stress-induced apoptosis. A. Suppression of survivin stability by flavopiridol. MCF-7 cells (2×10$^5$/ml) were treated with adriamycin (100 nM) or UVB irradiation (50 or 300 J/m$^2$) in the presence or the absence of flavopiridol (100 nM) for 18 h, and analyzed for expression of survivin or β-actin by Western blotting and densitometry (bottom panel). B. Selective enhancement of apoptosis by flavopiridol. The experimental conditions are as in A, except that MCF-7 cells treated with the various combinations of anti-cancer agents were analyzed for DNA content by P.I. staining and flow cytometry. Results represent the mean±SD of three different experiments. C. Inhibition of survivin phosphorylation on Thr$^{34}$. Survivin was immunoprecipitated from MCF-7 cells treated as in A, and immune complexes were analyzed by Western blotting (WB) with antibodies to survivin or phospho-T34 survivin (a-survivinT34*).
Figure 17B:
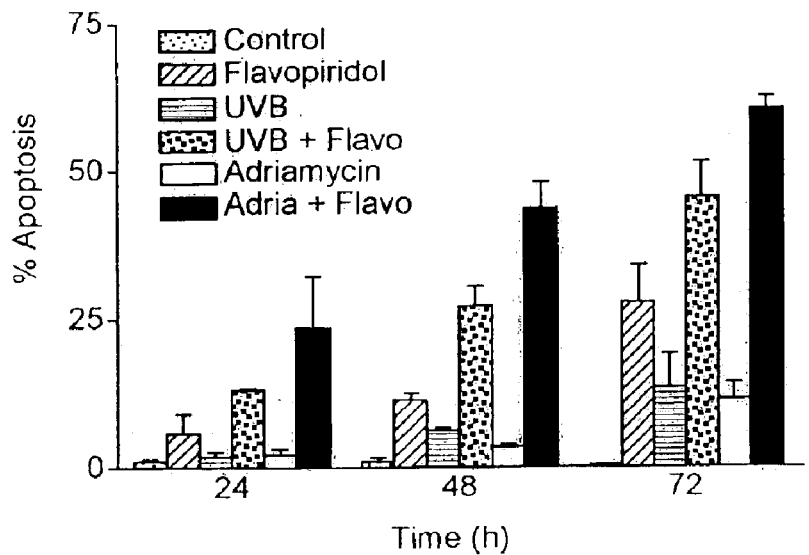
Figure 17C:
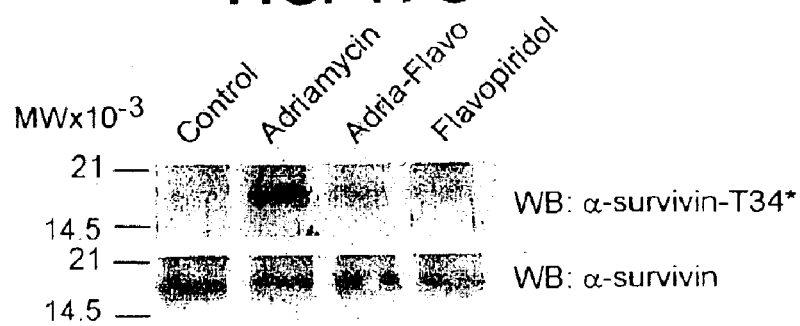

Flavopiridol Regulation of Survivin Expression by Anti-Cancer Agents: The possibility that inhibition of survivin phosphorylation on Thr$^{34}$ by flavopiridol could influence survivin levels during G2/M arrest was next investigated. Treatment of MCF-7 cells with 100 nM adriamycin or 50 J/m$^2$ UVB irradiation resulted in increased survivin expression, by Western blotting (FIG. 17A), and in agreement with the data presented above. Treatment with flavopiridol alone (100 nM for 72 h) did not significantly affect survivin levels (FIG. 17A), consistent with the time-course of survivin down-regulation by flavopiridol (FIG. 16B). However, sequential treatment of MCF-7 cells with anti-cancer agents for 18 h followed by flavopiridol for 72 h suppressed survivin levels to background values of untreated cultures (FIG. 17A). This was associated with significant enhancement of apoptosis induced by UVB (2-, 5- and 12-%) and adriamycin (2-, 3- and 10-%) to 12-, 26-, 46-% and 22-, 45-, 60-% respectively (FIG. 17B). Under these experimental conditions, flavopiridol suppressed survivin phosphorylation on Thr$^{34}$ in the presence of 100 nM adriamycin to background levels of untreated cultures (FIG. 17C).

Figure 18A:
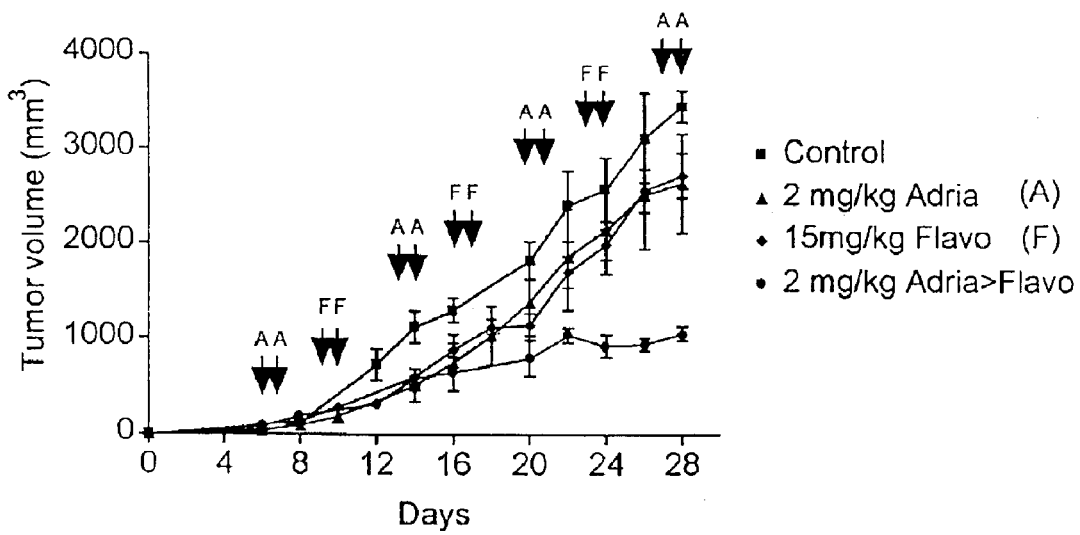
FIGS. 18A and B show inhibition of tumor formation by sequential adriamycin-flavopiridol treatment. A. Kinetics of tumor formation. MCF-7 cells (2.5×10$^6$) were grown as xenograft tumors in immunoincompetent SCID mice. Animals (10 per group) were treated with adriamycin (A; 1 mg/kg/day×2 days or 2 mg/kg), flavopiridol (F; 7.5 mg/kg/day×2 days or 15 mg/kg), or the sequential treatment of adriamycin followed by flavopiridol. Tumor growth was monitored in three dimensions and expressed as tumor volume in mm$^3$. B. Survivorship of SCID mice bearing MCF-7 tumors. Curves were based on mouse tumor burden of 3000 mm$^3$, at which animals were sacrificed.
Figure 18B:
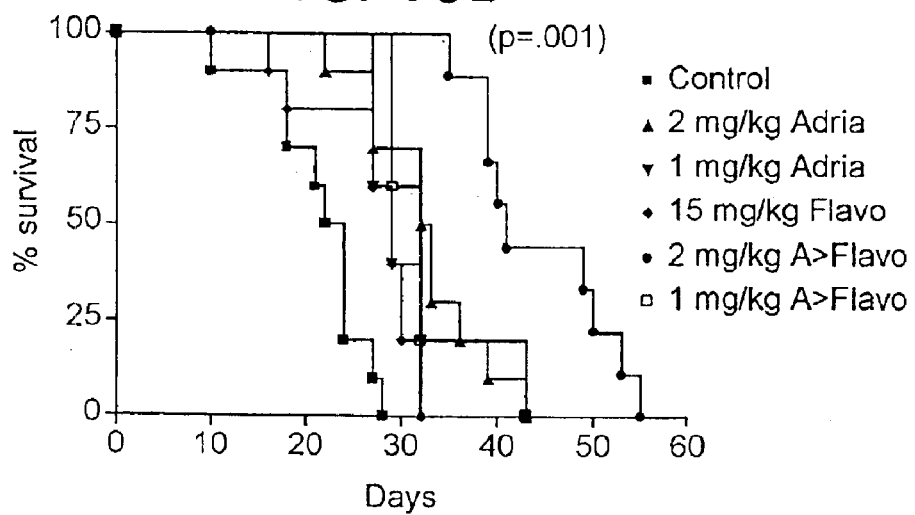

Sequential Combination Treatment with Flavopiridol Exhibits Anti-Cancer Activity In Vivo: The possibility that targeted inhibition of survivin phosphorylation by flavopiridol could function as a novel anticancer regimen was next investigated. Injection of 2.5×10$^6$ MCF-7 cells into the flank of 5–6 week old SCID/bg mice resulted in exponentially growing tumors. Treatment of animals bearing established tumors (70–100 mm$^3$) with adriamycin (2 mg/kg) or flavopiridol (15 mg/kg) alone did not affect the kinetics of tumor growth, as compared with animals given vehicle (FIG. 18A). However, sequential combination therapy of adriamycin (1 mg/kg/day for 2 days) followed by flavopiridol (7.5 mg/kg/day for 2 days) arrested tumor growth and resulted in indefinite survival of all treated animals (FIG. 18A). Significantly increased survival (P<0.0001) was also observed upon suspension of sequential adriamycin-flavopiridol treatment, when tumors exhibited de novo growth comparably to animals receiving single anti-cancer regimens (FIG. 18B). Sequential treatments using 0.5 mg/kg/day×2 days adriamycin was no better then adriamycin alone and sequential treatment using 2 mg/kg/day×2 days proved toxic to the animals (data not shown).

Example 8

A p34$^{cdc2}$ Survival Checkpoint in Cancer

Protein kinase inhibitors are currently explored as anti-cancer drugs for their ability to disrupt signaling pathways controlling cell proliferation and cell survival. However, concerns of specificity, influence of cellular context and an incomplete understanding of molecular targets have limited the use of kinase antagonists in cancer therapy. This study shows that suppression of p34$^{cdc2}$ kinase in tumor cells treated with taxol eliminates a critical survival pathway. This results in escape from taxol-imposed mitotic block, massive apoptosis, and sustained inhibition of tumor growth, in vivo. Taxanes are first-line treatment for common human tumors, and the sequential combination with an antagonist of p34 cdc2 kinase may rationally enhance their therapeutic efficacy.

A checkpoint surveying the entry into mitosis responds to defects in spindle microtubule assembly/stability. This has been used in cancer therapy to arrest cell division and trigger apoptosis, but how the spindle checkpoint couples to the cell survival machinery has remained elusive. This study shows that microtubule stabilization engenders a survival pathway that depends on elevated levels of p34$^{cdc2}$ kinase and increased expression of the apoptosis inhibitor and mitotic regulator, survivin. Conversely, genetic or pharmacologic ablation of p34$^{cdc2}$ kinase during spindle checkpoint activation resulted in massive apoptosis independently of p53. When used as a novel anti-cancer strategy, inhibition of p34$^{cdc2}$ kinase after spindle damage suppressed tumor growth and promoted indefinite survival without toxicity in mice. By ablating this viability checkpoint, inhibitors of p34$^{cdc2}$ kinase could safely improve the efficacy of microtubule poisons used to treat common cancers.

Methods

Cell Cultures and Antibodies: Breast carcinoma MCF-7, prostate carcinoma PC3, and cervical carcinoma HeLa cells (American Type Culture Collection, Manassas, Va.) were maintained in culture according to the supplier's recommendations. HT2–19 cells with conditional inactivation of the p34$^{cdc2}$ gene were described previously (J. E. Itzhaki et al. (1997) *Nat. Gen.* 15: 258–265). In this cell line, removal of IPTG from the culture medium results in inactivation of the second p34$^{cdc2}$ allele (J. E. Itzhaki et al. (1997) *Nat. Gen.* 15: 258–265). For spindle checkpoint activation, the various cell types were treated with taxol (0.2–2 μM, Sigma Chemical Co., St. Louis, Mo.), vincristine (100 nM, Sigma) or cisplatin (3 μM, Sigma) for 16 h at 37° C. For genetic ablation of p34$^{cdc2}$, HT2–19 cells were washed and cultivated in the absence of IPTG for 48–72 h before analysis of apoptosis (see below) or expression of survivin or p34$^{cdc2}$, by Western blotting. In some experiments, taxol (0.2 μM) was added to HT2-19 cells simultaneously with the withdrawal of IPTG, and cells were processed as described above. A replication-deficient adenovirus encoding wild type survivin (pAd-Survivin) or control GFP (pAd-GFP) was generated using the pAd-Easy system, as described previously (M. Mesri et al. (2001) *J. Clin. Invest.* 108: 981–990), and propagated in HEK293 cells with purification by CsCl banding. With this protocol, no replication-competent adenovirus particles were generated (M. Mesri et al. (2001) *J. Clin. Invest.* 108: 981–990). For viral transduction, HT2–19 cells in the absence of IPTG were infected with pAd-GFP or pAd-Survivin at multiplicity of infection (m.o.i.) of 50, and analyzed after a 48–72 h culture for changes in cell cycle progression and apoptosis. An antibody to p34$^{cdc2}$ was obtained from Pharmingen (San Diego, Calif.) and used in previous experiments (D. S. O'Connor et al. (2000) *Proc. Natl. Acad. Sci. USA* 97: 13103–13107). An antibody to β-actin was from Sigma. An antibody to caspase-9 was from Transduction Laboratories (Beverly, Mass.). A rabbit polyclonal antibody to survivin was from NOVUS Biologicals (Littleton, Colo.), and characterized in recent studies (P. Fortugno et al. (2002) *J. Cell. Sci.* 115: 575–585). An affinity purified antibody to Thr$^{34}$-phosphorylated survivin (a-survivinT34*) was characterized previously (D. S. O'Connor et al. (2000) *Proc. Natl. Acad. Sci. USA* 97: 13103–13107).

Modulation of Survivin Expression During Checkpoint Activation: HeLa, PC3 or MCF-7 cells were incubated with taxol (0.2–2 μM) or vincristine (100 nM) for 16 h at 37° C., followed by inhibitors of cyclin-dependent kinases (Cdk) Purvalanol A (Purvalanol A, 1–20 μM), alsterpaullone (20 μM), flavopiridol (250 nM) or olomoucine (400 mM) for increasing time intervals (4–32 h) at 37° C. In other experiments, HeLa cells were treated with taxol (0.2 μM) for 16 h followed by the DNA damaging agent adriamycin (100 nM, Sigma) or the nucleoside analog 5-Fluorouracil (500 μM, Sigma) for 8–32 h at 37° C. Changes in survivin expression under the various conditions tested were analyzed by Western blotting, as described (D. S. O'Connor et al. (2000) *Proc. Natl. Acad. Sci. USA* 97: 13103–13107). In some experiments, HeLa cells were transfected by lipofectamine with a minimal survivin promoter construct upstream of a luciferase reporter gene (pLuc-cyc1.2), as described (F. Li et al. (1998) *Nature* 396: 580–584). Cells were treated with taxol (2 μM) or UVB (50 J/m2), and analyzed for changes in luciferase activity at increasing time intervals (12–36 h) in a luminometer. Luciferase values were normalized to β-galactosidase expression. Immunoprecipitation of endogenous survivin from HeLa cells treated with taxol or the sequential combination of taxol-Purvalanol A was carried out as described (D. S. O'Connor et al. (2000) *Proc. Natl. Acad. Sci. USA* 97: 13103–13107). The immune complexes were separated by SDS gel electrophoresis and analyzed with antibodies to survivin or a-survivinT34* by Western blotting. For cycloheximide block experiments, subconfluent cultures of HeLa cells were transfected with GFP-survivin or GFP survivin(T34A) by lipofectamine, as described (D. S. O'Connor et al. (2000) *Proc. Natl. Acad. Sci. USA* 97: 13103–13107). After a 16-h interval, cells were incubated with cycloheximide (20 μM) to prevent further expression of transfected plasmids plus the broad-spectrum caspase inhibitor, Z-VAD-fmk (20 μM) to prevent loss of cell viability associated with survivin(T34A) expression (D. S. O'Connor et al. (2000) *Proc. Natl. Acad. Sci. USA* 97: 13103–13107). Aliquots of the various cultures were harvested 24–48 h after cycloheximide block, and analyzed for expression of GFP-containing fusion proteins by Western blotting with an antibody to GFP.

MPM-2 Mitotic Phosphoepitope Expression: For detection of mitotic phosphoproteins (D. D. Vandre et al. (1989) *J. Cell Sci.* 94: 245–258), MCF-7 cells (1–2×10$^5$ cells/60 mm dish) were treated with taxol (0.2 μM), or vincristine (100 nM) for increasing time intervals (8–36 h) at 37° C. Cells were fixed in 70% ethanol, labeled with MPM-2 antibody (6 μg/ml; Upstate Biotechnology, Lake Placid, N.Y.) followed by addition of goat anti-mouse FITC (Boehringer Mannheim) for 1 h at 22° C. in the presence of 5 μg/ml propidium iodide containing 50 μg/ml RNAse A. Samples were analyzed on a FACScan (Becton Dickinson, Mountain View, Calif.), using CellQuest software. Data are expressed as %MPM-2 positive cells in the entire population.

Determination of Apoptosis: Changes in apoptosis in cultures treated with the various combinations of microtubule poisons were monitored by DNA content analysis by propidium iodide staining and flow cytometry, as described (F. Li et al. (1999) *Nat. Cell.* 1: 461–466). Alternatively, cells were analyzed for nuclear morphology by DAPI staining (F. Li et al. (1999) *Nat. Cell.* 1: 461–466). In other experiments, HeLa cells were detergent solubilized and analyzed for proteolytic processing of ~46 kD proform caspase-9 by Western blotting (D. S. O'Connor et al. (2000) *Proc. Natl. Acad. Sci. USA* 97: 13103–13107).

Breast Cancer Xenograft Model: All experiments involving animals were approved by the institutional animal cure and use committee. Six- to eight-week old female CB17 SCID/beige mice (Taconic Farms, Germantown, N.Y.) were injected s.c. into the flanks with 2.5×10$^6$ exponentially growing MCF-7 cells in 250 μl of sterile PBS, pH 7.4. Tumor growth was confined to local masses and did not affect animal survival over a 4-month observation period. Tumors became palpable (25–75 mm$^3$) within 5 days of tumor cell injection, after which groups of six animals were randomized and assigned to different treatment groups. Animals were injected i.p. with taxol alone (2.5 or 5 mg/kg), Purvalanol A alone (20 mg/kg) or the sequential combination of taxol-Purvalanol A for two consecutive days each divided by a day with no treatment. For single agent treatment, vehicle was given in place of taxol or Purvalanol A with the same schedule. Each complete cycle was separated by 2 d without treatment. Tumor volume was measured in the three dimensions with a caliper. Animals with tumor burden >3000 mm$^3$ were sacrificed (Survival).

Statistical Analysis: All in vitro experiments were repeated at least three times. For in vivo studies, each X value (time) shows the fraction of animals still alive calculated using the product limit or Kaplan-Meier method. The survival curves were compared using the log-rank test. This test generates a P value testing the null hypothesis that the survival curves are identical in the overall populations.

Results

Figure 19A:
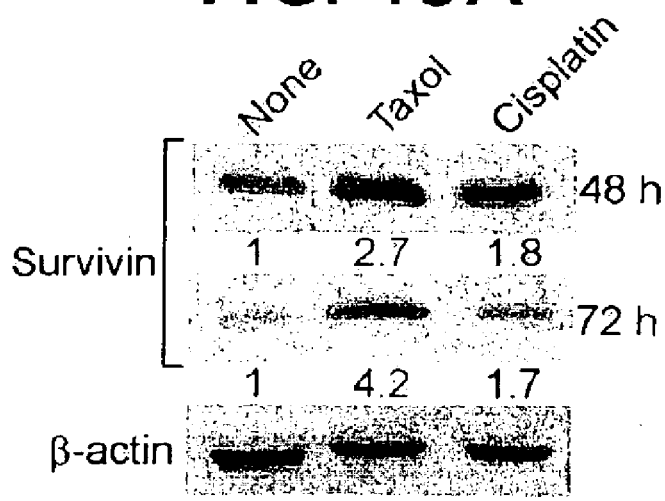
FIGS. 19A and B show increased survivin expression after spindle checkpoint activation. A. Western blotting. MCF-7 cells were left untreated (None) or treated with taxol (2 µM) or cisplatin (3 µM) and analyzed for expression of survivin or β-actin at the indicated time intervals, by Western blotting. Numbers indicate fold increase by densitometry normalized to β-actin levels. B. Promoter activity. MCF-7 cells were transfected with a minimal survivin promoter construct (pLuc-1430) upstream of a luciferase reporter gene. Luciferase activity was determined at the indicated time intervals after treatment with vehicle (None), taxol (2 µM) or UVB (50 J/m$^2$).
Figure 19B:
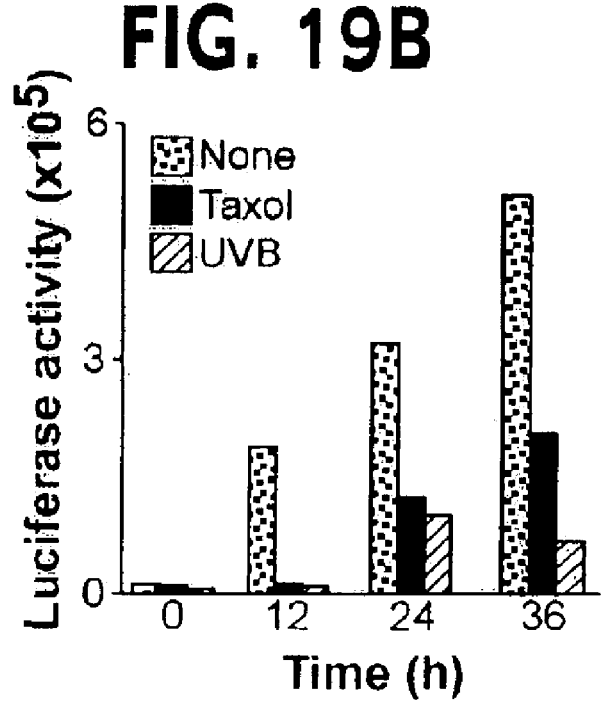

Regulation of Survivin Expression During Spindle Checkpoint Activation: To activate the mitotic spindle checkpoint in breast carcinoma MCF-7 cells carrying wild type p53, we initially used the microtubule-stabilizing agent taxol (A. C. Yvon et al. (1999) *Mol. Biol. Cell* 10: 947–959). Treatment with low concentrations taxol (0.2–2 μM) caused a sustained (48–72 h) mitotic arrest at the metaphase-anaphase transition with elevated p34$^{cdc2}$ kinase activity, as measured by MPM-2 phosphoepitope expression (D. D. Vandre et al. (1989) *J. Cell Sci.* 94: 245–258). This was associated with a ~3–4-fold increased expression of survivin in taxol-treated MCF-7 cells, whereas cisplatin was less effective (FIG. 19A). To determine whether modulation of survivin levels after spindle checkpoint activation required de novo gene expression, we transfected MCF-7 cells with a minimal survivin promoter upstream of a luciferase reporter gene. In untreated cultures, there was a time-dependent increase in luciferase activity reflecting expression of the survivin promoter (F. Li et al. (1998) *Nature* 396: 580–584). In contrast, taxol treatment significantly inhibited survivin gene expression at all time intervals examined (FIG. 19B). In parallel experiments, a G2/M arrest induced by UVB irradiation also resulted in profound suppression of survivin gene expression in MCF-7 cells (FIG. 19B). In Northern hybridization experiments, no significant changes in survivin RNA levels were observed in HeLa cells in the presence of absence of taxol.

Figure 20A:
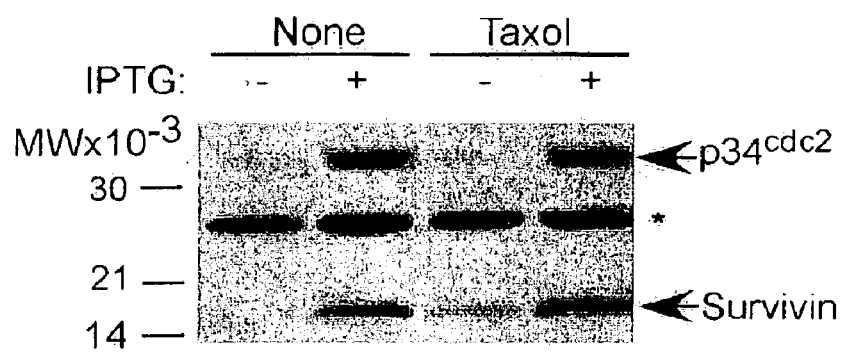
FIGS. 20A–E show p34$^{cdc2}$ kinase activity modulates survivin expression during spindle checkpoint activation. A. Conditional ablation of p34$^{cdc2}$ gene expression. HT2–19 cells in the presence p34$^{cdc2}$ +/−) or absence (p34 cdc2 −/−) of IPTG for 24 h were treated with vehicle or taxol (0.2 µM) for a further 24 h, and analyzed for expression of p34$^{cdc2}$ or survivin, by Western blotting. *, non specific band. B. Effect of kinase inhibitors on MPM-2 mitotic phosphoepitope expression. Cervical carcinoma HeLa cells were treated with taxol (0.2 µM for 16 h, ■) followed by Cdk inhibitors Purvalanol A (10 µM), alsterpaullone (Alster., 20 µM), flavopiridol (Flavop., 250 nM), or olomoucine (Olom., 400 µM) for addition 16 h ▣, or 32 h ▨, before analysis of MPM 2 expression by flow cytometry. Data are expressed as % of MPM-2$^+$ cells in the entire cell population analyzed by propidium iodide staining. C. Effect of Purvalanol A on survivin phosphorylation on Thr$^{34}$. Survivin was immunoprecipitated from HeLa cells treated with 0.2 µM taxol for 16 h followed by vehicle or Purvalanol A (20 µM) for additional 16 h. The immune complexes were analyzed by Western blotting with a T34-phospho-specific antibody (Survivin-T34*), or an antibody to survivin (Survivin). D. Effect of Purvalanol A on survivin expression. HeLa cells were left untreated (None) or treated with taxol (0.2 µM), taxol (0.2 µM for 16 h) followed by Purvalanol A (20 µM for additional 16 h) or in reverse combination, and analyzed for expression of survivin or cyclin B1, by Western blotting. E. Kinetics of protein expression after cycloheximide block. HeLa cells were transfected with cDNAs encoding wild type survivin (WT) or a phosphorylation-defective survivin Thr$^{34}$→Ala mutant (T34A) fused to Green Fluorescence Protein (GFP). After a 16 h incubation, cultures were incubated with 20 µM cycloheximide plus 20 µM Z-VAD-fmk, harvested at the indicated time intervals and analyzed with antibodies to GFP or β-actin, by Western blotting.
Figure 20B:
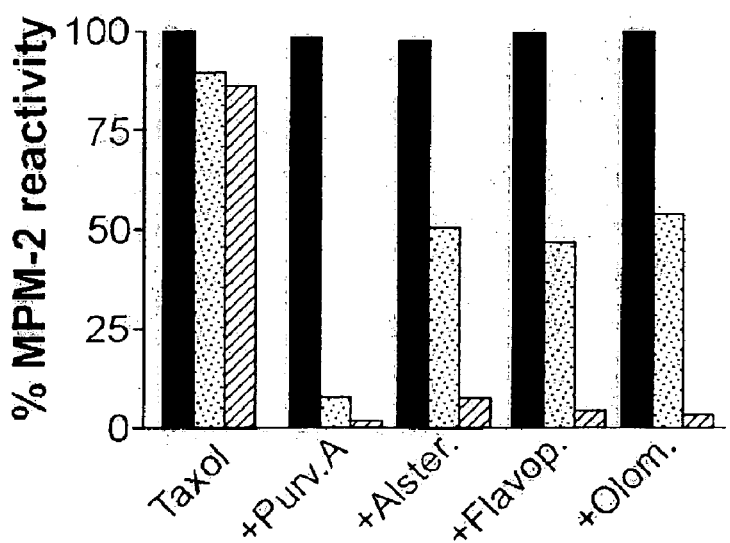
Figure 20C:
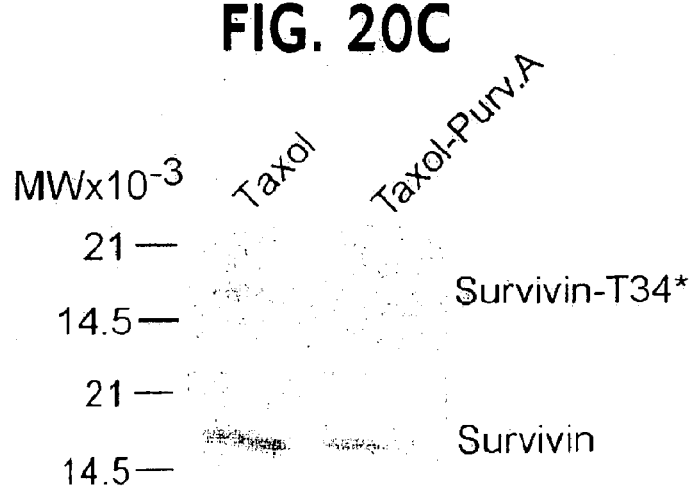
Figure 20D:
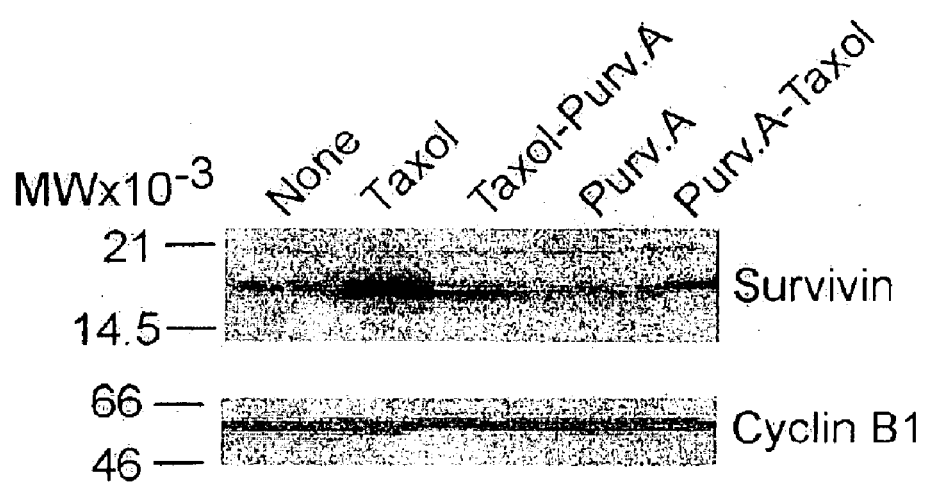
Figure 20E:
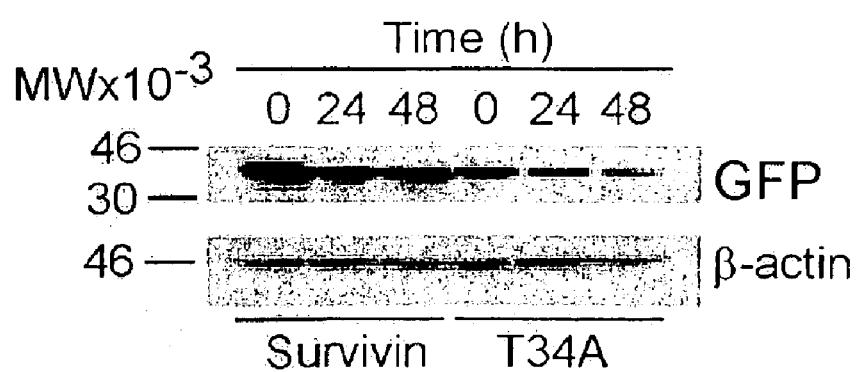

Regulation of Survivin Expression by p34$^{cdc2}$ Kinase Activity: The possibility that elevated p34$^{cdc2}$ activity contributed to increased survivin expression during spindle checkpoint activation was next investigated. First, an assay was performed using HT2-19 cells carrying an inactivated allele of p34$^{cdc2}$ and a second allele that is conditionally silenced upon removal of IPTG from the culture media (J. E. Itzhaki et al. (1997) *FASEB J.* 15: 2721–2723). In the presence of IPTG (p34$^{cdc2}$ +/−), HT2-19 cells expressed p34$^{cdc2}$ and endogenous survivin, by Western blotting (FIG. 20A). A 48-h culture in the absence of IPTG (p34$^{cdc2}$ −/−) resulted in nearly complete loss of both p34$^{cdc2}$ and survivin expression (FIG. 20A). Consistent with the data presented above, taxol treatment resulted in increased survivin levels in IPTG+HT2-19 cells, whereas only a minimally detectable increase in survivin expression was observed in the absence of IPTG (FIG. 20A), potentially reflecting residual p34$^{cdc2}$ kinase activity. Next, the ability tested the ability of cyclin-dependent kinase (Cdk) inhibitors to interfere with survivin expression was tested. Similarly to MCF-7 cells, taxol treatment of cervical carcinoma HeLa cells carrying functionally inactivated p53 resulted in mitotic arrest with elevated p34$^{cdc2}$ kinase activity, which remained sustained for a 32-h culture (FIG. 20B). Sequential addition of the purine inhibitor of the Cdk ATP binding site, Purvalanol A (N. S. Gray et al. (1998) Science 281:533–538), to taxol-treated cells completely suppressed MPM-2 mitotic phosphoepitope expression at the earliest time point tested (16 h), and throughout a 32 h culture (FIG. 20B). In contrast, Cdk inhibitors alsterpaullone, flavopiridol or olomoucine partially inhibited MPM-2 expression at 16 h, and suppressed mitotic phosphoprotein expression at 32 h (FIG. 20B). Sequential addition of Purvalanol A to taxol-treated HeLa cells suppressed phosphorylation of endogenous survivin on Thr$^{34}$, by Western blotting of survivin immunoprecipitates with a Thr$^{34}$-phospho-specific antibody (D. S. O'Connor et al. (2000) Proc. Natl. Acad. Sci. 97: 13103–13107) (FIG. 20C). This was associated with inhibition of increased survivin expression after taxol treatment, by Western blotting (FIG. 20D). In contrast, Purvalanol A alone or the reverse sequence of Purvalanol A followed by taxol did not affect survivin levels in HeLa cells (FIG. 20D). To determine if phosphorylation by p34$^{cdc2}$ influenced survivin stability, cycloheximide block in HeLa cells transfected with survivin cDNAs fused to Green Fluorescence Protein (GFP) was used. To overcome apoptosis induced by expression of survivin(T34A) (D. S. O'Connor et al. (2000) Proc. Natl. Acad. Sci. 97: 13103-13107), a broad-spectrum caspase inhibitor, Z-VAD-fink (20 μM), was added to the various cultures. HeLa cells transfected with wild type survivin exhibited time-dependent expression of a GFP-containing fusion protein that remained sustained for up to 48 h after transfection, by Western blotting (FIG. 20E). In contrast, nonphosphorylatable survivin(T34A) was rapidly cleared from HeLa cells, and depleted 48 h after transfection (FIG. 20E).

Figure 21A:
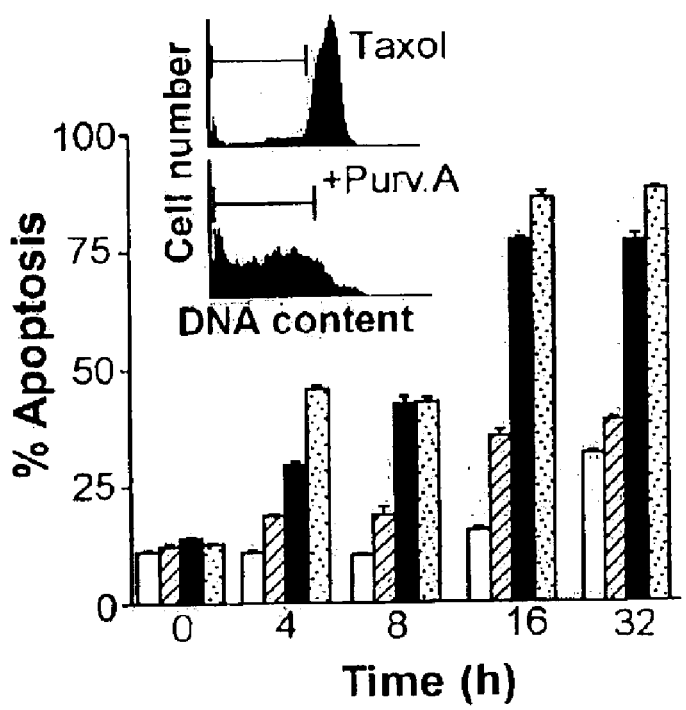
FIGS. 21A–D show time- and sequence-specific inhibition of p34$^{cdc2}$ kinase activity after spindle checkpoint activation induces apoptosis. A. Time-course. HeLa cells incubated with 0.2 µM taxol for 16 h (□) were sequentially treated with 1 µM (▨), 10 µM (■) or 20 µM (▣) Purvalanol A. Cells were harvested at the indicated time intervals and analyzed for hypodiploid (apoptotic) DNA content by propidium iodide staining and flow cytometry. Inset. DNA content profiles of HeLa cells treated with taxol alone (homogeneous mitotic arrest) or the sequential combination of taxol-Purvalanol A (escape from mitotic block and apoptosis). B. Caspase-9 cleavage. HeLa cells were left untreated (None) or treated with taxol (0.2 µM), Purvalanol A (20 µM) or the sequential combination taxol-Purvalanol A for 16 h, harvested and analyzed for caspase-9 processing, by Western blotting. Arrows indicate the position of ~46 kD proform and ~37 kD active form of caspase-9, respectively. *, non-specific band. C. Sequence specificity. HeLa cells treated with Purvalanol A (20 µM, ▣), Purvalanol A-taxol (0.2 µM) in reverse combination (▨) or taxol-Purvalanol A (■) were analyzed for induction of apoptosis as in A. Inset. Drug-specificity. HeLa cells were treated with taxol (0.2 µM) or the sequential combination of taxol-Purvalanol A (+Purvalanol A), taxol-adriamycin (+Adria) or taxol-5-Fluorouracil (+5-FU) and analyzed for induction of apoptosis as in A. D. p53 independence. Prostate carcinoma PC3 cells were treated with the indicated combinations, harvested after 16 h and analyzed for induction of apoptosis as in A. Inset. Modulation of survivin expression. PC3 cells were left untreated (None) or incubated with taxol or the taxol-Purvalanol A combination, and analyzed for expression of survivin or p53, by Western blotting.
Figure 21B:
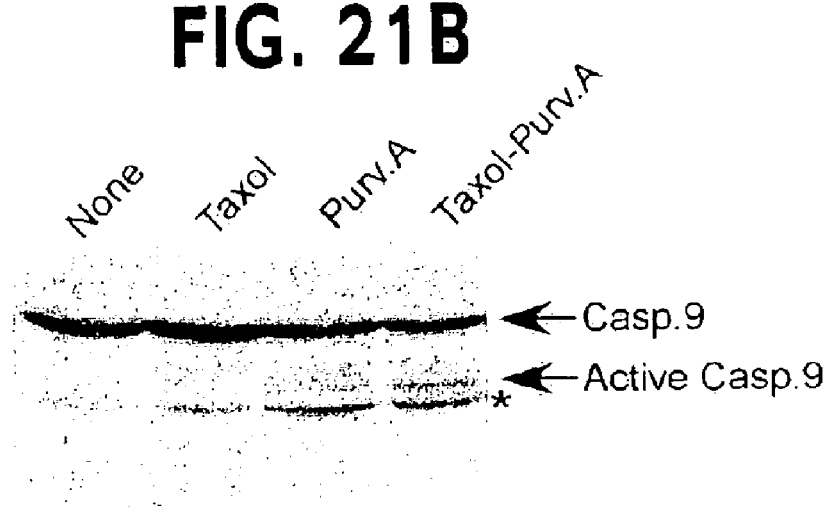

Timed Ablation of p34$^{cdc2}$ Kinase Activity Induces Apoptosis During Spindle Checkpoint Activation: The mitotic arrest induced in HeLa cells by low concentrations (0.2 μM) of taxol was associated with negligible induction of apoptosis for up to 32 h (FIG. 21A, inset). Under these experimental conditions, sequential addition of Purvalanol A to taxol-treated cells caused escape from the mitotic block, and massive apoptosis (FIG. 21A, inset). Sixteen h after taxol-Purvalanol A treatment, ~80% of the cell population exhibited hypodiploid (apoptotic) DNA content, as opposed to 16% or 6% cell death in cultures treated with taxol or Purvalanol A alone, respectively (FIGS. 21A, C). Induction of apoptosis by taxol-Purvalanol A sequential treatment was associated with proteolytic processing of 46 kD proform caspase-9 to a ~37 kD active caspase-9 fragment (FIG. 21B). In contrast, treatment with Purvalanol A or taxol alone did not result in significant caspase-9 cleavage (FIG. 21B). Seventy two to 96 h after taxol-Purvalanol A treatment, a fraction of HeLa cells with 8N and 16N DNA content was also observed (not shown), suggestive of DNA endoreduplication and polyploidy, in agreement with previous observations (J. E. Itzhaki et al. (1997) Nat. Gen. 15: 258–265).

Figure 21C:
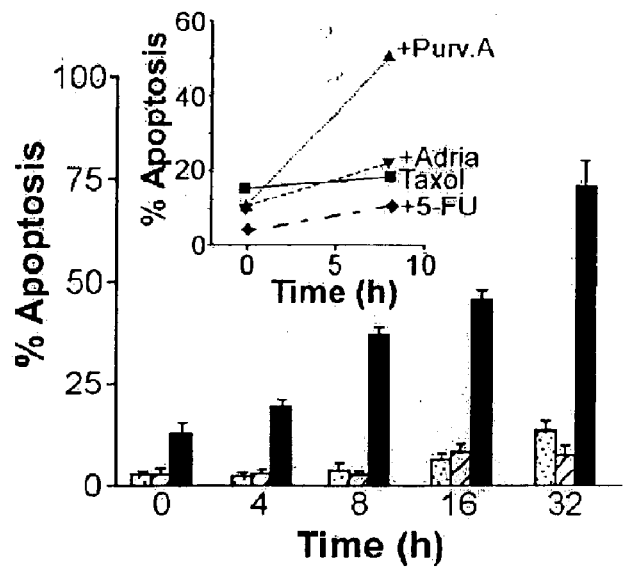
Figure 21D:
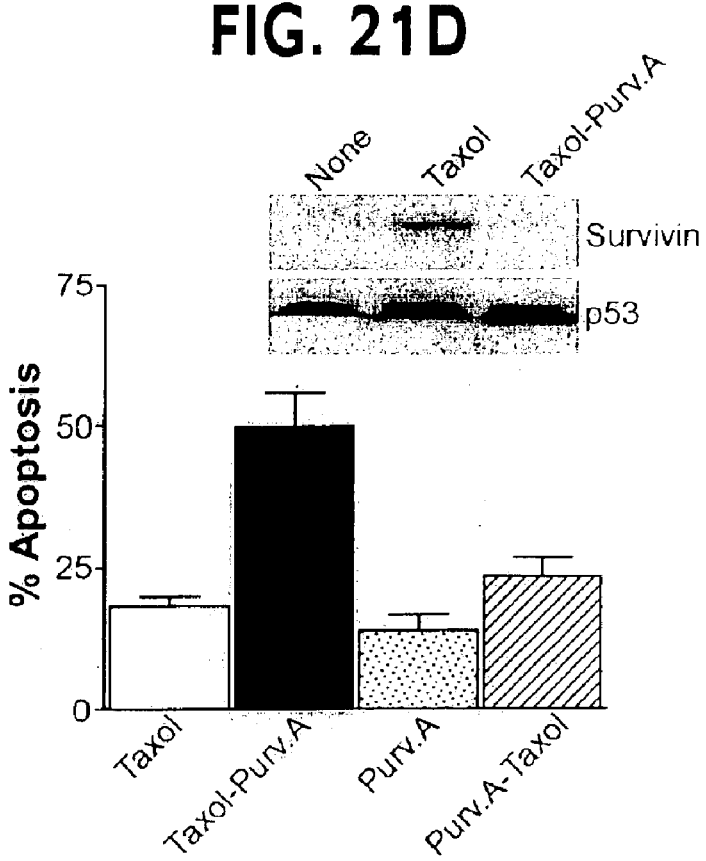
Figure 22A:
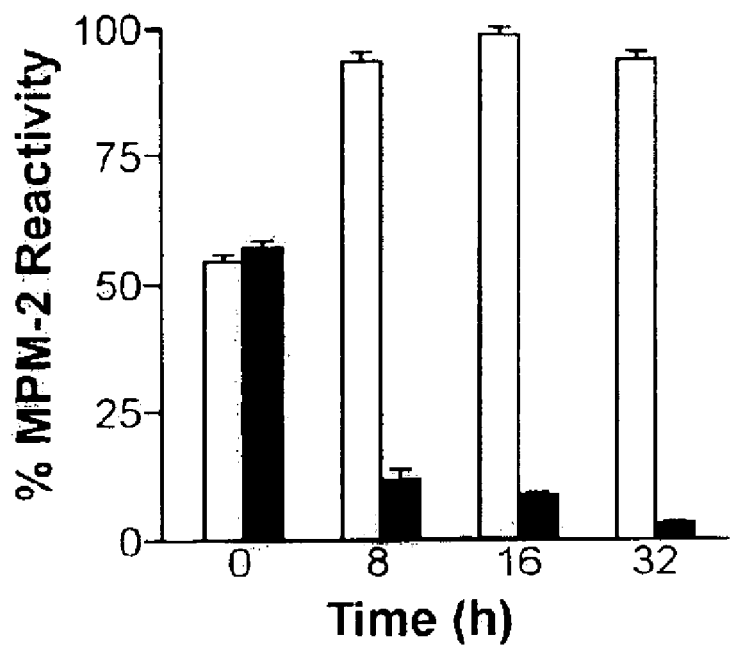
Figure 22B:
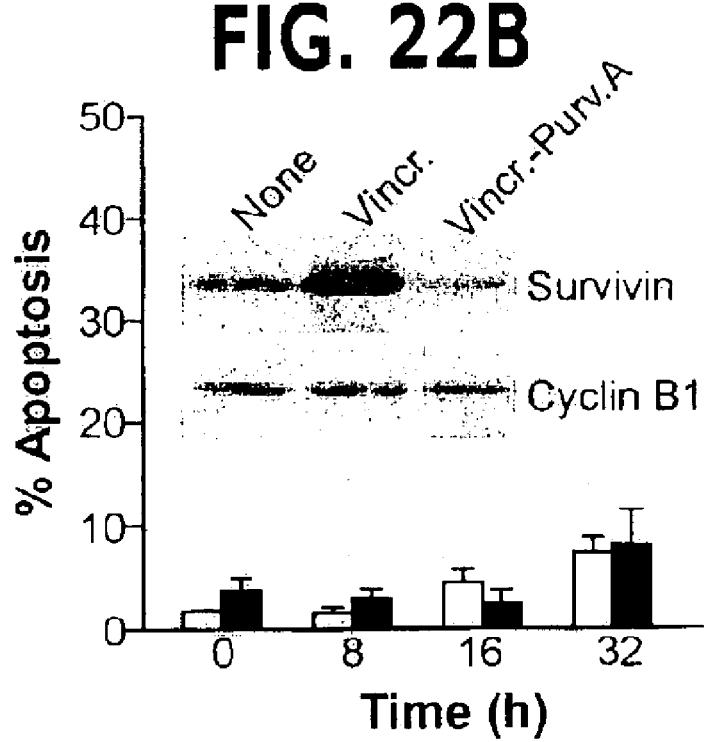

Characterization of Taxol-Purvalanol A-Induced Apoptosis: In a first series of experiments, exposure of HeLa cells to the reverse combination of Purvalanol A followed by taxol (0.2 μM) resulted in a sustained mitotic arrest with undetectable MPM-2 mitotic phosphoepitope expression (not shown), and negligible apoptosis throughout a 32 h culture (FIG. 21C). Secondly, substituting Purvalanol A with the DNA damaging agent, adriamycin, or the nucleoside analog 5-fluorouracile (5-FU) after taxol treatment did not result in enhanced apoptosis, as compared with single agent treatment alone (FIG. 21C, inset). Thirdly, a 2–3 fold increased apoptosis by the taxol-Purvalanol A sequential treatment was also demonstrated in prostate carcinoma PC3 cells, carrying a mutated copy of p53, as compared with taxol, Purvalanol A alone or the reverse Purvalanol A-taxol combination (FIG. 21D). In addition, taxol treatment of PC3 cells was also associated with increased expression of survivin, in a reaction reversed by sequential treatment with Purvalanol A, by Western blotting (FIG. 21D, inset).

p34$^{cdc2}$-Dependent Cytoprotection Requires a Stabilized Microtubule Environment: To determine a potential role of microtubule integrity in p34$^{cdc2}$/survivin cytoprotection, the microtubule-depolymerizing agent, vincristine was used. Treatment of HeLa cells with vincristine resulted in a sustained mitotic (prometaphase) arrest with elevated p34$^{cdc2}$ kinase activity (FIG. 22A), and increased survivin expression, by Western blotting (FIG. 22B, inset). Sequential addition of Purvalanol A to vincristine-treated cells suppressed p34$^{cdc2}$ kinase activity at the earliest time point tested of 8 h (FIG. 22A), and reversed the increase in survivin expression (FIG. 22B, inset). However, at variance with taxol, sequential addition of Purvalanol A to vincristine-treated cells did not result in induction of apoptosis throughout a 32-h culture (FIG. 22B). After 96 h, vincristine-induced apoptosis was indistinguishable in the presence or the absence of Purvalanol A (not shown).

Figure 22C:
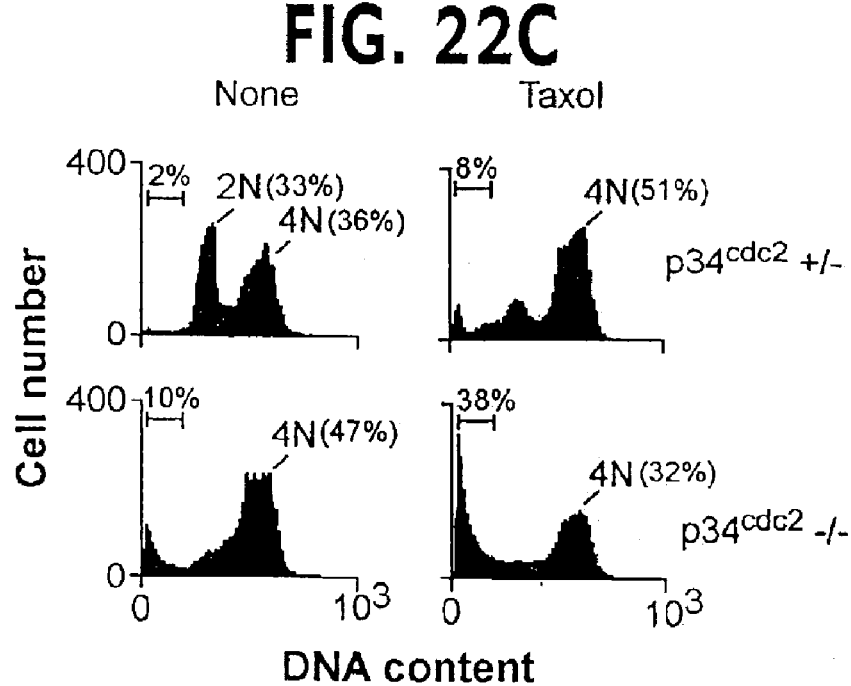
Figure 22D:
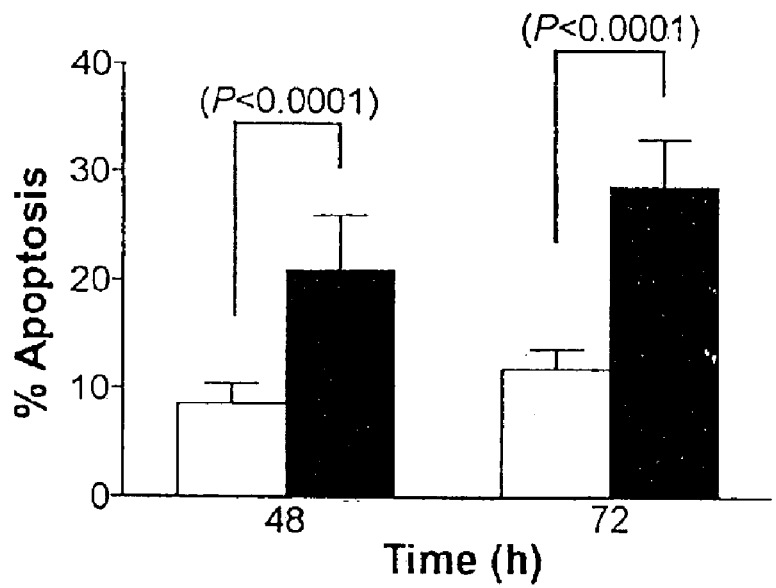

The requirement of p34$^{cdc2}$ kinase in cell viability after spindle checkpoint activation was further investigated using p34$^{cdc2}$ conditional knockout cells. In the presence of a functional p34$^{cdc2}$ allele (p34$^{cdc2}$ +/-), HT2-19 cells exhibited negligible apoptosis, and responded to taxol with homogeneous mitotic arrest (FIG. 22C). Upon IPTG withdrawal, p34$^{cdc2}$ -/- HT2-19 cells also exhibited a coordinated mitotic arrest, and a modest increase in the fraction with hypodiploid (apoptotic) DNA content, in agreement with published observations (J. E. Itzhaki et al. (1997) Nat. Gen. 15: 258–265). Under these experimental conditions and consistent with the data of pharmacologic (Purvalanol A) inhibition of p34$^{cdc2}$ kinase, taxol treatment of IPTG-HT2-19 cells (p34$^{cdc2}$ -/-) resulted in escape from mitotic block, and considerably increased apoptosis, as compared with untreated IPTG-cultures (FIG. 22C). To determine if expression of survivin was sufficient to rescue p34$^{cdc2}$ -/- cells from apoptosis, we used replication-deficient adenoviruses encoding wild type survivin (pAd-Survivin) or GFP (pAd-GFP) (M. Mesri et al. (2001) J. Clin. Invest. 108: 981–990). Infection of HT2-19 cells with pAd-Survivin or pAd-GFP resulted in comparable levels of GFP expression in >95% of the transduced cell population, by fluorescence microscopy (not shown). Consistent with the data presented above, loss of p34$^{cdc2}$ resulted in progressive induction of apoptosis in IPTG-HT2-19 cells (J. E. Itzhaki et al. (1997) Nat. Gen. 15: 258–265), which was not affected by infection with pAd-GFP (FIG. 22D). In contrast, adenoviral expression of survivin completely suppressed apoptosis in p34$^{cdc2}$ -/- cells to background levels of untreated, IPTG+cultures (FIG. 22D).

Sequential Inhibition of p34$^{cdc2}$ Kinase Activity After Microtubule Stabilization as a Novel Anti-Cancer Regimen:

Subcutaneous injection of MCF-7 cells in immunocompromised CB-17 SCID mice gave rise to exponentially growing tumors (FIG. 23A) (M. Mesri et al. (2001) *J. Clin. Invest.* 108: 981–990). Treatment with vehicle, taxol alone (2.5 or 5 mg/kg), or Purvalanol A alone (20 mg/kg) did not affect the kinetics of tumor growth, and resulted in loss of all animals by 21–23 d (FIGS. 23A–C). In contrast, sequential administration of taxol followed by Purvalanol A completely suppressed tumor growth in a concentration-dependent manner (FIG. 23A). In survival curves, the taxol-Purvalanol A sequential treatment resulted in significantly improved animal survival even after suspension of treatment, as compared with single-agent therapy alone (FIG. 23B; P<0.0008 for 5 mg/kg taxol). Conversely, continued administration of taxol-Purvalanol A resulted in indefinite survival of all treated animals (FIG. 23B). To determine if human tumors retained sensitivity to the taxol-Purvalanol A sequential regimen, animals were treated with one taxol-Purvalanol A cycle, followed by a 6-d interruption before re-administration of taxol-Purvalanol A combination. In these animals, MCF-7 tumors doubled in size during suspension of treatment (FIG. 23C). However, re-introduction of taxol-Purvalanol A sequential therapy suppressed additional tumor growth and afforded long-term survival of all treated animals (FIG. 23C). None of the animals in the various treatment groups exhibited signs of systemic toxicity throughout the different treatment cycles.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

What is claimed is:

1. A sequential therapy method for treating cancer comprising administering at least one effective dose of taxol followed by at least one effective dose of purvalanol A.

2. The method of claim 1, wherein purvalanol A is administered about four hours or more after administering taxol.

3. The method of claim 2, wherein purvalanol A is administered about 16 to about 18 hours after administering taxol.

4. The method of claim 3, wherein purvalanol A is administered about 18 hours after administering taxol.

5. The method of claim 1, wherein the taxol and purvalanol are administered to a mammal.

6. The method of claim 5, wherein the mammal is a human.

7. A method of inducing tumor cell apoptosis comprising administering at least one effective dose of taxol followed by administering at least one effective dose of purvalanol A.

8. The method of claim 7, wherein purvalanol A is administered about four hours or more after administering taxol.

9. The method of claim 8, wherein purvalanol A is administered about 16 to about 18 hours after administering taxol.

10. The method of claim 9, wherein purvalanol A is administered about 18 hours after administering taxol.

11. The method of claim 7, wherein the taxol and purvalanol A are administered to a mammal.

12. The method of claim 11, wherein the mammal is a human.

13. A method of inhibiting tumor growth comprising administering at least one effective dose of taxol followed by administering at least one effective dose of purvalanol A.

14. The method of claim 13, wherein purvalanol A is administered about four hours or more after administering taxol.

15. The method of claim 14, wherein purvalanol A is administered about 16 to about 18 hours after administering taxol.

16. The method of claim 15, wherein purvalanol A is administered about 18 hours after administering taxol.

17. The method of claim 13, wherein the taxol and purvalanol A are administered to a mammal.

18. The method of claim 17, wherein the mammal is a human.

19. A method of inducing cell death in a malignant cell population comprising administering at least one effective dose of taxol followed by administering at least one effective dose of purvalanol A.

20. The method of claim 19, wherein purvalanol A is administered about four hours or more after administering taxol.

21. The method of claim 20, wherein purvalanol A is administered about 16 to about 18 hours after administering taxol.

22. The method of claim 21, wherein purvalanol A is administered about 18 hours after administering taxol.

23. The method of claim 19, wherein the taxol and purvalanol A are administered to a mammal.

24. The method of claim 23, wherein the mammal is a human.

25. A method of treating a patient with cancer comprising administering at least one effective dose of taxol followed by administering at least one effective dose of purvalanol A.

26. The method of claim 25, wherein purvalanol A is administered about four hours or more after administering taxol.

27. The method of claim 26, wherein purvalanol A is administered about 16 to about 18 hours after administering taxol.

28. The method of claim 27, wherein purvalanol A is administered about 18 hours after administering taxol.

29. The method of claim 25, wherein the cancer is selected from the group consisting of breast cancer, ovarian cancer, lung cancer, AIDS related-Kaposi's sarcoma and nonsmall cell lung cancer.

30. The method of claim 29, wherein the cancer is breast cancer or ovarian cancer.

31. The method of claim 25, wherein the patient is a human.

32. A pharmaceutical composition formulated for sequential delivery comprising an effective dose of taxol and an effective dose of purvalanol A.

33. A kit comprising an effective dose of taxol and an effective dose of purvalanol A.

* * * * *